US012559491B2

(12) United States Patent
Ford et al.

(10) Patent No.: US 12,559,491 B2
(45) Date of Patent: Feb. 24, 2026

(54) MODIFIED IMIDAZOPYRIDINES AS GLUCOSYLCERAMIDE SYNTHASE INHIBITORS

(71) Applicant: Merck Sharp & Dohme LLC, Rahway, NJ (US)

(72) Inventors: Melissa C. Ford, Sellersville, PA (US); Mark E. Fraley, North Wales, PA (US); Kristen L.G. Jones, Oreland, PA (US); H. Marie Loughran, Perkasie, PA (US); James J. Mulhearn, Elkins, PA (US); Anthony J. Roecker, Harleysville, PA (US); Kathy M. Schirripa, Harleysville, PA (US); Ling Tong, Warren, NJ (US)

(73) Assignee: Merck Sharp & Dohme LLC, Rahway, NJ (US)

(*) Notice: Subject to any disclaimer, the term of this patent is extended or adjusted under 35 U.S.C. 154(b) by 473 days.

(21) Appl. No.: 18/043,385

(22) PCT Filed: Sep. 15, 2021

(86) PCT No.: PCT/US2021/050359
§ 371 (c)(1),
(2) Date: Feb. 28, 2023

(87) PCT Pub. No.: WO2022/060763
PCT Pub. Date: Mar. 24, 2022

(65) Prior Publication Data

US 2024/0018140 A1 Jan. 18, 2024

Related U.S. Application Data

(60) Provisional application No. 63/079,495, filed on Sep. 17, 2020.

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC .................................................... C07D 471/04
USPC ........................................................ 514/300
See application file for complete search history.

(56) References Cited

U.S. PATENT DOCUMENTS 7,157,488 B2 * 1/2007 Chen .................... C07D 277/34 548/503
7,838,542 B2 * 11/2010 Hangauer, Jr. .......... A61P 17/06 514/359
2017/0349594 A1 12/2017 Kim et al.

FOREIGN PATENT DOCUMENTS

WO 2010091104 A1 8/2010

OTHER PUBLICATIONS

Tsegay et al., Bulletin of the Chemical Society of Ethiopia (2019), 33(3), 401-413.*

(Continued)

*Primary Examiner* — Niloofar Rahmani
(74) *Attorney, Agent, or Firm* — Patricia A. Shatynski; John C. Todaro

(57) ABSTRACT

The present invention relates to Compounds of Formula I: I and pharmaceutically acceptable salts or prodrug thereof. The present invention also relates to compositions comprising at least one compound of Formula I, and methods of using the compounds of Formula I for treatment or prophylaxis of lysosomal storage diseases, neurodegenerative disease, cystic disease, cancer, or a diseases or disorders associated with elevated levels of glucosylceramide (GlcCer), glucosylsphingosine (GlcSph) and/or other glucosylceramide-based glycosphingolipids (GSLs).

I

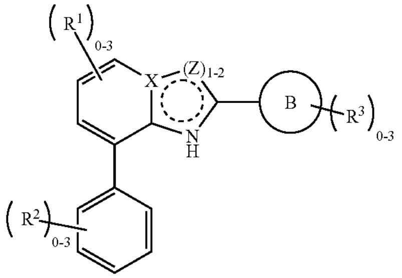

16 Claims, No Drawings

(56) References Cited

OTHER PUBLICATIONS

Liu et al., Organic & Biomolecular Chemistry (2019), 17(20), 5099-5105.*
Vuong et al., Organic Letters (2018), 20(7), 1849-1852.*
Yamaguchi et al., Organic & Biomolecular Chemistry (2017), 15(31), 6645-6655.*
Lee et al., Organometallics (2016), 35(11), 1973-1977.*
Cacchi et al., Tetrahedron (2015), 71(49), 9346-9356.*
Kiefer et al., Bioorganic & Medicinal Chemistry (2016), 24(4), 554-569.*
Nicolaou et al., Journal of the American Chemical Society (2009), 131(10), 3690-3699.*
Kost, A.N.et al., 7-Phenylindoles and conjugation of the benzene ring with indole nucleus, Zhurnal Organicheskoi 1 Khimii, vol. 1, No. 1, 121-125 (translation), 1965.
PubChem Compund Summary for CID 70829592, '5-Fluoro-7-(4-fluorophenyl)-N-[(3-fluorophenyl)methyl]-2-3-dihydro-1-H-indole-2-carboxamide', U S National Library of Medicine, Mar. 21, 2013 (Mar. 21, 2013), pp. 1-7; (https://pubchem.ncbi.nlm.nih.gov/compound/70829592); p. 2(7 pages).
Pubmed Compound Record for CID 82388407, '7-Phenyl-2,3-dihydro-1 H-indole-2-carboxylic acid', U.S. National Library of Medicine, Oct. 20, 2014 (Oct. 20, 2014), pp. 1-7 (https://pubchem.ncbi.nlm.nih.gov/compound/82388407); p. 2(7 pages).

* cited by examiner

MODIFIED IMIDAZOPYRIDINES AS GLUCOSYLCERAMIDE SYNTHASE INHIBITORS

CROSS-REFERENCE TO RELATED APPLICATIONS

This application is a U.S. National Stage application of International Patent Application No. PCT/US21/050359, filed Sep. 15, 2021, which claims priority to U.S. Provisional Patent Application No. 63/079,495, filed Sep. 17, 2020.

FIELD OF THE INVENTION

The present invention is directed to a class of modified imidazopyridine compounds, their salts, pharmaceutical compositions comprising them and their use in the treatment of human disease. In particular, the invention is directed to a class of glucosylceramide synthase (GCS) inhibitors, and hence are useful in the treatment of lysosomal storage diseases, neurodegenerative disease, cystic disease, cancer, or a diseases or disorders associated with elevated levels of glucosylceramide (GlcCer), glucosylsphingosine (GlcSph) and/or other glucosylceramide-based glycosphingolipids (GSLs), either alone or in combination with enzyme replacement therapy.

BACKGROUND OF THE INVENTION

Glucosylceramide synthase (GCS) is a ubiquitously expressed, Golgi membrane-bound, 394 amino acid enzyme that glycosylates ceramide to form glucosylceramide (GlcCer), the first step in the biosynthesis of an extensive family of glycosphingolipids (GSLs) that are integral components of cellular structure and function (Ichikawa, S. et al. Proc. Natl. Acad. Sci. USA, 1996, 93, 4638). Inhibitors of GCS have been proposed and/or investigated for use in the treatment for a variety of diseases, including lysosomal storage diseases such as Niemann-Pick type C, Fabry, Tay-Sachs, and Sandhoff, among others (Platt, F. M., Nat. Rev. 2018, 17, 133). Gaucher's disease (GD) is lysosomal storage disorder resulting from the accumulation of GlcCer due to loss-of-function mutations in the GBA1 gene, which encodes glucocerbrosidase (GCase), a lysosomal hydrolase that metabolizes GlcCer and GlcSph. Eliglustat (Cerdelga®) is a GCS inhibitor (GCSi) approved for the treatment of type 1 GD (Balwani, M., et al., Mol. Genet. Metab. 2016, 117, 95). Mutations in GBA1 also represent a prevalent genetic risk factor for Parkinson's disease (PD) (Sidransky, E. et al., Lancet Neurol. 2012, 11, 986). In laboratory models, reduction of GCase activity through mutations or chemical inhibition has been shown to elevate levels of glycolipids and accelerate formation of α-synuclein aggregates, a pathological hallmark of PD (Mazzulli, J. R. et al., Cell 2011, 146, 37; Manning-Boğ, A. B. et al., Neurotoxicology 2009, 30, 1127). Conversely, GCSi's have been shown to lower GSL levels and attenuate α-synuclein formation in similar models. As an example, eliglustat has been shown to reverse the formation of pathological α-synuclein aggregates in GD and PD patient-derived induced pluripotent stem cell (iPSC) neurons (Zunke, F. et al., Neuron 2018, 97, 92). Furthermore, a brain penetrant, GCSi has been shown to reduce central α-synuclein accumulation and attenuate cognitive impairment in a GBA-mutant mouse model (Sardi, S. P. et al., Proc. Natl. Acad. Sci. 2017, 114, 2699). These recent data support the proposal that GCSi's may be useful for the treatment of PD and related diseases, such as dementia with Lewy bodies. Additional proposed therapies for GCSi's include other diseases associated with elevated GSL levels, such as polycystic kidney disease, renal hypertrophy and diabetic nephropathy, diabetes mellitus and obesity, and hyperglycemia or hyperinsulemia, and cancers where GSL synthesis is abnormal, or overexpression of GCS disrupts ceramide-induced apoptosis.

SUMMARY OF THE INVENTION

In one aspect, the present invention provides compounds of Formula I or pharmaceutically acceptable salts thereof:

I

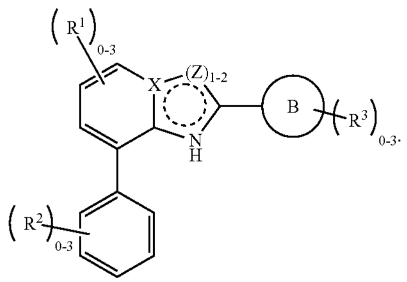

The invention is further directed to methods of treating a patient (preferably a human) for diseases or disorders in which elevated levels of glucosylceramide (GlcCer), glucosylsphingosine (GlcSph), and/or other glucosylceramide-based glycosphingolipids (GSLs) are involved. The invention further involves use of the compounds as GCS inhibitors for the preparation of a medicament for the treatment and/or prevention of diseases associated with inhibiting GCS, which includes metabolic diseases, such as lysosomal storage diseases, neurodegenerative disease, such as Parkinson's disease (PD) and dementia with Lewy bodies (DLB), cystic disease, and cancer. The invention is also directed to pharmaceutical compositions which include an effective amount of a compound of Formula I, or a pharmaceutically acceptable salt thereof, and a pharmaceutically acceptable carrier, and the use of the compounds and pharmaceutical compositions of the invention in the treatment of such diseases.

Other embodiments, aspects and features of the present invention are either further described in or will be apparent from the ensuing description, examples and appended claims.

DETAILED DESCRIPTION OF THE INVENTION

The present invention includes compounds of formula I

I

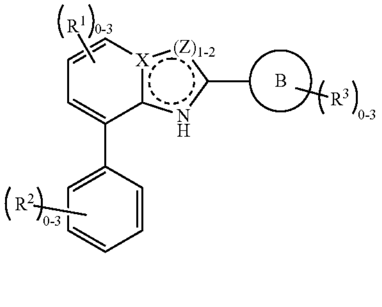

or a pharmaceutically acceptable salt thereof, wherein

X is C or N;

Z is —$CR^4$—, each $R^1$ is independently C1-C4 alkyl, C1-C4 fluoroalkyl, —C0-C4alkylOH, cyano, C1-C4alkoxy, or halo;

each $R^4$ is independently hydrogen, C1-C4 alkyl, C1-C4 fluoroalkyl, —C0-C4alkylOH, cyano, C1-C4alkoxy, or halo;

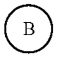

is selected from (C1-C6 haloalkyl)aminocarbonyl,
(C1-C6 haloalkyl)oxy,
(C1-C6 alkyl)aminocarbonyl,
(C0-C6 alkyl)amino(C1-C4 alkyl),
(C0-C4 alkyl)amino(C1-C4 alkyl)aminocarbonyl,
(C1-C4 haloalkyl)amino(C1-C4 alkyl)aminocarbonyl,
C1-C8alkylOH,
cycloalkylC0-C4 alkyl,
cycloalkylC0-C4 alkylaminocarbonyl,
cycloalkyl(C0-C4 alkyl)carbonyl,
heterocycloalkylC0-C4 alkyl,
heterocycloalkyl(C0-C4 alkyl)aminocarbonyl,
heterocycloalkyl(C0-C4 alkyl)carbonyl,
heteroarylC0-C4 alkyl,
heteroaryl(C0-C4 alkyl)aminocarbonyl,
heteroaryl(C0-C4 alkyl)carbonyl,
arylC0-C4 alkyl,
aryl(C0-C4 alkyl)aminocarbonyl, and
aryl(C0-C4 alkyl)carbonyl;

each $R^2$ is independently selected from halo, (C1-C4 fluoroalkyl)oxy, hydroxy, C1-C4 alkyl, and —(C0-C4 alkyl)O(C1-C4 alkyl); and each $R^3$ is independently selected from C1-C4 alkyl, halo, oxo, cyano, amino, C1-C4 fluoroalkyl, hydroxy, —(C0-C4alkyl)O(C1-C4 alkyl), and —(C1-C4 alkyl)OH.

In a first embodiment of the invention, each $R^1$ is independently methyl, ethyl, propyl, difluoromethyl, trifluoromethyl, 2,2,2-trifluoroethyl, hydroxy, hydroxymethyl, cyano, methoxy, ethoxy, chloro, or fluoro; and the other groups are as provided in the general formula above.

In a second embodiment of the invention, each $R^1$ is independently chloro, trifluoromethyl, methoxy, fluoro, or cyano, and the other groups are as provided in the general formula above.

In a third embodiment of the invention each $R^2$ is independently chloro, fluoro, trifluoromethoxy, trifluoroethoxy, 2,2,2-trifluoroethoxy, hydroxy, methyl, ethyl, isopropyl, methoxy, ethoxy, ethoxymethyl, or methoxymethyl, and the other groups are as provided in the general formula above or as in the first and second embodiments.

In a fourth embodiment of the invention, each $R^2$ is independently methoxy, fluoro, chloro, or (2,2,2-trifluoroethyl)oxy and the other groups are as provided in the general formula above, or as in the first or second embodiments.

In a fifth embodiment of the invention, each $R^3$ independently is selected from methyl, ethyl, propyl, isopropyl, butyl, fluoro, chloro, oxo, cyano, amino, trifluoromethyl, 2,2,2-trifluoroethyl, hydroxy, methoxy, ethoxy, propoxy, hydroxymethyl, hydroxyethyl, hydroxypropyl, and 2-hydroxy(prop-2yl); and the other groups are as provided in the general formula above, or as in the first through fourth embodiments.

In a sixth embodiment of the invention each $R^3$ independently is selected from fluoro, methyl, hydroxymethyl, fluoromethyl, aminomethyl, 2-hydroxy(prop-2yl), hydroxy, cyano, methoxyethyl, methoxymethyl, trifluoromethyl and methoxy; and the other groups are as provided in the general formula above, or as in the first through fourth embodiments.

In a seventh embodiment, each $R^4$ independently is selected from hydrogen, methyl, ethyl, propyl, isopropyl, butyl, trifluoromethyl, trifluoroethyl, trifluoropropyl, fluoromethyl, difluoromethyl, difluoroethyl, hydroxy, hydroxymethyl, hydroxyethyl, hydroxyisopropyl, hydroxypropyl, cyano, methoxy, ethoxy, propoxy, isopropoxy, butoxy, chloro, fluoro, and bromo; and the other groups are as provided in the general formula above, or as in the first through sixth embodiments.

In an eighth embodiment, each $R^4$ independently is selected from hydrogen and fluoro, and the other groups are as provided in the general formula above, or as in the first through sixth embodiments In a ninth embodiment,

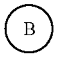

is selected from (C1-C6 haloalkyl)aminocarbonyl,
(C1-C6 haloalkyl)oxy,
(C1-C6 alkyl)aminocarbonyl,
(C0-C6 alkyl)amino(C1-C4 alkyl),
(C0-C4 alkyl)amino(C1-C4 alkyl)aminocarbonyl,
(C1-C4 haloalkyl)amino(C1-C4 alkyl)aminocarbonyl,
C1-C8alkylOH,
cycloalkylC0-C4 alkyl,
cycloalkylC0-C4 alkylaminocarbonyl,
cycloalkyl(C0-C4 alkyl)carbonyl,
heterocycloalkylC0-C4 alkyl,
heterocycloalkyl(C0-C4 alkyl)aminocarbonyl,
heterocycloalkyl(C0-C4 alkyl)carbonyl,
heteroarylC0-C4 alkyl,
heteroaryl(C0-C4 alkyl)aminocarbonyl,
heteroaryl(C0-C4 alkyl)carbonyl,
arylC0-C4 alkyl,
aryl(C0-C4 alkyl)aminocarbonyl, and
aryl(C0-C4 alkyl)carbonyl; wherein each cycloalkyl is independently selected from decalinyl, spiro[4.5]decanyl, cyclopropyl, cyclobutyl, cyclopentyl, cyclohexyl, cycloheptyl, bicyclo[2.2.2]octanyl, bicyclo[1.1.1]pentyl, bicyclo[2.2.1]heptyl, [1.1.1]-bicyclo pentanyl, 1-decalinyl, spiro[2.4]heptyl, spiro[2.2]pentyl, 2,3-dihydro-1H-indenyl, and norbornyl;

each heterocycloalkyl is independently selected from piperidinyl, piperazinyl, morpholinyl, pyrrolidinyl, tetrahydrofuranyl, azetidinyl, oxiranyl, aziridinyl, oxetanyl, oxetenyl, piperidyl, pyrrolidinyl, piperazinyl, morpholinyl, thiomorpholinyl, thiazolidinyl, 1,4-dioxanyl, tetrahydrofuranyl, tetrahydrothiophenyl, 6,7-dihydro-5H-cyclopenta[b]pyridine, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, I-oxo-thiomorpholinyl, decahydroisoquinoline, 1,4-dioxaspiro[4.5]decane, 2,5-diazabicyclo[2.2.1]heptyl, dioxa-9-azospiro[4.5]decanyl, 5,7-dihydro-6H-pyrrolo[3,4-b]pyridinyl, 4,5-dihydrooxazolyl, oxa-2,8-diazaspiro[3.5]nonanyl, dioxaazaspiro[3.5]nonanyl, 5,6-dihydroimidazo[1,2-a]pyrazinyl, azabicyclo[3.1.0]hexanyl, 2,7diazaspiro[3.4]octenyl, and 1,1-dioxothiomorpholinyl; each heteroaryl is independently selected from azaindolyl, benzoimidazolyl, benzisoxazolyl, benzofuranyl, benzofurazanyl, benzopyrazolyl, benzotriazolyl, benzothiophenyl, benzothiazolyl, benzo[d]isothiazole, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyrrolyl, pyrazolopyrimidinyl, pyridazinyl, pyridyl, pyrimidyl, pyrimidinyl, pyrrolyl, quinazolinyl, quinolyl, quinoxalinyl, tetrazolyl, tetrazolopyridyl, thiadiazolyl, 5H-pyrrolo[3,4-b]pyridine, thiazolyl, thienyl, triazolyl, triazinyl, benzothiazolyl, benzothienyl, quinolinyl, quinazolinyl, and isoquinolinyl, and oxazolyl;

and each aryl is independently phenyl or naphthyl; and the other groups are as provided in the general formula above, or as in the first through eighth embodiments.

In a tenth embodiment of the invention,

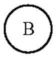

is selected from (C1-C6 haloalkyl)aminocarbonyl, (C1-C6 alkyl)aminocarbonyl, (C0-C6 alkyl)amino(C1-C4 alkyl), (C0-C4 alkyl)amino(C1-C4 alkyl)aminocarbonyl, C1-C8alkylOH, cycloalkylC0-C4 alkyl, cycloalkylC0-C4 alkylaminocarbonyl, heterocycloalkylC0-C4 alkyl, heterocycloalkyl(C0-C4 alkyl)aminocarbonyl, heterocycloalkyl(C0-C4 alkyl)carbonyl, and heteroaryl(C0-C4 alkyl)aminocarbonyl, wherein each cycloalkyl is independently selected from decalinyl, spiro[4.5]decanyl, cyclopropyl, cyclobutyl, cyclopentyl, cyclohexyl, cycloheptyl, bicyclo[2.2.2]octanyl, bicyclo[1.1.1]pentyl, bicyclo[2.2.1]heptyl,[1.1.1]-bicyclo pentanyl, 1-decalinyl, spiro[2.4]heptyl, spiro[2.2]pentyl, 2,3-dihydro-1H-indenyl, and norbornyl;

each heterocycloalkyl is independently selected from piperidinyl, piperazinyl, morpholinyl, pyrrolidinyl, tetrahydrofuranyl, azetidinyl, oxiranyl, aziridinyl, oxetanyl, oxetenyl, piperidyl, pyrrolidinyl, piperazinyl, morpholinyl, thiomorpholinyl, thiazolidinyl, 1,4-dioxanyl, tetrahydrofuranyl, tetrahydrothiophenyl, 6,7-dihydro-5H-cyclopenta[b]pyridine, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, I-oxo-thiomorpholinyl, decahydroisoquinoline, 1,4-dioxaspiro[4.5]decane, 2,5-diazabicyclo[2.2.1]heptyl, dioxa-9-azospiro[4.5]decanyl, 5,7-dihydro-6H-pyrrolo[3,4-b]pyridinyl, 4,5-dihydrooxazolyl, oxa-2,8-diazaspiro[3.5]nonanyl, dioxaazaspiro[3.5]nonanyl, 5,6-dihydroimidazo[1,2-a]pyrazinyl, azabicyclo[3.1.0]hexanyl, 2,7diazaspiro[3.4]octenyl, and 1,1-dioxothiomorpholinyl; each heteroaryl is independently selected from azaindolyl, benzoimidazolyl, benzisoxazolyl, benzofuranyl, benzofurazanyl, benzopyrazolyl, benzotriazolyl, benzothiophenyl, benzothiazolyl, benzo[d]isothiazole, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyrrolyl, pyrazolopyrimidinyl, pyridazinyl, pyridyl, pyrimidyl, pyrimidinyl, pyrrolyl, quinazolinyl, quinolyl, quinoxalinyl, tetrazolyl, tetrazolopyridyl, thiadiazolyl, 5H-pyrrolo[3,4-b]pyridine, thiazolyl, thienyl, triazolyl, triazinyl, benzothiazolyl, benzothienyl, quinolinyl, quinazolinyl, and isoquinolinyl, and oxazolyl; and the other groups are as provided in the general formula above, or as in the first through eighth embodiments.

In an eleventh embodiment of the invention,

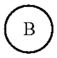

is selected from (tetrahydropuranyl)aminocarbonyl, (tetrahydro-2H-puranyl)aminocarbonyl, (1,1,1-trifluoro-2-methylprop-2yl)aminocarbonyl, (tetrahydrofuranyl)aminocarbonyl, cyclopropylaminocarbonyl, piperazinylcarbonyl, isobutylaminocarbonyl, (3,3,3-trifluoroprop-2yl)aminocarbonyl, tertbutylaminocarbonyl, (6,7-dihydropyrrolo[3,4-b]pyridyl)carbonyl ((6,7-dihydro-5H-pyrrolo[3,4-b]pyridyl)carbonyl), 1-hydroxyethyl, 2-hydroxyprop-2yl, hydroxymethyl, dihydrooxazolyl, 4,5-dihydrooxazolyl, pyridinylaminocarbonyl, 2-pyridylaminocarbonyl, 3-pyridylaminocarbonyl, (4-pyridyl)aminocarbonyl, piperidinylaminocarbonyl, (bicyclo[2.2.2]octanyl)aminocarbonyl, cyclopentylaminocarbonyl, cyclohexylaminocarbonyl, (trifluoromethylaminomethyl)aminocarbonyl, (trifluoromethylaminoethyl)aminocarbonyl, (bicyclo[2.2.1]heptyl)aminocarbonyl, tetrahydropyranylaminocarbonyl, N-(tetrahydro-2H-pyran-3-yl)aminocarbonyl, (pyridylmethyl)aminocarbonyl, cyclobutylaminocarbonyl, (bicyclo[1.1.1]pentyl)aminocarbonyl, (azabicyclo[2.1.1]hexyl)carbonyl, (2-azabicyclo[2.1.1]hexyl)carbonyl, (oxadiazaspiro[3.5]nonyl)carbonyl, (5-oxa-2,8-diazaspiro[3.5]nonyl)carbonyl, (dioxaazaspiro[4.5]decyl)carbonyl, (2,9-dioxa-6-azaspiro[4.5]decyl)carbonyl, (dioxaazaspiro[3.5]nonyl)carbonyl, (2,5-dioxa-8-azaspiro[3.5]nonyl)carbonyl, dihydrooxazolyl, 4,5-dihydrooxazolyl, (pyridylmethyl)aminocarbonyl, (2-pyridylmethyl)aminocarbonyl, (oxetanyl)aminocarbonyl, (3-oxetanyl)aminocarbonyl, oxadiazaspiro[3.4]octenyl, 5-oxa-2,7-diazaspiro[3.4]oct-6-enyl, (pyrrolidinylethyl)aminocarbonyl, (5,6,7,8-tetrahydroimidazo[1,2-a]pyrazinyl)carbonyl, aminomethyl, (azabicyclo[3.1.0]hexyl)carbonyl, (3-azabicyclo[3.1.0]hexyl)carbonyl, cyclopropylmethyl, (tert-butyl)aminomethyl, (tetrahydropyranyl)methyl, (tetrahydro-2H-pyranyl)methyl, and cyclobutylcarbonylamino; and the other groups are as provided in the general formula above, or as in the first through eighth embodiments.

In a twelfth embodiment of the invention, X is C, and the other groups are as provided in the general formula above, or as in the first through eleventh embodiments.

In a thirteenth embodiment of the invention, X is N, and the other groups are as provided in the general formula above, or as in the first through eleventh embodiments.

Non-limiting examples of the Compounds of Formula I include compounds 1-84 or a pharmaceutically acceptable salt thereof, as set forth in the Examples:

N-(1-hydroxy-2-methylpropan-2-yl)-8-(2-(2,2,2-trifluoroethoxy)phenyl)imidazo[1,2-a]pyridine-2-carboxamide;

(R)—N-(tetrahydro-2H-pyran-3-yl)-8-(2-(2,2,2-trifluoroethoxy)phenyl)imidazo[1,2-a]pyridine-2-carboxamide;

(S)—N-(tetrahydro-2H-pyran-3-yl)-8-(2-(2,2,2-trifluoroethoxy)phenyl)imidazo[1,2-a]pyridine-2-carboxamide;

N-(1,1,1-trifluoro-2-methylpropan-2-yl)-8-(2-(2,2,2-trifluoroethoxy)phenyl)imidazo[1,2-a]pyridine-2-carboxamide;

(R)-8-(2-(2,2,2-trifluoroethoxy)phenyl)-N-(1,1,1-trifluoropropan-2-yl)imidazo[1,2-a]pyridine-2-carboxamide;

(S)-6-chloro-N-(tetrahydrofuran-3-yl)-8-(2-(2,2,2-trifluoroethoxy)phenyl)imidazo[1,2-a]pyridine-2-carboxamide;

6-chloro-N-(1-(methoxymethyl)cyclopropyl)-8-(2-(2,2,2-trifluoroethoxy)phenyl)imidazo[1,2-a]pyridine-2-carboxamide;

(6-chloro-8-(2-(2,2,2-trifluoroethoxy)phenyl)imidazo[1,2-a]pyridin-2-yl)(3,3,4-trimethylpiperazin-1-yl)methanone;

6-chloro-N-(2-cyano-2-methylpropyl)-8-(2-(2,2,2-trifluoroethoxy)phenyl)imidazo[1,2-a]pyridine-2-carboxamide;

(S)—N-(1,1,1-trifluoro-3-hydroxy-2-methylpropan-2-yl)-8-(2-(2,2,2-trifluoroethoxy)phenyl)imidazo[1,2-a]pyridine-2-carboxamide;

(R)—N-(1,1,1-trifluoro-3-hydroxy-2-methylpropan-2-yl)-8-(2-(2,2,2-trifluoroethoxy)phenyl)imidazo[1,2-a]pyridine-2-carboxamide;

(R)—N-(1,1,1-trifluoro-3-hydroxy-2-methylpropan-2-yl)-8-(2-(2,2,2-trifluoroethoxy)phenyl)imidazo[1,2-a]pyridine-2-carboxamide;

(S)—N-(1,1,1-trifluoro-3-hydroxy-2-methylpropan-2-yl)-8-(2-(2,2,2-trifluoroethoxy)phenyl)imidazo[1,2-a]pyridine-2-carboxamide;

N-(1-methoxy-2-methylpropan-2-yl)-8-(2-(2,2,2-trifluoroethoxy)phenyl)imidazo[1,2-a]pyridine-2-carboxamide;

(5,7-dihydro-6H-pyrrolo[3,4-b]pyridin-6-yl)(8-(2-(2,2,2-trifluoroethoxy)phenyl)imidazo[1,2-a]pyridin-2-yl)methanone;

N-(tert-butyl)-6-fluoro-8-(2-(2,2,2-trifluoroethoxy)phenyl)imidazo[1,2-a]pyridine-2-carboxamide;

(R)-6-chloro-N-(3-methyltetrahydrofuran-3-yl)-8-(2-(2,2,2-trifluoroethoxy)phenyl)imidazo[1,2-a]pyridine-2-carboxamide;

(S)-6-chloro-N-(3-methyltetrahydrofuran-3-yl)-8-(2-(2,2,2-trifluoroethoxy)phenyl)imidazo[1,2-a]pyridine-2-carboxamide;

N-(pyridin-3-yl)-8-(2-(2,2,2-trifluoroethoxy)phenyl)-6-(trifluoromethyl)imidazo[1,2-a]pyridine-2-carboxamide;

N-(trans-4-fluoropiperidin-3-yl)-8-(2-(2,2,2-trifluoroethoxy)phenyl)imidazo[1,2-a]pyridine-2-carboxamide;

(R)—N-(4,4-difluoropiperidin-3-yl)-8-(2-(2,2,2-trifluoroethoxy)phenyl)imidazo[1,2-a]pyridine-2-carboxamide;

(S)—N-(4,4-difluoropiperidin-3-yl)-8-(2-(2,2,2-trifluoroethoxy)phenyl)imidazo[,2-a]pyridine-2-carboxamide;

N-(4-(hydroxymethyl)bicyclo[2.2.2]octan-1-yl)-8-(2-(2,2,2-trifluoroethoxy)phenyl)imidazo[1,2-a]pyridine-2-carboxamide;

N-(trans-3-hydroxycyclopentyl)-8-(2-(2,2,2-trifluoroethoxy)phenyl)imidazo[1,2-a]pyridine-2-carboxamide;

6-chloro-N-(1-hydroxy-2-methylpropan-2-yl)-8-(2-(2,2,2-trifluoroethoxy)phenyl)imidazo[1,2-a]pyridine-2-carboxamide;

N-(1-(hydroxymethyl)cyclopentyl)-8-(2-(2,2,2-trifluoroethoxy)phenyl)imidazo[1,2-a]pyridine-2-carboxamide;

6-chloro-N-((1S,2R,4S)-2-fluoro-4-hydroxycyclohexyl)-8-(2-(2,2,2-trifluoroethoxy)phenyl)imidazo[1,2-a]pyridine-2-carboxamide;

6-chloro-N-((1R,2S,4R)-2-fluoro-4-hydroxycyclohexyl)-8-(2-(2,2,2-trifluoroethoxy)phenyl)imidazo[1,2-a]pyridine-2-carboxamide;

N-(2-amino-3,3,3-trifluoropropyl)-6-chloro-8-(2-(2,2,2-trifluoroethoxy)phenyl)imidazo[1,2-a]pyridine-2-carboxamide;

6-chloro-N-(trans-4-hydroxycyclohexyl)-8-(2-(2,2,2-trifluoroethoxy)phenyl)imidazo[1,2-a]pyridine-2-carboxamide;

6-chloro-N-(4-hydroxybicyclo[2.2.1]heptan-1-yl)-8-(2-(2,2,2-trifluoroethoxy)phenyl)imidazo[1,2-a]pyridine-2-carboxamide;

cis-6-fluoro-N-(4-hydroxy-4-methylcyclohexyl)-8-(2-(2,2,2-trifluoroethoxy)phenyl)imidazo[1,2-a]pyridine-2-carboxamide;

trans-6-fluoro-N-(4-hydroxy-4-methylcyclohexyl)-8-(2-(2,2,2-trifluoroethoxy)phenyl)imidazo[1,2-a]pyridine-2-carboxamide;

6-fluoro-N-(cis-4-(hydroxymethyl)cyclohexyl)-8-(2-(2,2,2-trifluoroethoxy)phenyl)imidazo[1,2-a]pyridine-2-carboxamide;

N-cyclopentyl-6-fluoro-8-(2-(2,2,2-trifluoroethoxy)phenyl)imidazo[1,2-a]pyridine-2-carboxamide;

N-(trans-4-(hydroxymethyl)cyclohexyl)-8-(2-(2,2,2-trifluoroethoxy)phenyl)imidazo[1,2-a]pyridine-2-carboxamide;

8-(5-chloro-2-methoxyphenyl)-N-(4-hydroxybicyclo[2.2.1]heptan-1-yl)imidazo[1,2-a]pyridine-2-carboxamide;

N-(cis-3-(hydroxymethyl)cyclohexyl)-8-(2-(2,2,2-trifluoroethoxy)phenyl)imidazo[1,2-a]pyridine-2-carboxamide;

3-fluoro-N-(trans-4-hydroxycyclohexyl)-8-(2-(2,2,2-trifluoroethoxy)phenyl)imidazo[1,2-a]pyridine-2-carboxamide;

3-fluoro-N-(1,1,1-trifluoro-2-methylpropan-2-yl)-8-(2-(2,2,2-trifluoroethoxy)phenyl)imidazo[1,2-a]pyridine-2-carboxamide;

(S)—N-(3-cyanotetrahydrofuran-3-yl)-8-(2-(2,2,2-trifluoroethoxy)phenyl)imidazo[1,2-a]pyridine-2-carboxamide;

(R)-6-chloro-N-(3-methyltetrahydro-2H-pyran-3-yl)-8-(2-(2,2,2-trifluoroethoxy)phenyl)imidazo[1,2-a]pyridine-2-carboxamide;

(S)-6-chloro-N-(3-methyltetrahydro-2H-pyran-3-yl)-8-(2-(2,2,2-trifluoroethoxy)phenyl)imidazo[1,2-a]pyridine-2-carboxamide;

N-(trans-4-hydroxycyclohexyl)-8-(2-(2,2,2-trifluoroethoxy)phenyl)-6-(trifluoromethyl)imidazo[1,2-a]pyridine-2-carboxamide;

N-(1-hydroxy-2-methylpropan-2-yl)-8-(2-(2,2,2-trifluoroethoxy)phenyl)-6-(trifluoromethyl)imidazo[1,2-a]pyridine-2-carboxamide;

(R)—N-(2,2,2-trifluoro-1-(pyridin-3-yl)ethyl)-8-(2-(2,2,2-trifluoroethoxy)phenyl)imidazo[1,2-a]pyridine-2-carboxamide;

(S)—N-(2,2,2-trifluoro-1-(pyridin-3-yl)ethyl)-8-(2-(2,2,2-trifluoroethoxy)phenyl)imidazo[1,2-a]pyridine-2-carboxamide;

6-cyano-N-(trans-4-hydroxycyclohexyl)-8-(2-(2,2,2-trifluoroethoxy)phenyl)imidazo[1,2-a]pyridine-2-carboxamide;

N-cis-3-(hydroxymethyl)cyclobutyl)-8-(2-(2,2,2-trifluoroethoxy)phenyl)imidazo[1,2-a]pyridine-2-carboxamide;

6-fluoro-N-(1,1,1-trifluoro-2-methylpropan-2-yl)-8-(2-(2,2,2-trifluoroethoxy)phenyl)imidazo[1,2-a]pyridine-2-carboxamide;

(S)—N-(tetrahydro-2H-pyran-3-yl)-8-(2-(2,2,2-trifluoroethoxy)phenyl)-6-(trifluoromethyl)imidazo[1,2-a]pyridine-2-carboxamide;

6-methoxy-N-(1,1,1-trifluoro-2-methylpropan-2-yl)-8-(2-(2,2,2-trifluoroethoxy)phenyl)imidazo[1,2-a]pyridine-2-carboxamide;

6-cyano-N-(1,1,1-trifluoro-2-methylpropan-2-yl)-8-(2-(2,2,2-trifluoroethoxy)phenyl)imidazo[1,2-a]pyridine-2-carboxamide;

6-chloro-N-((3R,4R)-4-fluorotetrahydrofuran-3-yl)-8-(2-(2,2,2-trifluoroethoxy)phenyl)imidazo[1,2-a]pyridine-2-carboxamide;

6-chloro-N-((3S,4R)-4-fluorotetrahydrofuran-3-yl)-8-(2-(2,2,2-trifluoroethoxy)phenyl)imidazo[1,2-a]pyridine-2-carboxamide;

N-(3-(hydroxymethyl)bicyclo[1.1.1]pentan-1-yl)-8-(2-(2,2,2-trifluoroethoxy)phenyl)imidazo[1,2-a]pyridine-2-carboxamide;

(1-(fluoromethyl)-2-azabicyclo[2.1.1]hexan-2-yl)(8-(2-(2,2,2-trifluoroethoxy)phenyl)imidazo[1,2-a]pyridin-2-yl)methanone;

(2-methyl-5-oxa-2,8-diazaspiro[3.5]nonan-8-yl)(8-(2-(2,2,2-trifluoroethoxy)phenyl)imidazo[1,2-a]pyridin-2-yl)methanone;

(R)-(2,6-dioxa-9-azaspiro[4.5]decan-9-yl)(8-(2-(2,2,2-trifluoroethoxy)phenyl)imidazo[1,2-a]pyridin-2-yl)methanone;

(S)-(2,6-dioxa-9-azaspiro[4.5]decan-9-yl)(8-(2-(2,2,2-trifluoroethoxy)phenyl)imidazo[1,2-a]pyridin-2-yl)methanone;

(2,5-dioxa-8-azaspiro[3.5]nonan-8-yl)(8-(2-(2,2,2-trifluoroethoxy)phenyl)-6-(trifluoromethyl)imidazo[1,2-a]pyridin-2-yl)methanone;

N-(pyridin-2-ylmethyl)-8-(2-(2,2,2-trifluoroethoxy)phenyl)imidazo[1,2-a]pyridine-2-carboxamide;

N-(2,2-dimethyloxetan-3-yl)-8-(2-(2,2,2-trifluoroethoxy)phenyl)imidazo[1,2-a]pyridine-2-carboxamide;

N-methyl-N-(2-(pyrrolidin-1-yl)ethyl)-8-(2-(2,2,2-trifluoroethoxy)phenyl)imidazo[1,2-a]pyridine-2-carboxamide;

(5,6-dihydroimidazo[1,2-a]pyrazin-7(8H)-yl)(8-(2-(2,2,2-trifluoroethoxy)phenyl)imidazo[1,2-a]pyridin-2-yl)methanone;

N-(4-methylpyridin-3-yl)-8-(2-(2,2,2-trifluoroethoxy)phenyl)imidazo[1,2-a]pyridine-2-carboxamide;

N-(4-fluoropyridin-3-yl)-8-(2-(2,2,2-trifluoroethoxy)phenyl)imidazo[1,2-a]pyridine-2-carboxamide;

3-(8-(2-(2,2,2-trifluoroethoxy)phenyl)imidazo[1,2-a]pyridine-2-carboxamido)pyridine 1-oxide;

N-(3-cyanopyridin-4-yl)-8-(2-(2,2,2-trifluoroethoxy)phenyl)imidazo[1,2-a]pyridine-2-carboxamide;

(6-chloro-8-(2-(2,2,2-trifluoroethoxy)phenyl)imidazo[1,2-a]pyridin-2-yl)((1R,5R)-6-(hydroxymethyl)-3-azabicyclo[3.1.0]hexan-3-yl)methanone;

6-fluoro-N-(pyridin-3-yl)-8-(2-(2,2,2-trifluoroethoxy)phenyl)imidazo[1,2-a]pyridine-2-carboxamide;

(8-(2-(2,2,2-trifluoroethoxy)phenyl)-6-(trifluoromethyl)imidazo[1,2-a]pyridin-2-yl)methanol;

(R) 1-(8-(2-(2,2,2-trifluoroethoxy)phenyl)-6-(trifluoromethyl)imidazo[1,2-a]pyridin-2-yl)ethan-1-ol;

(S) 1-(8-(2-(2,2,2-trifluoroethoxy)phenyl)-6-(trifluoromethyl)imidazo[1,2-a]pyridin-2-yl)ethan-1-ol;

1-[6-chloro-8-[2-(2,2,2-trifluoroethoxy)phenyl]imidazo[1,2-a]pyridin-2-yl]ethanol;

[6-chloro-8-[2-(2,2,2-trifluoroethoxy)phenyl]imidazo[1,2-a]pyridin-2-yl]-cyclopropyl-methanol;

2-(6-chloro-8-(2-(2,2,2-trifluoroethoxy)phenyl)imidazo[1,2-a]pyridin-2-yl)propan-2-ol;

2-(6-chloro-8-(4-fluoro-2-(2,2,2-trifluoroethoxy)phenyl)imidazo[1,2-a]pyridin-2-yl) propan-2-ol;

(6-fluoro-8-(2-(2,2,2-trifluoroethoxy)phenyl)imidazo[1,2-a]pyridin-2-yl)(tetrahydro-2H-pyran-4-yl)methanol;

2-(6-chloro-8-(2-(2,2,2-trifluoroethoxy)phenyl)imidazo[1,2-a]pyridin-2-yl)-5,5-dimethyl-4,5-dihydrooxazole;

6-[6-chloro-8-[2-(2,2,2-trifluoroethoxy)phenyl]imidazo[1,2-a]pyridin-2-yl]-2-methyl-5-oxa-2,7-diazaspiro[3.4]oct-6-ene;

(2-(6-chloro-8-(2-(2,2,2-trifluoroethoxy)phenyl)imidazo[1,2-a]pyridin-2-yl)-5-methyl-4,5-dihydrooxazol-5-yl)methanol;

[2-[6-chloro-8-[2-(2,2,2-trifluoroethoxy)phenyl]imidazo[1,2-a]pyridin-2-yl]-4,5-dihydrooxazol-4-yl]methanol;

[2-[6-chloro-8-[2-(2,2,2-trifluoroethoxy)phenyl]imidazo[1,2-a]pyridin-2-yl]-4-methyl-5H-oxazol-4-yl]methanol;

(2-(6-chloro-8-(2-(2,2,2-trifluoroethoxy)phenyl)imidazo[1,2-a]pyridin-2-yl)-4,5-dihydrooxazol-5-yl)methanamine;

2-(2-(6-chloro-8-(2-(2,2,2-trifluoroethoxy)phenyl)imidazo[1,2-a]pyridin-2-yl)-4,5-dihydrooxazol-4-yl)propan-2-ol;

2-[2-[6-chloro-8-[2-(2,2,2-trifluoroethoxy)phenyl]imidazo[1,2-a]pyridin-2-yl]-4,5-dihydrooxazol-5-yl]propan-2-ol;

2-[2-[6-chloro-8-[2-(2,2,2-trifluoroethoxy)phenyl]imidazo[1,2-a]pyridin-2-yl]-5-methyl-4H-oxazol-5-yl]propan-2-ol;

2-[2-[6-chloro-8-[2-(2,2,2-trifluoroethoxy)phenyl]imidazo[1,2-a]pyridin-2-yl]-4-methyl-5H-oxazol-4-yl]propan-2-ol;

2-methyl-N-((8-(2-(2,2,2-trifluoroethoxy)phenyl)imidazo[1,2-a]pyridin-2-yl)methyl)propan-2-amine;

(8-(2-(2,2,2-trifluoroethoxy)phenyl)imidazo[1,2-a]pyridin-2-yl)methanamine;

cis-3-hydroxy-N-(8-(2-(2,2,2-trifluoroethoxy)phenyl)quinolin-2-yl)cyclobutane-1-carboxamide;

trans-3-hydroxy-N-(8-(2-(2,2,2-trifluoroethoxy)phenyl)quinolin-2-yl)cyclobutane-1-carboxamide;

trans-N-(5-fluoro-8-(2-(2,2,2-trifluoroethoxy)phenyl)quinolin-2-yl)-3-hydroxycyclobutane-1-carboxamide; and N-cis-3-hydroxycyclobutyl)-5-(2-(2,2,2-trifluoroethoxy)phenyl)isoquinoline-3-carboxamide.

In yet another embodiment of the invention, includes compounds of Formula Ia

Ia

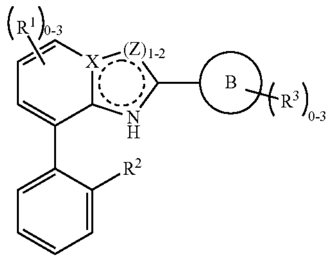

or a pharmaceutically acceptable salt thereof, wherein

X is C or N;

Z is —$CR^4$—, each $R^1$ is independently C1-C4 alkyl, C1-C4 fluoroalkyl, —C0-C4alkylOH, cyano, C1-C4alkoxy, or halo;

each $R^4$ is independently hydrogen, C1-C4 alkyl, C1-C4 fluoroalkyl, —C0-C4alkylOH, cyano, C1-C4alkoxy, or halo;

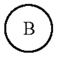

is selected from
(C1-C6 haloalkyl)aminocarbonyl,
(C1-C6 haloalkyl)oxy,
(C1-C6 alkyl)aminocarbonyl,
(C0-C6 alkyl)amino(C1-C4 alkyl),
(C0-C4 alkyl)amino(C1-C4 alkyl)aminocarbonyl,
(C1-C4 haloalkyl)amino(C1-C4 alkyl)aminocarbonyl,
C1-C8alkylOH,
cycloalkylC0-C4 alkyl,
cycloalkylC0-C4 alkylaminocarbonyl,
cycloalkyl(C0-C4 alkyl)carbonyl,
heterocycloalkylC0-C4 alkyl,
heterocycloalkyl(C0-C4 alkyl)aminocarbonyl,
heterocycloalkyl(C0-C4 alkyl)carbonyl,
heteroarylC0-C4 alkyl,
heteroaryl(C0-C4 alkyl)aminocarbonyl,
heteroaryl(C0-C4 alkyl)carbonyl,
arylC0-C4 alkyl,
aryl(C0-C4 alkyl)aminocarbonyl, and
aryl(C0-C4 alkyl)carbonyl;

each $R^2$ is independently selected from halo, (C1-C4 fluoroalkyl)oxy, hydroxy, C1-C4 alkyl, and —(C0-C4 alkyl)O(C1-C4 alkyl); and each $R^3$ is independently selected from C1-C4 alkyl, halo, oxo, cyano, amino, C1-C4 fluoroalkyl, hydroxy, —(C0-C4alkyl)O(C1-C4 alkyl), and Q(C1-C4 alkyl)OH.

It is understood that various embodiments of the invention of compound Formula Ia include those analogous to the first through thirteenth embodiments related to substituent definitions described for Formula I.

Other embodiments of the present invention include the following:

(a) A pharmaceutical composition comprising a compound of Formula I or Formula Ia or a pharmaceutically acceptable salt thereof and a pharmaceutically acceptable carrier.

(b) The pharmaceutical composition of (a), further comprising a second therapeutic agent.

(c) A pharmaceutical combination that is (i) a compound of Formula I or Formula Ia or a pharmaceutically acceptable salt thereof, and (ii) a second therapeutic agent wherein the compound of Formula I or Formula Ia and the second therapeutic agent are each employed in an amount that renders the combination effective for treatment or prophylaxis of lysosomal storage diseases, kidney disease, neurodegenerative disease, diabetes related diseases, or cancers where GSL synthesis is abnormal or overexpression of GCS disrupts ceramide-induced apoptosis.

(d) A compound of Formula I or Formula Ia, or a pharmaceutically acceptable salt thereof, for use in therapy.

(e) A compound of Formula I or Formula Ia, or a pharmaceutically acceptable salt thereof, for use in the treatment of lysosomal storage diseases, kidney disease, neurodegenerative disease, diabetes related diseases, or cancers where GSL synthesis is abnormal or overexpression of GCS disrupts ceramide-induced apoptosis.

(f) A use of a compound of Formula I or Formula Ia or a pharmaceutically acceptable salt thereof, in the preparation of a medicament for modulating glucosylceraide (GlcCer), Glocosylsphingosine (GlcSph) and/or other glucosylceramide-based gycosphingolipids (GSLs) in a subject in need thereof.

(g) A use of a compound of Formula I or Formula Ia or a pharmaceutically acceptable salt thereof, in the preparation of a medicament for treatment or prophylaxis of lysosomal storage diseases, kidney disease, neurodegenerative disease, diabetes related diseases, or cancers where GSL synthesis is abnormal or overexpression of GCS disrupts ceramid-induced apoptosis in a subject in need thereof.

(h) A use of a compound of Formula I or Formula Ia or a pharmaceutically acceptable salt thereof, in the preparation of a medicament for treatment of lysosomal storage diseases, kidney disease, neurodegenerative disease, diabetes related diseases, or cancers where GSL synthesis is abnormal or overexpression of GCS disrupts ceramide-induced apoptosis in a subject in need thereof.

(i) The method of (f), wherein the compound of Formula I or Formula Ia or a pharmaceutically acceptable salt thereof, is administered in combination with an effective amount of at least one second therapeutic agent.

(j) A method of modulating glucosylceramide (GlcCer), Glocosylsphingosine (GlcSph) and/or other glucosylceramide-based gycosphingolipids (GSLs) activity in a subject in need thereof, which comprises administering to the subject the pharmaceutical composition of (a) or (b), or the combination of (c).

(k) A method of treating cognitive impairments associated with cardiometabolic diseases, kidney disease, or diabetes and/or reducing the likelihood or severity of symptoms of cognitive impairments associated with lysosomal storage diseases, kidney disease, neurodegenerative disease, diabetes related diseases, or cancers where GSL synthesis is abnormal or overexpression of GCS disrupts ceramide-induced apoptosis in a subject in need thereof, which comprises administering to the subject the pharmaceutical composition of (a) or (b), or the combination of (c).

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (k) above are understood to include all embodiments of the compounds and/or salts, including such embodiments as result from combinations of embodiments.

Additional embodiments of the invention include the pharmaceutical compositions, combinations, uses and methods set forth in (a) through (k) above, wherein the compound of the present invention employed therein is a compound of one of the embodiments, aspects, classes, sub-classes, or features of the compounds described above. In all of these embodiments, the compound may optionally be used in the form of a pharmaceutically acceptable salt as appropriate.

The present invention also includes a compound of the present invention for use (i) in, (ii) as a medicament for, or (iii) in the preparation of a medicament for: (a) preventing or treating lysosomal storage diseases, kidney disease, neurodegenerative disease, diabetes related diseases, or cancers where GSL synthesis is abnormal or overexpression of GCS disrupts ceramide-induced apoptosis or (c) use in medicine. In these uses, the compounds of the present invention can optionally be employed in combination with one or more second therapeutic agents.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

It is further to be understood that the embodiments of compositions and methods provided as (a) through (k) above are understood to include all embodiments of the compounds, including such embodiments as result from combinations of embodiments.

Examples of lysosomal storage diseases include, but are not limited to, Niemann-Pick type C, Fabry, Tay-Sachs, Sandhoff, Gaucher's disease, and Type 1 Gaucher's disease.

Examples of neurodegenerative diseases, include but are not limited to, Parkinson's disease (PD), dementia with Lewy bodies.

Examples of kidney diseases, include but are not limited to, polycystic kidney disease, renal hypertrophy.

Examples of diabetes related diseases, include but are not limited to, diabetes mellitus, obesity, hyperglycemia and hyperinsulemia.

Examples of cancers where GSL synthesis is abnormal or overexpression of GCS disrupts ceramide-induced apoptosis include leukemia, papillary renal, and thyroid carcinomas.

The present invention also relates to processes for the preparation of the compounds of Formula I or Formula Ia which are described in the following and by which the compounds of the invention are obtainable.

Exemplifying the invention is the use of the compounds disclosed in the Examples and herein.

The invention also relates to the use of compounds of the invention for the preparation of a medicament for the treatment and/or prophylaxis of the above-mentioned diseases.

The compounds of the Formula I or Formula Ia and their physiologically acceptable salts can be administered to animals, preferably to mammals, and in particular to humans, as pharmaceuticals by themselves, in mixtures with one another or in the form of pharmaceutical preparations. A subject of the present invention therefore also are the compounds of the Formula I or Formula Ia and their physiologically acceptable salts for use as pharmaceuticals, their use for modulating glycosphingolipids (GSLs), for normalizing an elevated GSLs level and in particular their use in the therapy and prophylaxis of the abovementioned syndromes as well as their use for preparing medicaments for these purposes.

Furthermore, a subject of the present invention is pharmaceutical preparations (or pharmaceutical compositions) which comprise as active component an effective dose of at least one compound of the Formula I or Formula Ia and/or a physiologically acceptable salt thereof and a customary pharmaceutically acceptable carrier, i.e., one or more pharmaceutically acceptable carrier substances and/or additives.

Thus, a subject of the invention is, for example, said compound and its physiologically acceptable salts for use as a pharmaceutical, pharmaceutical preparations which comprise as active component an effective dose of said compound and/or a physiologically acceptable salt thereof and a customary pharmaceutically acceptable carrier, and the uses of said compound and/or a physiologically acceptable salt thereof in the therapy or prophylaxis of the abovementioned syndromes as well as their use for preparing medicaments for these purposes.

As noted above, additional embodiments of the present invention are each directed to a method for the treatment a disease, disorder, or condition, or one or more symptoms thereof ("indications") in which glucosylceramide synthase (GCS) is involved and for which the inhibition of GCS is desired, which method comprises administering to a subject in need of such treatment a therapeutically effective amount of a compound of the invention, or a pharmaceutically acceptable salt thereof, or a pharmaceutical composition comprising said compound or salt thereof.

In another embodiment, the present invention is directed to a method for the manufacture of a medicament for inhibition of GCS activity in a subject comprising combining a compound of the present invention, or a pharmaceutically acceptable salt thereof, with a pharmaceutical carrier or diluent.

One such embodiment provides a method of treating Parkinson's disease in a subject in need thereof, said method comprising administering to a subject in need of such treatment a therapeutically effective amount of a compound of the invention, or a pharmaceutically acceptable salt thereof, or a pharmaceutical composition comprising said compound or salt thereof. In one such embodiment, the subject is a human.

Another embodiment provides a method for the treatment or prophylaxis of neurologic damage associated with Parkinson's disease in a subject in need thereof. Another embodiment provides a method of treating or improving dopaminergic tone to provide symptomatic relief in a subject in need thereof, for example, in treating, alleviating, ameliorating, or managing motor and non-motor symptoms of Parkinson's disease.

Another embodiment provides a method for the treatment or prophylaxis of abnormal motor symptoms associated with Parkinson's disease (including but not limited to bradykinesia, rigidity and resting tremor). Another embodiment provides a method for the treatment or prophylaxis of abnormal non-motor symptoms associated with Parkinson's disease (including but not limited to cognitive dysfunction, autonomic dysfunction, emotional changes and sleep disruption); Lewy body dementia; and L-Dopa induced dyskinesias. Each said method independently comprises administering to a patient in need of such treatment an effective amount of a compound of the invention, or a pharmaceutically acceptable salt thereof, or pharmaceutically acceptable composition thereof.

Non-limiting examples of additional indications in which GCS is involved and in which the treatment or prophylaxis of said indications in a subject in need thereof are contemplated include the following, each of which, alone or in combination, comprise additional embodiments of the invention: Alzheimer's disease, mild cognitive impairment, the transition from mild cognitive impairment to Alzheimer's disease, tauopathy disorders characterized by hyperphosphorylation of tau such as argyrophilic grain disease, Picks disease, corticobasal degeneration, progressive supranuclear palsy, inherited frontotemporal dementia, and Parkinson's disease linked to chromosome 17.

Additional indications include neuroinflammation, including neuroinflammation associated with of microglial inflammatory responses associated with multiple sclerosis, HIV-induced dementia, memential with Lewy bodies, ALS, ischemic stroke, traumatic brain injury and spinal cord injury.

Additional indications include diseases of the immune system including lymphomas, leukemias, multiple sclerosis, rheumatoid arthritis, systemic lupus erythematosus, autoimmune hemolytic anemia, pure red cell aplasia, idiopathic thrombocytopenic pupura (ITP), Evans Syndrome, vasculitis, bullous skin disorder, type I diabetes mellitus, Sjogren's syndrome, Delvic's disease, inflammatory myopathies, and ankylosing spondylitis.

Additional indications include papillary renal and thyroid carcinomas in a subject in whom glucoxylceramide (GlcCer), Glucosylsphingosine (GlcSph) and/or other glucosylceramide-based glycosphingolipids (GSLs) are amplified or elevated. Diseases associated with elevated GSL levels include polycystic kidney disease, renal hypertrophy, diabetic nephropathy, diabetes mellitus, obesity, hyperglycemia, and hyperinsulemia.

The compounds of the present invention may be useful in treatment of cancers where GSL synthesis is abnormal or overexpression of GCS disrupts ceramid-induced apoptosis.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

One or more additional pharmacologically active agents may be administered in combination with a compound of Formula I or Formula Ia (or a pharmaceutically acceptable salt thereof). An additional active agent (or agents) is intended to mean a pharmaceutically active agent (or agents) that is active in the body, including pro-drugs that convert to pharmaceutically active form after administration, which are different from the compound of Formula I or Formula Ia. The additional active agents also include free-acid, free-base and pharmaceutically acceptable salts of said additional active agents. Generally, any suitable additional active agent or agents, including chemotherapeutic agents or therapeutic antibodies, may be used in any combination with the compound of Formula I or Formula Ia in a single dosage formulation (e.g., a fixed dose drug combination), or in one or more separate dosage formulations which allows for concurrent or sequential administration of the active agents (co-administration of the separate active agents) to subjects. In addition, the compounds of Formula I or Formula Ia (or pharmaceutically acceptable salts thereof) can be administered in combination with radiation therapy, hormone therapy, surgery or immunotherapy.

The compounds of the present invention may be used in combination with one or more other drugs in the treatment, prevention, control, amelioration, or reduction of risk of diseases or conditions for which compounds of the invention or the other drugs may have utility, where the combination of the drugs together are safer or more effective than either drug alone. Such other drug(s) may be administered, by a route and in an amount commonly used therefore, contemporaneously or sequentially with a compound of Formula I or Formula Ia. When a compound of Formula I or Formula Ia is used contemporaneously with one or more other drugs, a pharmaceutical composition in unit dosage form containing such other drugs and the compound of Formula I or Formula Ia is preferred. However, the combination therapy may also include therapies in which the compound of Formula I or Formula Ia and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I or Formula Ia.

For example, the present compounds may be used in conjunction with one or more additional therapeutic agents, for example: L-DOPA, PD-1 (programmed cell death protein 1) and PDL-1 (programmed death-ligand 1) antagonists, Leucine-rich repeat kinase 2 (LRRK2) inhibitors, dopaminergic agonists such as quinpirole, ropinirole, pramipexole, pergolide and bromocriptine; MAO-B inhibitors such as rasagiline, deprenyl and selegiline; DOPA decarboxylase inhibitors such as carbidopa and benserazide; and COMT inhibitors such as tolcapone and entacapone; or potential therapies such as an adenosine A2a antagonists, metabotropic glutamate receptor 4 modulators, or growth factors such as brain derived neurotrophic factor (BDNF), and a pharmaceutically acceptable carrier.

Non-limiting examples of LRRK2 inhibitors include: DNL201 and DNL151 (Denali Therapeutics Inc.), LRRK2-IN-1, CZC-54252, CZC25146, TTT-3002, HG-10-102-1, JH-II-127, GSK2578215A, GNE-7915, GNE0877, GNE-9605, PF-06447475, MLi-2, and PF-06685360 (also known as PFE-360). Additional examples include the LRRK2 inhibitors disclosed in U.S. Pat. No. 9,233,977, WO2016/036586, U.S. Pat. Nos. 9,416,126, 9,493,440, 9,688,654, 9,440,952, 9,718,818, 9,809,568, WO2019/074810, WO2019/074809, and WO2020/092136.

The invention further relates to a method of treating cancer in a human patient comprising administration of a compound of the invention (i.e., a compound of Formulae I and Ia) and a PD-1 antagonist to the patient. The compound of the invention and the PD-1 antagonist may be administered concurrently or sequentially.

In particular embodiments, the PD-1 antagonist is an anti-PD-1 antibody, or antigen binding fragment thereof. In alternative embodiments, the PD-1 antagonist is an anti-PD-L1 antibody, or antigen binding fragment thereof. In some embodiments, the PD-1 antagonist is pembrolizumab (KEYTRUDA™, Merck & Co., Inc., Kenilworth, NJ, USA), nivolumab (OPDIVO™, Bristol-Myers Squibb Company, Princeton, NJ, USA), cemiplimab (LIBTAYO™, Regeneron Pharmaceuticals, Inc., Tarrytown, NY, USA), atezolizumab (TECENTRIQ™, Genentech, San Francisco, CA, USA), durvalumab (IMFINZI™, AstraZeneca Pharmaceuticals LP, Wilmington, DE), or avelumab (BAVENCIO™, Merck KGaA, Darmstadt, Germany).

In some embodiments, the PD-1 antagonist is pembrolizumab. In particular sub-embodiments, the method comprises administering 200 mg of pembrolizumab to the patient about every three weeks. In other sub-embodiments, the method comprises administering 400 mg of pembrolizumab to the patient about every six weeks.

In further sub-embodiments, the method comprises administering 2 mg/kg of pembrolizumab to the patient about every three weeks. In particular sub-embodiments, the patient is a pediatric patient.

In some embodiments, the PD-1 antagonist is nivolumab. In particular sub-embodiments, the method comprises administering 240 mg of nivolumab to the patient about every two weeks. In other sub-embodiments, the method comprises administering 480 mg of nivolumab to the patient about every four weeks.

In some embodiments, the PD-1 antagonist is cemiplimab. In particular embodiments, the method comprises administering 350 mg of cemiplimab to the patient about every 3 weeks.

In some embodiments, the PD-1 antagonist is atezolizumab. In particular sub-embodiments, the method comprises administering 1200 mg of atezolizumab to the patient about every three weeks.

In some embodiments, the PD-1 antagonist is durvalumab. In particular sub-embodiments, the method comprises administering 10 mg/kg of durvalumab to the patient about every two weeks.

In some embodiments, the PD-1 antagonist is avelumab. In particular sub-embodiments, the method comprises administering 800 mg of avelumab to the patient about every two weeks.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, buccal or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term “composition” is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated, or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanthin and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanthin, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above-mentioned pathological conditions.

In the treatment, prevention, control, amelioration, or reduction of risk of conditions which require inhibition of GCS activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day or may be administered once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In one aspect, the present invention provides a kit comprising a therapeutically effective amount of at least one Compound of Formula I or Formula Ia, or a pharmaceutically acceptable salt or prodrug of said compound and a pharmaceutically acceptable carrier, vehicle or diluent.

In another aspect the present invention provides a kit comprising an amount of at least one Compound of Formula I or Formula Ia, or a pharmaceutically acceptable salt or prodrug of said compound and an amount of at least one additional therapeutic agent listed above, wherein the amounts of the two or more active ingredients result in a desired therapeutic effect. In one embodiment, the one or more Compounds of Formula I or Formula Ia and the one or more additional therapeutic agents are provided in the same container. In one embodiment, the one or more Compounds of Formula I or Formula Ia and the one or more additional therapeutic agents are provided in separate containers.

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "haloalkyl," "—O-alkyl," etc.

As used herein, the term "administration" and variants thereof (e.g., "administering" a compound) in reference to a compound of the invention means providing the compound to the individual in need of treatment. When a compound of the invention is provided in combination with one or more other active agents (e.g., L-DOPA), "administration" and its variants are each understood to include concurrent and sequential administration of the compound or salt and other agents.

A "subject" (alternatively referred to herein as "patient") is a human or non-human mammal. In one embodiment, a subject is a human. In another embodiment, a subject is a primate. In another embodiment, a subject is a monkey. In another embodiment, a subject is a chimpanzee. In still another embodiment, a subject is a rhesus monkey.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of one or more symptoms of the disease or condition being treated. In another embodiment, the effective amount is a "prophylactically effective amount" for reduction of the severity or likelihood of one or more symptoms of the disease or condition. The term also includes herein the amount of active compound sufficient to modulate GSC activity and thereby elicit the response being sought (i.e., a "therapeutically effective amount"). When the active compound (i.e., active ingredient) is administered as the salt, references to the amount of active ingredient are to the free acid or free base form of the compound.

The terms "treating" or "treatment" as used herein with respect to lysosomal storage diseases, neurodegenerative disease, cystic disease, cancer, or a diseases or disorders associated with elevated levels of glucosylceramide (GlcCer), glucosylsphingosine (GlcSph) and/or other glucosylceramide-based glycosphingolipids (GSLs), includes inhibiting the severity of the diseases i.e., arresting or reducing the development of the diseases or its clinical symptoms; or relieving the diseases, i.e., causing regression of the severity of the diseases or their clinical symptoms.

The terms "preventing," or "prophylaxis," as used herein with respect to the cardiometabolic diseases including high blood pressure, heart failure, kidney disease, and diabetes, refers to reducing the likelihood or severity of the diseases.

The term "$C_0$" or "C0" as employed in expressions such as "$C_{0-6}$ alkyl" and C0 6alkyl" means a direct covalent bond; or when the term appears at the terminus of a substituent, $C_{0-6}$ alkyl means hydrogen or $C_{1-6}$alkyl. Similarly, when an integer defining the presence of a certain number of atoms in a group is equal to zero, it means that the atoms adjacent thereto are connected directly by a bond. For example, in the structure

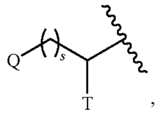

, wherein s is an integer equal to zero, 1 or 2, the structure is

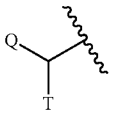

when s is zero.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched. Unless otherwise indicated, an alkyl group is unsubstituted.

The term "carbonyl" means a functional group composed of a carbon atom double-bonded to an oxygen atom, C═O.

"Cycloalkyl" or "$C_{3-12}$ cycloalkyl" means any univalent radical derived from a monocyclic or bicyclic ring system having 3 to 12 ring carbons atoms; said ring system may be (a) a $C_3$ to a $C_5$ monocyclic, saturated ring or not fully aromatic ring, or (b) a bicyclic saturated or not fully aromatic ring system. Here, the point of attachment for a "cycloalkyl" to the rest of the molecule is on the saturated ring. Bicyclic cycloalkyl ring systems include fused ring systems, where two rings share two atoms (e.g. decalin), spiro ring systems where two rings share one atom (e.g. spiro[4.5]decanyl) and bridge groups (e.g., norbornane).

Additional examples within the above meaning include, but are not limited to univalent radicals of cyclopropyl, cyclobutyl, cyclopentyl, cyclohexyl, cycloheptyl, bicyclo [2.2.2]octanyl, bicyclo[1.1.1]pentanyl, bicyclo[2.2.1]heptanyl, [1.1.1]-bicyclo pentane, 1-decalinyl, spiro[2.4]heptyl, spiro[2.2]pentyl, 2,3-dihydro-1H-indenyl, and norbornyl.

The term "$C_{3-8}$ cycloalkyl" (or "$C_3$-$C_5$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "heteroalkyl" refers to an alkyl group where 1, 2, or 3 of the carbon atoms is substituted by a heteroatom independently chosen from N, O, or S.

The term "alkoxy" refers to an alkyl (carbon and hydrogen chain) group singularly bonded to oxygen (R—O). Non-limiting examples of alkoxy are methoxy ($CH_3$ O—), ethoxy ($CH_3$ $CH_2$ O—) and butoxy ($CH_3$ $CH_2$ $CH_2$ O—).

"Aryl" means a monocyclic, bicyclic or tricyclic carbocyclic aromatic ring or ring system containing 5-14 carbon atoms, wherein at least one of the rings is aromatic.

Examples of aryl include phenyl and naphthyl. In one embodiment of the present invention, aryl is phenyl.

The term “fluoroalkyl” means an alkyl group in which one or more fluorines, for example 1 to 6 fluorines, have been substituted for hydrogen.

The term “halogen” or “halo” includes fluorine, chlorine, bromine, and iodine.

“Haloalkyl” refers to an alkyl group as described above wherein one or more (in particular 1 to 5) hydrogen atoms have been replaced by halogen atoms, with up to complete substitution of all hydrogen atoms with halo groups. $C_{1-6}$ haloalkyl, for example, includes $—CF_3$, $—CF_2CF_3$, $—CHFCH_3$, and the like.

The term “heteroaryl”, as used herein, represents a stable monocyclic, bicyclic or tricyclic ring system containing 5-14 carbon atoms and containing at least one ring heteroatom selected from N, S (including SO and $SO_2$) and O, wherein at least one of the heteroatom containing rings is aromatic. In the case of a heteroaryl ring system where one or more of the rings are saturated and contain one or more N atoms, the N can be in the form of quaternary amine. Bicyclic heteroaryl ring systems include fused ring systems, where two rings share two atoms, and spiro ring systems, where two rings share one atom. Heteroaryl groups within the scope of this definition include but are not limited to: azaindolyl, benzoimidazolyl, benzisoxazolyl, benzofuranyl, benzofurazanyl, benzopyrazolyl, benzotriazolyl, benzothiophenyl, benzothiazolyl, benzo[d]isothiazole, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyrrolyl, pyrazolopyrimidinyl, pyridazinyl, pyridyl, pyrimidyl, pyrimidinyl, pyrrolyl, quinazolinyl, quinolyl, quinoxalinyl, tetrazolyl, tetrazolopyridyl, thiadiazolyl, 5H-pyrrolo[3,4-b]pyridine, thiazolyl, thienyl, triazolyl, triazinyl, benzothiazolyl, benzothienyl, quinolinyl, quinazolinyl, and isoquinolinyl, and oxazolyl. If the heteroaryl contains nitrogen atoms, it is understood that the corresponding N-oxides thereof are also encompassed by this definition.

The term “heterocycloalkyl” as used herein refers to a stable saturated or not fully aromatic 3- to 18-membered ring (i.e., C3-C18 heterocycloalkyl) radical that comprises two to twelve ring carbon atoms and from one to six ring heteroatoms selected from nitrogen, oxygen and sulfur. Whenever it appears herein, a numerical range such as “3 to 18” refers to each integer in the given range; e.g., “3 to 18 ring atoms” means that the heterocycloalkyl group may consist of 3 ring atoms, 4 ring atoms, 5 ring atoms, etc., up to and including 18 ring atoms. In one embodiment, a heterocycloalkyl group is monocyclic and has from about 3 to about 7 ring atoms. In another embodiment, a heterocycloalkyl group is monocyclic has from about 5 to about 8 ring atoms. In another embodiment, a heterocycloalkyl group is bicyclic and has from about 8 to about 11 ring atoms. In still another embodiment, a heterocycloalkyl group is monocyclic and has 5 or 6 ring atoms. There are no adjacent oxygen and/or sulfur atoms present in the ring system. Unless stated otherwise specifically in the specification, the heterocycloalkyl radical may be a monocyclic, bicyclic, tricyclic or tetracyclic ring system, which may include fused or bridged ring systems. The heteroatoms, e.g. sulfur, in the heterocycloalkyl radical may be optionally oxidized. One or more nitrogen atoms, if present, are optionally quaternized. The heterocycloalkyl radical is partially or fully saturated. The heterocycloalkyl may be attached to the rest of a molecule through any atom of the ring(s).

Examples of such heterocycloalkyl radicals include, but are not limited to, 6,7-dihydro-5H-cyclopenta[b]pyridine, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, I-oxo-thiomorpholinyl, decahydroisoquinoline, 1,4-dioxaspiro[4.5]decane, 2,5-diazabicyclo[2.2.1]heptyl, dioxa-9-azospiro[4.5]decanyl, 5,7-dihydro-6H-pyrrolo[3,4-b]pyridinyl, 4,5-dihydrooxazolyl, oxa-2,8-diazaspiro[3.5]nonanyl, dioxaazaspiro[3.5]nonanyl, 5,6-dihydroimidazo[1,2-a]pyrazinyl, azabicyclo[3.1.0]hexanyl, 2,7diazaspiro[3.4]octenyl, 1,1-dioxothiomorpholinyl, oxetanyl, oxetenyl, 1,4-dioxanyl, tetrahydrothiophenyl, beta lactam, gamma lactam, delta lactam, beta lactone, gamma lactone, delta lactone, and pyrrolidinone, and oxides thereof and all isomers thereof.

“Oxo” means an oxygen atom connected to another atom by a double bond and is represented by “=O” herein.

By “pharmaceutically acceptable” is meant that the ingredients of the pharmaceutical composition must be compatible with each other and not deleterious to the recipient thereof.

Where any amine is present in the compound, the N atom may be optionally in the form of a quaternary amine having one or more appropriate additional substitutions, as further described herein.

When any variable (e.g., n, $R^a$, $R^b$, etc.) occurs more than one time in any constituent or in Formula I or Formula Ia, its definition on each occurrence is independent of its definition at every other occurrence. Also, combinations of substituents and/or variables are permissible only if such combinations result in stable compounds.

When any ring atom is specified as being optionally substituted with, or in a specified form, for example, S substituted with oxo groups, or N in the form of a N-oxide, this does not preclude the substitution of any ring atom with the other listed optional substituents when not substituted with oxo groups or in the form of a N-oxide.

“Celite®” (Fluka) diatomite is diatomaceous earth, and can be referred to as “celite”.

The term “substituted” means that one or more hydrogens on the designated atom is replaced with a selection from the indicated group, provided that the designated atom’s normal valency under the existing circumstances is not exceeded, and that the substitution results in a stable compound. Combinations of substituents and/or variables are permissible only if such combinations result in stable compounds.

By “stable compound” or “stable structure” is meant a compound that is sufficiently robust to survive isolation to a useful degree of purity from a reaction mixture, and formulation into an efficacious therapeutic agent. The compounds of the present invention are limited to stable compounds embraced by Formula I or Ia.

The term “compound” refers to the compound and, in certain embodiments, to the extent they are stable, any hydrate or solvate thereof. A hydrate is the compound complexed with water, and a solvate is the compound complexed with an organic solvent.

The term “in substantially purified form,” as used herein, refers to the physical state of a compound after the compound is isolated from a synthetic process (e.g., from a reaction mixture), a natural source, or a combination thereof. The term “in substantially purified form,” also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed “protected”, this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

Lines drawn into the ring systems from substituents indicate that the indicated bond can be attached to any of the substitutable ring atoms. If the ring system is polycyclic, it is intended that the bond be attached to any of the suitable carbon atoms on the proximal ring only.

Under standard nomenclature used throughout this disclosure, the terminal portion of the designated side chain is preceded by the adjacent functionality toward the point of attachment. For example, a C1-5 alkylcarbonylamino C1-6 alkyl substituent is equivalent to

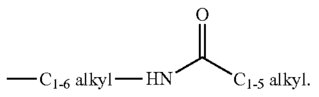

Structural representations of compounds having substituents terminating with a methyl group may display the terminal methyl group either using the characters “CH3”, e.g. “—CH3” or using a straight line representing the presence of the methyl group, e.g., “——” i.e., “⌇—— $CH_3$” and “⌇—— ” have equivalent meanings.

For variable definitions containing terms having repeated terms, e.g., (CRiRj)r, where r is the integer 2, Ri is a defined variable, and Rj is a defined variable, the value of Ri may differ in each instance in which it occurs, and the value of Rj may differ in each instance in which it occurs. For example, if Ri and Rj are independently selected from the group consisting of methyl, ethyl, propyl and butyl, then (CRiRj)2 can be

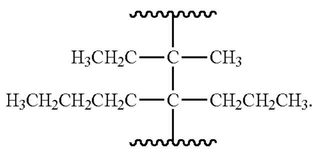

Unless expressly stated to the contrary, all ranges cited herein are inclusive. For example, a heteroaromatic ring described as containing from “1 to 4 heteroatoms” means the ring can contain, 1, 2, 3 or r heteroatoms. It is also to be understood that any range cited herein includes within its scope all of the sub-ranges within that range. Thus, for example, a heterocyclic ring described as containing from “1 to 4 heteroatoms” is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. Similarly, $C_1$-$C_6$ when used with a chain, for example an alkyl chains means that the chain can contain 1, 2, 3, 4, 5, or 6 carbon atoms. It also includes all ranges contained therein including $C_1$-$C_5$, $C_1$-$C_4$, $C_1$-$C_3$, $C_1$-$C_2$, $C_2$-$C_6$, $C_3$-$C_6$, $C_4$-$C_6$, $C_5$-$C_6$, and all other possible combinations.

In choosing compounds of the present invention, one of ordinary skill in the art will recognize that the various substituents, i.e. $R^1$, $R^A$, etc., are to be chosen in conformity with well-known principles of chemical structure connectivity and stability.

As used herein, the term “composition” is intended to encompass a product comprising the specified ingredients in the specified amounts, as well as any product which results from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term “prodrug” means a compound (e.g., a drug precursor) that is transformed in vivo to provide a compound of Formula I or Formula Ia or a pharmaceutically acceptable salt of the compound. The transformation may occur by various mechanisms (e.g., by metabolic or chemical processes), such as, for example, through hydrolysis in blood. For example, if a compound of Formula I or Formula Ia or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$C_3$)alkyl, and the like.

Similarly, if a compound of Formula I or Formula Ia contains an alcohol functional group, a prodrug can be formed by the replacement of one or more of the hydrogen atoms of the alcohol groups with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$) alkoxycarbonyloxymethyl, N—($C_1$-$C_6$)alkoxycarbonylaminomethyl, succinoyl, ($C_1$-$C_6$)alkanoyl, α-amino($C_1$-$C_4$) alkyl, α-amino($C_1$-$C_4$)alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate).

If a compound of Formula I or Formula Ia incorporates an amine functional group, a prodrug can be formed by the replacement of a hydrogen atom in the amine group with a group such as, for example, R-carbonyl-, RO-carbonyl-, NRR'-carbonyl- wherein R and R' are each independently $(C_1-C_{10})$alkyl, $(C^3-C^7)$ cycloalkyl, benzyl, a natural α aminoacyl, —C(OH)C(O)O$Y^1$ wherein $Y^1$ is H, $(C_1-C_6)$alkyl or benzyl, —C(O$Y^2$)$Y^3$ wherein $Y^2$ is $(C_1-C_4)$ alkyl and $Y^3$ is $(C_1-C_6)$alkyl; carboxy $(C_1-C_6)$alkyl; amino$(C_1-C_4)$alkyl or mono-N- or di-N,N—$(C_1-C_6)$alkylaminoalkyl; —C($Y^4$)$Y^5$ wherein $Y^4$ is H or methyl and $Y^5$ is mono-N- or di-N,N—$(C_1-C_6)$alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$ alkyl, —O—($C_{1-4}$ alkyl) or amino); (2) sulfonate esters, such as alkyl- or aralkylsulfonyl (for example, methanesulfonyl); (3) amino acid esters, including those corresponding to both natural and non-natural amino acids (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.,* 93(3), 601-611 (2004) describe the preparation of the solvates of the antifungal fluconazole in ethyl acetate as well as from water. Similar preparations of solvates, hemisolvates, hydrates and the like are described by E. C. van Tonder et al, *AAPS PharmSciTech.,* 5(1), article 12 (2004); and A. L. Bingham et al, *Chem. Commun.,* 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The compound of Formula I or Formula Ia can form salts which are also within the scope of this invention. Reference to a compound of Formula I or Formula Ia herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I or Formula Ia contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula I or Formula Ia may be formed, for example, by reacting a compound of Formula I or Formula Ia with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), arylalkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the compound of Formula I or Formula Ia may be atropisomers (e.g., substituted biaryls) and are considered as part of this invention. Enantiomers can also be directly separated using chiral chromatographic techniques.

It is also possible that the compound of Formula I or Formula Ia may exist in different tautomeric forms, and all such forms are embraced within the scope of the invention. For example, all keto-enol and imine-enamine forms of the compounds are included in the invention.

Unless otherwise indicated, all stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a compound of Formula I or Formula Ia incorporates a double bond or a fused ring, both the cis- and trans-forms, as well as mixtures, are embraced within the scope of the invention.

When a substituent on a chiral carbon atom is depicted without specific stereochemistry (by using a straight line bond to a chiral center), it is to be understood that both the alpha and beta configurations of said substituent group are to be considered part of the present invention. For example, the compound of the present invention, which is drawn as follows:

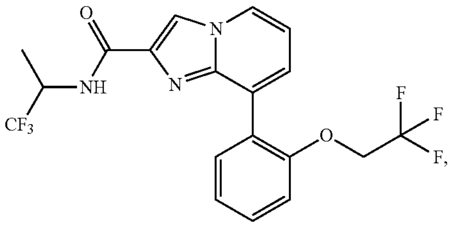

is understood to encompass both stereoisomers at the indicated chiral center located at the carbon atom attached to the carboxamide portion of the compound, the structures of which are as follows:

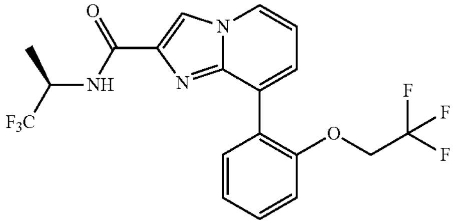

and

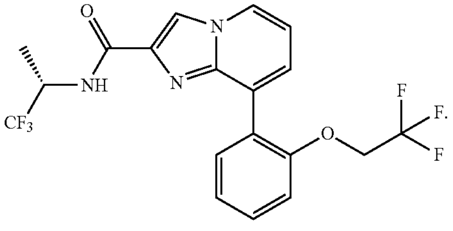 [SMILES: CC(NC(=O)c1cn2cccc(-c3ccccc3OCC(F)(F)F)c2n1)C(F)(F)F]

In the Examples section below, compounds of the present invention that have been purified as individual stereoisomers are sometimes depicted in non-stereospecific form but identified using one or more of the terms: "diastereomer 1," "diastereomer 2," "isomer 1," "isomer 2," "first eluding enantiomer", "enantiomer A" and "enantiomer B." In this instance, the absolute stereochemistry of each isolated diastereomer and enantiomeric center has not been determined and the terms used above are used to represent each individual purified stereochemically pure compound.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

In the Compounds of Formula I or Formula Ia, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I or Formula Ia. For example, different isotopic forms of hydrogen (H) include protium ($^1H$) and deuterium ($^2H$). Protium is the predominant hydrogen isotope found in nature. Enriching for deuterium may provide certain therapeutic advantages, such as increasing in vivo half-life or reducing dosage requirements, or may provide a compound useful as a standard for characterization of biological samples. Isotopically-enriched Compounds of Formula I or Formula Ia can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula I or Formula Ia has one or more of its hydrogen atoms replaced with deuterium.

In another embodiment, the Compounds of Formula I or Formula Ia are in substantially purified form.

Methods of Synthesis

General Procedures

The compounds of the present invention can be prepared according to the following general schemes and specific examples, or modifications thereof, using readily available starting materials, reagents and conventional synthetic procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following schemes.

Unless otherwise specifically indicated, all reagents are commercially available, known in the literature, or readily synthesized by one skilled in the art. The general route applied to the synthesis of compounds of Formula I and Formula Ia is described in the Schemes that follow. In some instances, the order of carrying out the reaction steps in the schemes may be varied to facilitate the reaction or to avoid unwanted reaction products. Additionally, various protecting group strategies familiar to one skilled in the art of organic synthesis may be employed to facilitate the reaction or to avoid unwanted reaction products.

In some cases, the final product may be further modified, for example, by manipulation of substituents. These manipulations may include, but are not limited to, reduction, oxidation, alkylation, acylation, and hydrolysis reactions which are commonly known to those skilled in the art.

Reactions sensitive to moisture or air were performed under nitrogen or argon using anhydrous solvents and reagents. The progress of reactions was determined by either analytical thin layer chromatography (TLC) usually performed with E. Merck pre-coated TLC plates, silica gel 60F-254, layer thickness 0.25 mm or liquid chromatography-mass spectrometry (LC/MS).

The following examples are provided so that the invention might be more fully understood. These examples are illustrative only and should not be construed as limiting the invention in any way. Wherein a racemic mixture is produced, the enantiomers may be separated using SFC reverse or normal phase chiral resolution conditions either after isolation of the final product or at a suitable Intermediate, followed by processing of the single isomers individually. It is understood that alternative methodologies may also be employed in the synthesis of these key intermediates and examples. Asymmetric methodologies (e.g. chiral catalysis, auxiliaries) may be used where possible and appropriate. The exact choice of reagents, solvents, temperatures, and other reaction conditions, depends upon the nature of the intended product.

The following abbreviations are used throughout the text:

Me: methyl
Et: ethyl
Bu: butyl
t-Bu: tert-butyl
Ar: aryl
Ph: phenyl
Bn: benzyl
Ac: acetyl
i-Pr: isopropyl
Py: pyridyl
OAc: acetate
DBU: 1,8-diazabicyclo[5.4.0]undec-7-ene
DIBAL: diisobutylaluminum hydride
DMSO: dimethylsulfoxide
DMF: N,N-dimethylformamide
m-CPBA: 3-chloroperbenzoic acid
PyBop: benzotriazol-1-yl-oxytripyrrolidinophosphonium hexafluorophosphate
XPhos: 2-Dicyclohexylphosphino-2',4',6'-triisopropylbiphenyl
THF: tetrahydrofuran
TEA: triethylamine
DCE: 1,2-dichloroethane
DCM: dichloromethane
PE: petroleum ether
aq: aqueous
HPLC: high performance liquid chromatography
MS: mass spectrometry
LCMS: liquid chromatography-mass spectrometry
SFC: supercritical fluid chromatography
NMR: nuclear magnetic resonance
MHz: megahertz
° C.: degrees Celsius
ATP: adenosine triphosphate
UDP: uridine diphosphate
GCS: glucosylceramide synthase
TFA: trifluoroacetic acid
TLC: thin layer chromatography
Boc: tert-butoxycarbonyl
$Boc_2O$: di-tert-butyl dicarbonate
DIEA: N,N-diisopropylethylamine
DIPEA: N,N-diisopropylethylamine
EDC: N-(3-dimethylaminopropyl)-N'-ethylcarbodiimide hydrochloride
EDCI: N-(3-dimethylaminopropyl)-N'-ethylcarbodiimide hydrochloride
HATU: O-(7-azabenzotriazol-1-yl)-N,N,N'N'-tetramethyluronium hexafluorophosphate
min: minutes
h: hours
nm: nonometers
mm: millimeters
cm: centimeters
□l: microliters
ml: milliliters
□g: micrograms
mg: milligrams
nM: nanomolar
mmol: millimoles
□M: micromolar
N: normal
M: molar
MS: mass spectrometry
dtbpf: 1,1'-bis(di-tert-butylphosphino)ferrocene
HOAt: 1-hydroxy-7-azabenzotriazole
LAH: lithium aluminum hydride
TMSI trimethylsilyl iodide (iodotrimethylsilane)
NPA: n-propyl acetate
Conc: concentrated
OTf: trifluoromethanesulfonate
HEPES: 4-(2-hydroxyethyl)-1-piperazineethanesulfonic acid
DOPC: 1,2-Dioleoyl-sn-glycero-3-phosphocholine

Reaction Schemes

The compounds of the present invention can be prepared readily according to the following Schemes and specific examples, or modifications thereof, using readily available starting materials, reagents and conventional synthetic procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

As illustrated in Scheme A, in general, intermediate imidazopyridines of structure A-2 may be prepared by the procedure provided in "Preparation and New Reaction s of Imidazo[1,2-a]pyridines" (Lombardino, *J. Org. Chem.* 1965, 30, 7, 2403-2407). The appropriately substituted compound of A-1 can be treated with ethyl 3-bromo-2-oxopropanoate at elevated temperature to yield compounds of the formula A-2.

Scheme A

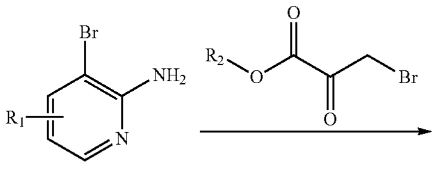

A-1

-continued

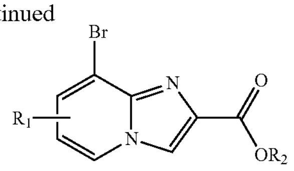

A-2

As illustrated in Scheme B, in general, compounds of the invention can be prepared by palladium-catalyzed Suzuki reaction between an appropriately functionalized boronic ester or acid and intermediate A-2 described in Scheme A to yield compounds of the formula B-1. Intermediate B-1 can then be hydrolyzed by treatment with a base such as lithium hydroxide or sodium hydroxide to yield the intermediate carboxylate B-2, which may be used to form an amide bond with a primary or secondary amine in the presence of a coupling reagent such as EDC or HATU to yield compounds of the present invention as formula (I).

Scheme B

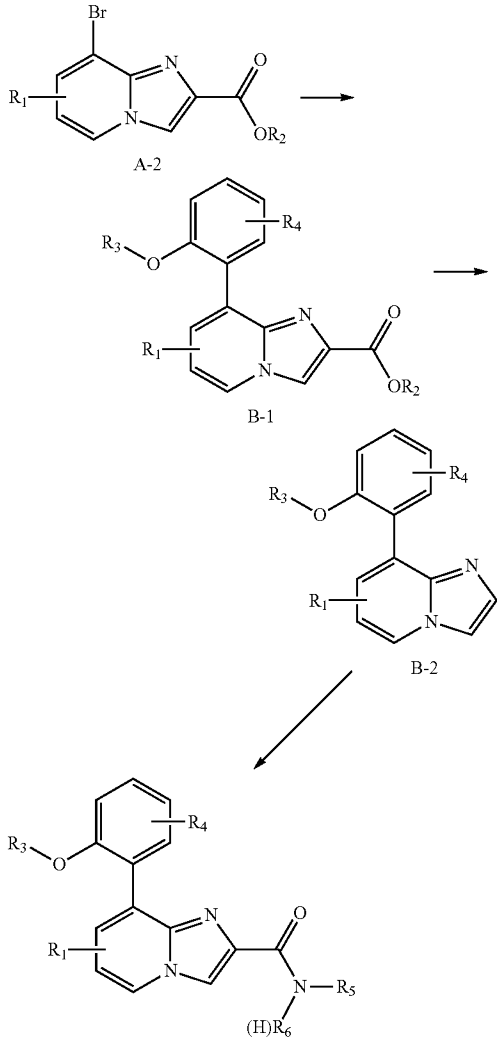

A-2

B-1

B-2

I

As illustrated in Scheme C, in general, compounds of the invention can be prepared by altering the order of operation of Scheme B. Intermediate A-1 can be hydrolyzed by treatment with a base such as lithium hydroxide or sodium hydroxide to yield the intermediate carboxylate C-1, which may be used to form an amide bond with a primary or secondary amine in the presence of a coupling reagent such as EDC or HATU to yield compounds of the formula C-2. Intermediate C-2 can be subjected to palladium-catalyzed Suzuki reaction with an appropriately functionalized boronic ester or acid to yield compounds of the present invention as formula (I).

Scheme C

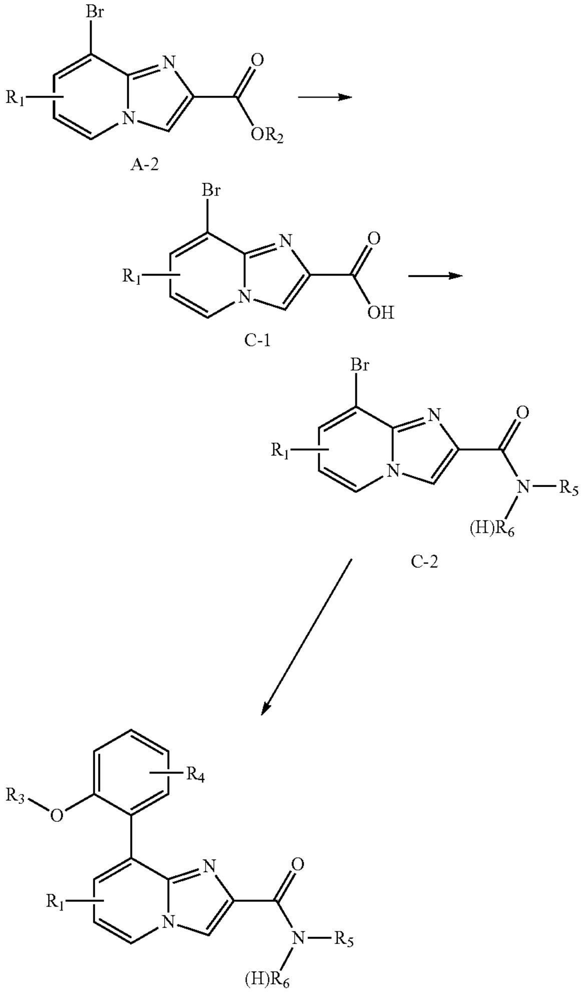

A-2

C-1

C-2

I

As illustrated in Scheme D, in general, compounds of the invention can be prepared by formation of a Weinreb amide with N, O-dimethylhydroxylamine (see, Weinreb, S. M., et al., *Tetrahedron Lett.* 1981, 22, 3815) and intermediate B-2 described in Scheme B in the presence of a coupling reagent such as EDC or HATU to yield compounds of the formula D-1. Intermediate D-1 can be subjected to Grignard reaction conditions with an appropriately functionalized alkyl magnesium halide to yield the intermediate D-2, which can be reduced by treatment with reductants such as DIBAL to yield compounds of the present invention as formula (II).

Scheme D

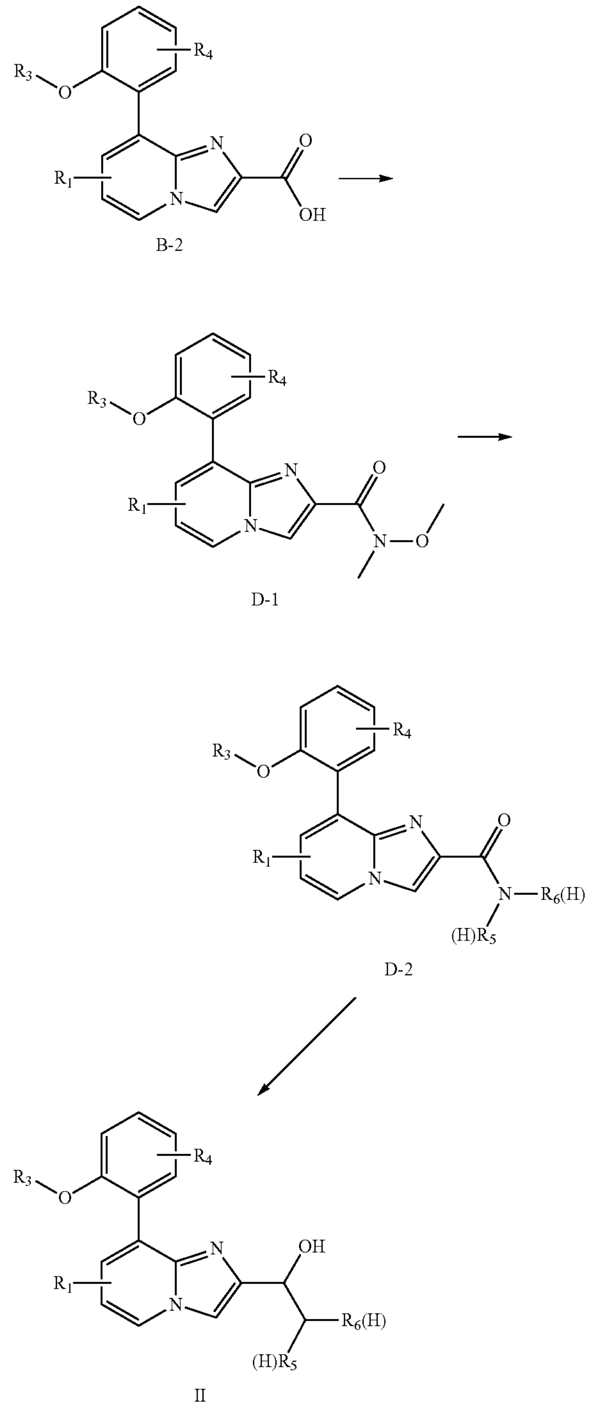

B-2

D-1

D-2

II

As illustrated in Scheme E, in general, compounds of the invention can be prepared by palladium-catalyzed Suzuki reaction between an appropriately functionalized boronic ester or acid and intermediate A-1 described in Scheme A to yield compounds of the formula E-1. Intermediate E-1 can be treated with ethyl-bromoacetate at elevated temperature to yield compounds of the formula E-2, which can be converted to the bromide using phosphorus oxybromide to yield compounds of the formula E-3. Intermediate E-3 can be subjected to palladium-catalyzed Suzuki reaction with an appropriately functionalized boronic ester or acid to yield compounds of the formula E-4, which can be subjected to hydroboration reaction conditions to yield compounds of the present invention as formula (II).

Scheme E

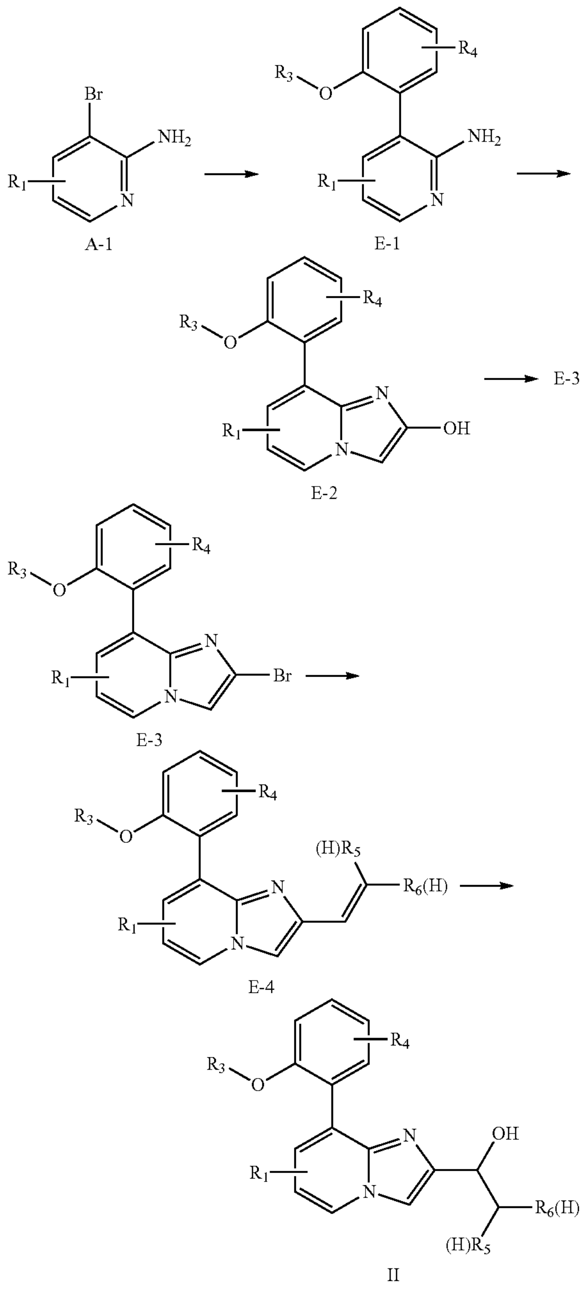

A-1

E-1

E-2

E-3

E-4

II

As illustrated in Scheme F, in general, compounds of the invention can be prepared by amide coupling between a primary amine and intermediate B-2 described in Scheme B in the presence of a coupling reagent such as EDC or HATU to yield compounds of the present invention as formula F-1. Intermediate F-1 can be cyclized by treatment with a dehydrating agent such as nonafluorobutanesulfonyl fluoride to yield compounds of the present invention as formula (III).

Scheme F

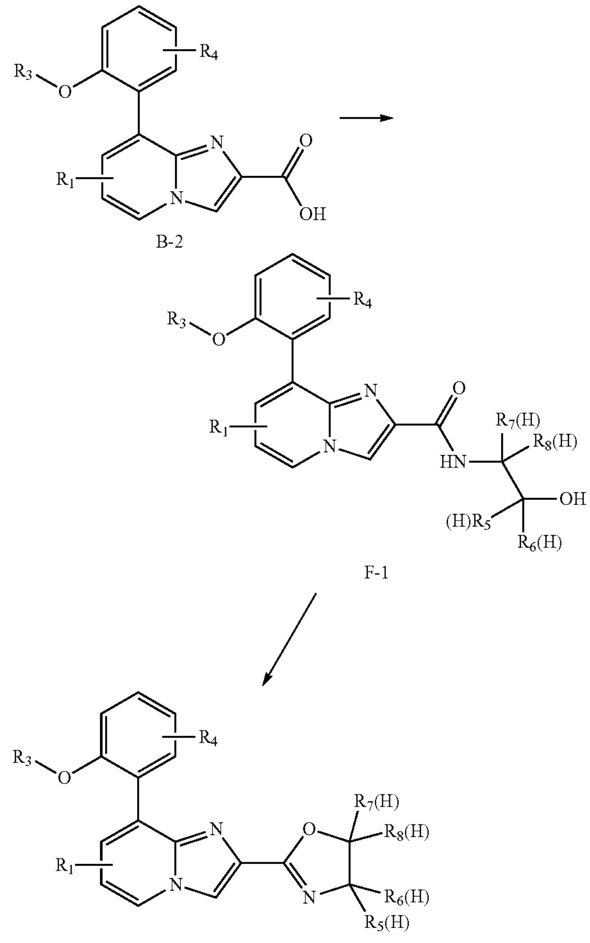

B-2

F-1

III

Scheme G

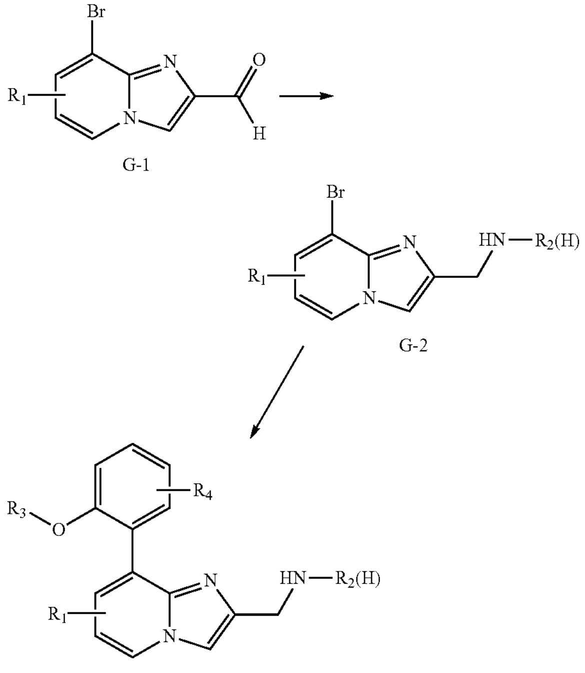

G-1

G-2

IV

As illustrated in Scheme H, in general, compounds of the invention can be prepared by Boc protection of intermediate G-2 described in Scheme G in the presence of a $Boc_{2}O$ and a base such as triethyl amine to yield compounds of the present invention as formula H-1. Intermediate H-1 can be subjected to palladium-catalyzed Suzuki reaction with an appropriately functionalized boronic ester or acid to yield compounds of the present invention as formula H-2, which can be Boc deprotected using acids such as HCl or TFA to yield compounds of the present invention as formula (IV).

Scheme H

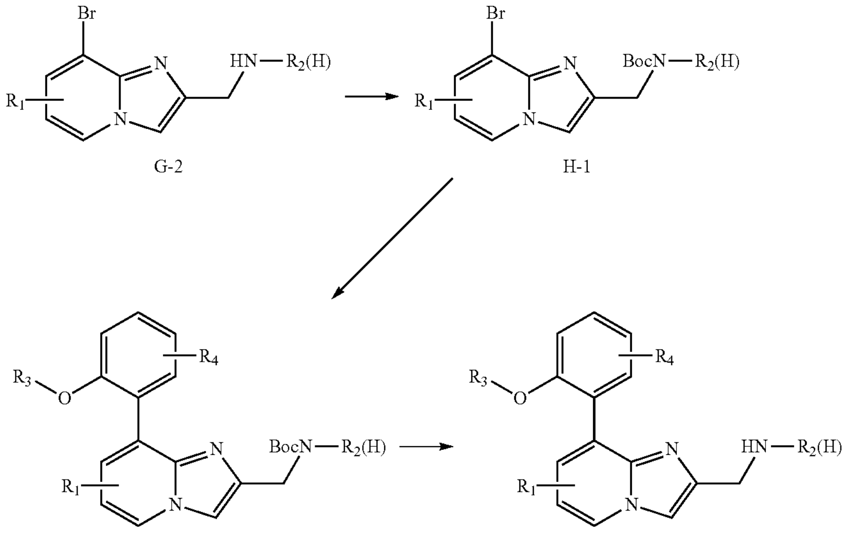

G-2

H-1

H-2

IV

As illustrated in Scheme I, in general, compounds of the invention can be prepared by subjecting intermediate I-1 to palladium-catalyzed Suzuki reaction with an appropriately functionalized boronic ester or acid to yield compounds of the present invention as formula I-2, which may be used to form an amide bond with a carboxylic acid in the presence of a coupling reagent such as EDC or HATU to yield compounds of the present invention as formula (V).

Scheme I

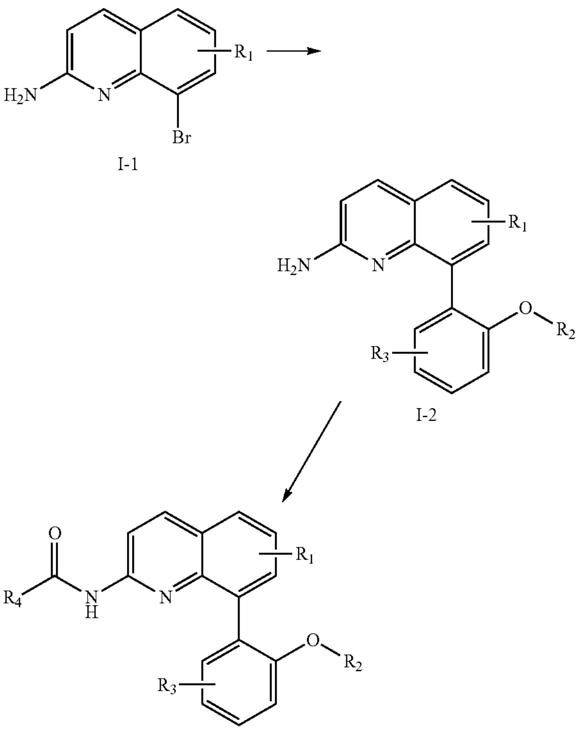

I-1

I-2

V

As illustrated in Scheme J, in general, compounds of the invention can be prepared by subjecting intermediate J-1 to Fischer esterification conditions to yield compounds of the formula J-2 which may be subjected to palladium-catalyzed Suzuki reaction with an appropriately functionalized boronic ester or acid to yield compounds of the present invention as formula J-3. Intermediate J-3 can then be hydrolyzed by treatment with a base such as lithium hydroxide or sodium hydroxide to yield the intermediate carboxylate J-4, which may be used to form an amide bond with a primary or secondary amine in the presence of a coupling reagent such as EDC or HATU to yield compounds of the present invention as formula (VI).

Scheme J

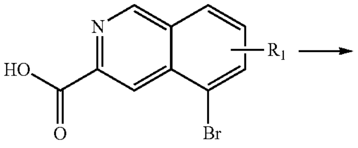

J-1

-continued

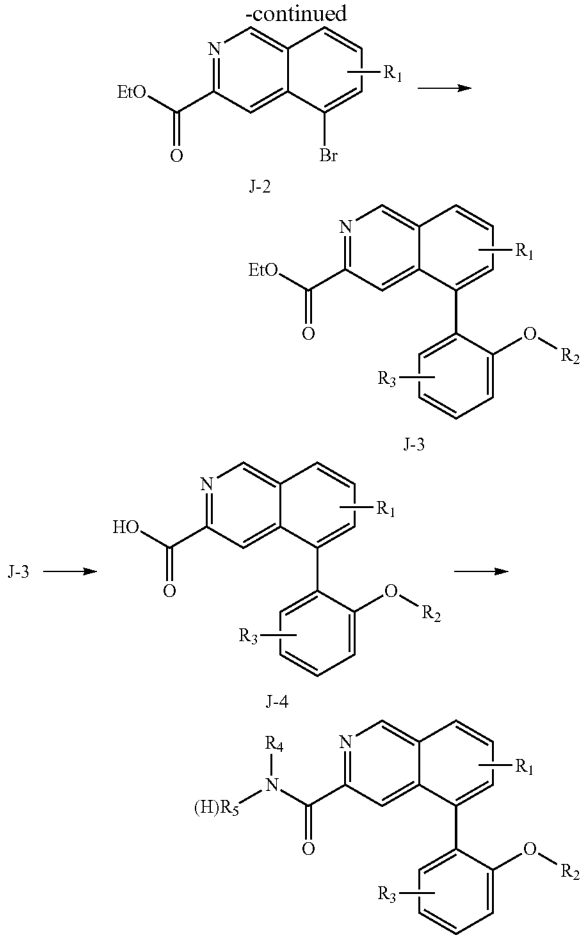

J-2

J-3

J-4

VI

Specific embodiments of the compounds of the invention, and methods of making them, are described in the Intermediates and Examples herein.

Intermediate 1 (I1)

8-(2-(2,2,2-trifluoroethoxy)phenyl)imidazo[1,2-a]pyridine-2-carboxylic acid (I1)

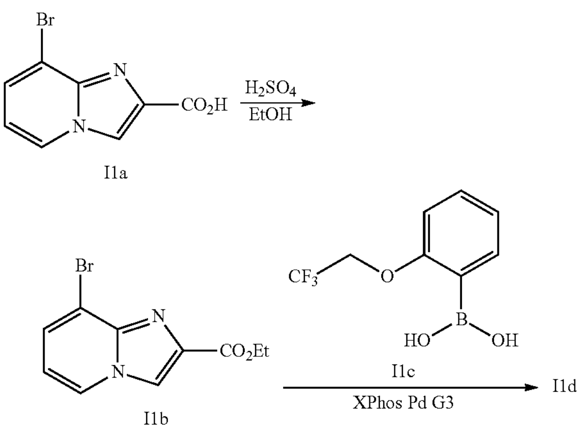

I1a

I1b

I1c

-continued

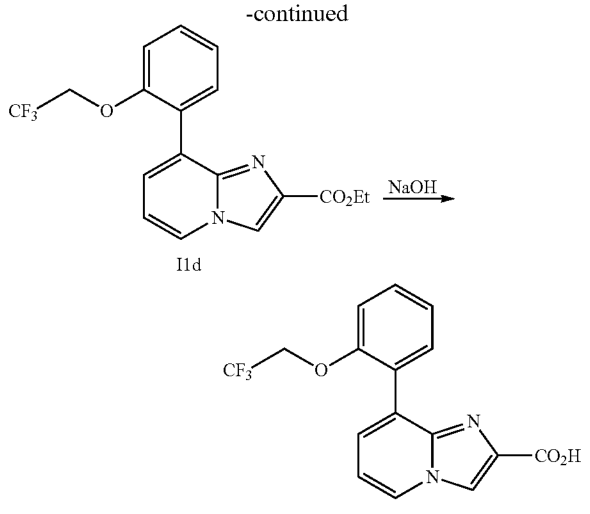

I1d

I1

Step A: ethyl 8-bromoimidazo[1,2-a]pyridine-2-carboxylate (I1b)

A mixture of 8-bromoimidazo[1,2-a]pyridine-2-carboxylic acid (I1a, 900 mg, 3.73 mmol) and aqueous concentrated sulfuric acid (18.8 M, 0.199 mL, 3.73 mmol) in EtOH (7 mL) was heated at reflux for 16 h. The mixture was cooled and concentrated, and the residue was carefully partitioned between ethyl acetate and aqueous saturated sodium bicarbonate solution. The organic layer was washed with water, then brine, dried over sodium sulfate, and concentrated to afford I1b. MS: m/z=269.2 (M+1).

Step B: ethyl 8-(2-(2,2,2-trifluoroethoxy)phenyl)imidazo[1,2-a]pyridine-2-carboxylate (I1d)

A mixture of ethyl 8-bromoimidazo[1,2-a]pyridine-2-carboxylate (I1b, 655 mg, 2.43 mmol), (2-(2,2,2-trifluoroethoxy)phenyl)boronic acid (I1c, 803 mg, 3.65 mmol), aqueous potassium phosphate solution (1 N, 7.30 mL, 7.30 mmol), and XPhos G3 Pd precatalyst ((2-dicyclohexylphosphino-2',4',6'-triisopropyl-1,1'-biphenyl)[2-(2'-amino-1,1'-biphenyl)]palladium(II) methanesulfonate) (206 mg, 0.243 mmol) in THF (5.2 mL) was heated under nitrogen at 80° C. for 16 h. The mixture was cooled, filtered, and concentrated. The residue purified by column chromatography on silica gel (hexanes, grading to 50% EtOAc) to give I1d. MS: m/z=365.4 (M+1).

Step C: 8-(2-(2,2,2-trifluoroethoxy)phenyl)imidazo[1,2-a]pyridine-2-carboxylic acid (I1)

A solution of ethyl 8-(2-(2,2,2-trifluoroethoxy)phenyl)imidazo[1,2-a]pyridine-2-carboxylate (I1d, 710 mg, 1.95 mmol) and aqueous 1 N NaOH (sodium hydroxide) solution (5.85 mL, 5.85 mmol) in a 1:1 mixture of THF and MeOH (methanol) (6 mL) was stirred at 23° C. for 3 h. The mixture was concentrated, and the residue acidified with aqueous 1 M HCl solution (5.85 mL, 5.85 mmol), then partitioned between EtOAc (ethyl acetate) (3×). The combined organic layers were washed with brine, dried over sodium sulfate, and concentrated to give I1. MS: m/z=337.3 (M+1).

Intermediate 2 (I2)

2-bromo-6-fluoro-8-(2-(2,2,2-trifluoroethoxy)phenyl)imidazo[1,2-a]pyridine (I2)

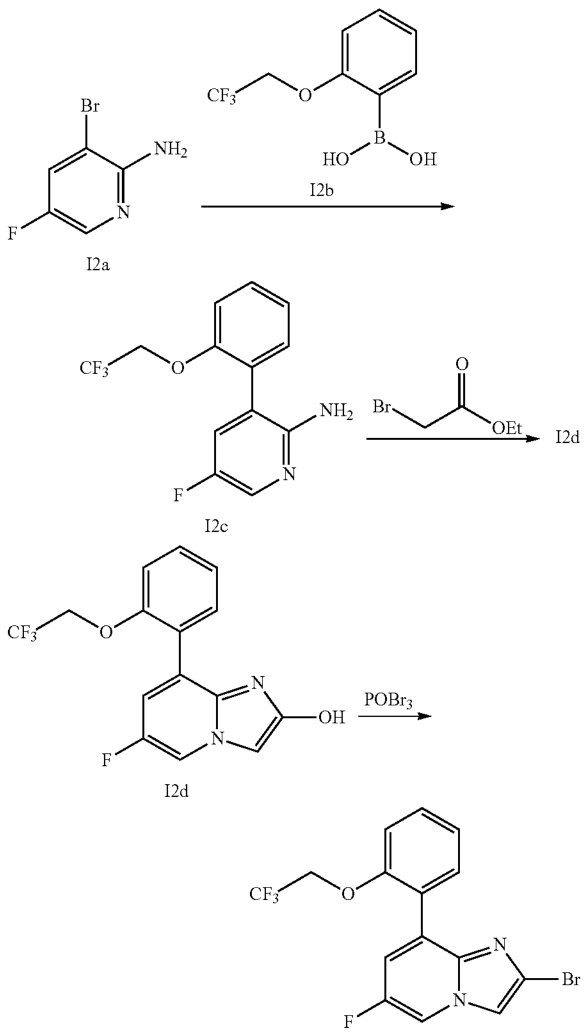

I2a

I2b

I2c

I2d

I2d

I2

Step A: 5-fluoro-3-(2-(2,2,2-trifluoroethoxy)phenyl)pyridin-2-amine (I2c)

To a solution of 3-bromo-5-fluoropyridin-2-amine (I2a, 2.00 g, 10.5 mmol) and (2-(2,2,2-trifluoroethoxy)phenyl)boronic acid (I2b, 2.53 g, 11.5 mmol) in THF (105 mL) was added XPhos G3 precatalyst (886 mg, 1.05 mmol) and aqueous 1 N potassium phosphate solution (31.4 mL, 31.4 mmol). The reaction mixture was sealed under nitrogen and heated at 80° C. for 6 h. The organic layer was separated, then concentrated. The residue was purified by HPLC (30 cm×150 cm C18, 30 min 0-95% acetonitrile-water gradient, 0.05% TFA added) to give compound I2c. MS: m/z=287.2 (M+1).

Step B: 6-fluoro-8-(2-(2,2,2-trifluoroethoxy)phenyl)imidazo[1,2-a]pyridin-2-ol (I2d)

5-fluoro-3-(2-(2,2,2-trifluoroethoxy)phenyl)pyridin-2-amine (I2c, 1.52 g, 5.31 mmol) was added to ethyl 2-bromoacetate (3.53 mL, 31.9 mmol). The mixture was heated at 100° C. for 4 h, then cooled and diluted with $Et_2O$ (diethyl ether) (5 mL). The suspended solid was filtered, washed with additional $Et_2O$ (20 mL), and dried to give I2d. MS: m/z=327.2 (M+1).

Step C: 2-bromo-6-fluoro-8-(2-(2,2,2-trifluoroethoxy)phenyl)imidazo[1,2-a]pyridine (I2)

To a solution of 6-fluoro-8-(2-(2,2,2-trifluoroethoxy)phenyl)imidazo[1,2-a]pyridin-2-ol (I2d, 1.64 g, 5.03 mmol) in DCE (50 mL) was added phosphorus oxybromide (7.21 g, 25.1 mmol). The reaction mixture was heated at reflux for 3 h. The mixture was then cooled to 0° C., neutralized with aqueous concentrated $NaHCO_3$ solution (100 mL), extracted with EtOAc (50 mL×3). The combined organic layers were concentrated, and the residue was purified by silica gel chromatography (0-3% MeOH:DCM) to give compound 12. MS: m/z=390.1 (M+1).

Intermediate 3 (I3)

ethyl 6-chloro-8-(4-fluoro-2-(2,2,2-trifluoroethoxy)phenyl)imidazo[1,2-a]pyridine-2-carboxylate (I3)

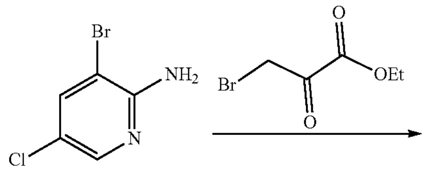

I3a

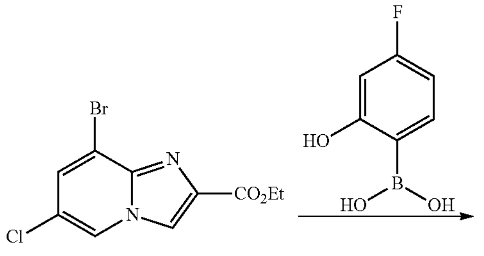

I3b

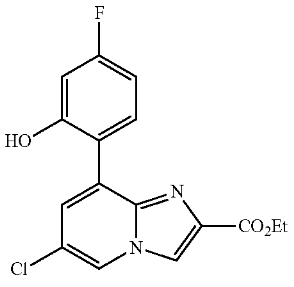

I3c

-continued

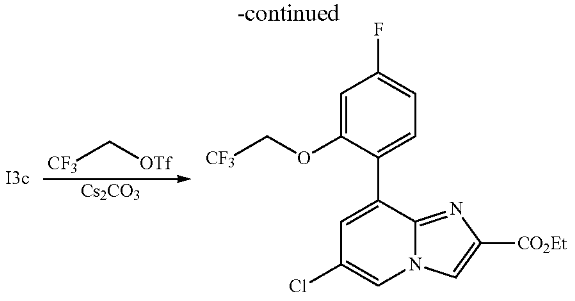

I3

Step A: ethyl 8-bromo-6-chloroimidazo[1,2-a]pyridine-2-carboxylate (I3b)

To a solution of 3-bromo-5-chloropyridin-2-amine (I3a, 7.16 g, 34.5 mmol) in EtOH (ethanol)(173 mL) was added ethyl 3-bromo-2-oxopropanoate (9.65 mL, 69.0 mmol). The reaction mixture was heated at reflux for 3 h, then concentrated. The residue was purified by silica gel chromatography (0-2% MeOH:DCM) to give I3b. MS: m/z=304.1 (M+1).

Step B: ethyl 6-chloro-8-(4-fluoro-2-hydroxyphenyl)imidazo[1,2-a]pyridine-2-carboxylate (I3c)

To a solution of ethyl 8-bromo-6-chloroimidazo[1,2-a]pyridine-2-carboxylate (I3b, 200 mg, 0.659 mmol) and (4-fluoro-2-hydroxyphenyl)boronic acid (92 mg, 0.593 mmol) in THF (2.6 mL) was added XPhos G3 Pd precatalyst (56 mg, 0.066 mmol) and aqueous 1 N potassium phosphate solution (2.0 mL, 2.0 mmol). The reaction mixture was sealed under nitrogen and heated at 45° C. for 1 h. The organic layer was separated, then concentrated. The residue was purified by HPLC (19 cm×150 cm C18, 30 min 0-95% acetonitrile-water gradient, 0.05% TFA added) to give I3c. MS: m/z=335.3 (M+1).

Step C: ethyl 6-chloro-8-(4-fluoro-2-(2,2,2-trifluoroethoxy)phenyl)imidazo[1,2-a]pyridine-2-carboxylate (I3)

To a solution of ethyl 6-chloro-8-(4-fluoro-2-hydroxyphenyl)imidazo[1,2-a]pyridine-2-carboxylate (I3c, 135 mg, 0.403 mmol) in DMF (2.0 mL) at ambient temperature was added $Cs_2CO_3$ (526 mg, 1.61 mmol) followed by 2,2,2-trifluoroethyl trifluoromethanesulfonate (293 μL, 2.02 mmol). The reaction mixture was stirred for 1 h, then partitioned between water (5 mL) and EtOAc (ethyl acetate) (5 mL×3). The combined organic layers were concentrated to give 13. MS: m/z=417.3 (M+1).

Example 1

(1)

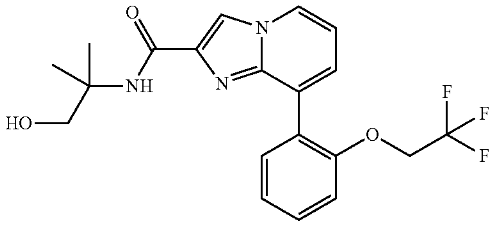

N-(1-hydroxy-2-methylpropan-2-yl)-8-(2-(2,2,2-trifluoroethoxy)phenyl)imidazo[1,2-a]pyridine-2-carboxamide (1)

A mixture of 2-amino-2-methylpropan-1-ol (0.562 mL, 5.95 mmol), 8-(2-(2,2,2-trifluoroethoxy)phenyl)imidazo[1,2-a]pyridine-2-carboxylic acid (I1, 2.00 g, 5.95 mmol), EDC (1.71 g, 8.92 mmol), HOAt (0.971 g, 7.14 mmol), and TEA (3.32 mL, 23.8 mmol) in DMF (5 mL) was heated at 50° C. for 16 h. The mixture was concentrated, and the residue partitioned between saturated aqueous sodium bicarbonate solution (20 mL) and ethyl ether (3×20 mL). The combined organic fractions were washed with water (5×20 mL), then brine (20 mL), dried over $Na_2SO_4$, and concentrated. The residue was purified by column chromatography on silica gel (hexanes, grading to 80% 2:1 EtOAc/EtOH) to provide compound 1. MS: m/z=408.3 (M+1). $^1$H NMR (600 MHz, DMSO-$d_6$) δ 8.55 (dd, J=6.8, 1.1 Hz, 1H), 8.33 (s, 1H), 7.53 (dd, J=7.5, 1.6 Hz, 1H), 7.48-7.42 (m, 2H), 7.31 (d, J=8.1 Hz, 1H), 7.27 (dd, J=7.0, 1.1 Hz, 1H), 7.16 (td, J=7.5, 0.9 Hz, 1H), 7.01 (t, J=6.9 Hz, 1H), 5.08 (t, J=5.4 Hz, 1H), 4.74 (q, J=8.9 Hz, 2H), 3.35 (d, J=5.4 Hz, 2H), 2.48 (s, 4H), 1.28 (s, 6H).

Compounds 2 through 61 as shown in Table 1 were prepared in analogous fashion to that described for Example 1. The amine compounds 16, 17 and 23 were afforded after Boc deprotection of the corresponding amide using TFA. The alcohol of compound 18 was afforded after LAH reduction of the corresponding amido ester. The pyridine N-oxide of compound 58 was afforded after m-CPBA (3-chloroperbenzoic acid) oxidation of the pyridyl amide.

TABLE 1

| Compoud Number | Structure | Compound Name | MS: m/z (M + 1) |
|---|---|---|---|
| 2 | 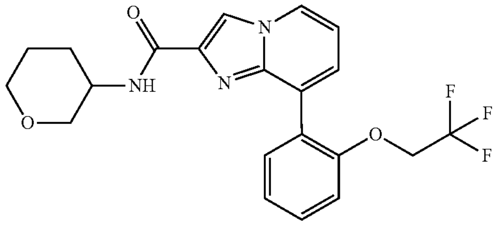 [SMILES: O=C(NC1CCCOC1)c1cn2cccc(-c3ccccc3OCC(F)(F)F)c2n1] | (R or S)-N-(tetrahydro-2H-pyran-3-yl)-8-(2-(2,2,2-trifluoroethoxy)phenyl)imidazo[1,2-a]pyridine-2-carboxamide | 420.0 |
| 3 | 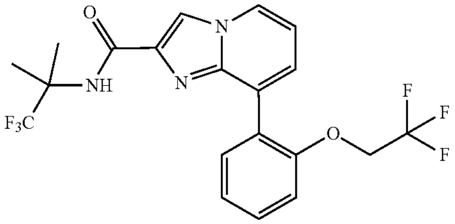 [SMILES: CC(C)(NC(=O)c1cn2cccc(-c3ccccc3OCC(F)(F)F)c2n1)C(F)(F)F] | N-(1,1,1-trifluoro-2-methylpropan-2-yl)-8-(2-(2,2,2-trifluoroethoxy)phenyl)imidazo[1,2-a]pyridine-2-carboxamide | 446.4 |
| 4 | 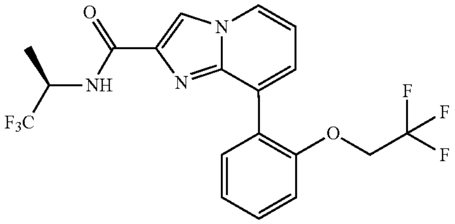 [SMILES: C[C@@H](NC(=O)c1cn2cccc(-c3ccccc3OCC(F)(F)F)c2n1)C(F)(F)F] | (R)-8-(2-(2,2,2-trifluoroethoxy)phenyl)-N-(1,1,1-trifluoropropan-2-yl)imidazo[1,2-a]pyridine-2-carboxamide | 432.3 |
| 5 | 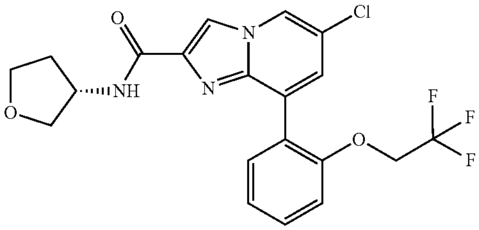 [SMILES: O=C(N[C@H]1CCOC1)c1cn2cc(Cl)cc(-c3ccccc3OCC(F)(F)F)c2n1] | (S)-6-chloro-N-(tetrahydrofuran-3-yl)-8-(2-(2,2,2-trifluoroethoxy)phenyl)imidazo[1,2-a]pyridine-2-carboxamide | 440.2 |
| 6 | 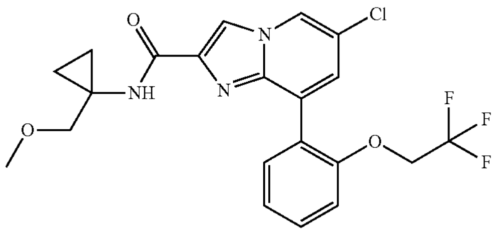 [SMILES: COCC1(NC(=O)c2cn3cc(Cl)cc(-c4ccccc4OCC(F)(F)F)c3n2)CC1] | 6-chloro-N-(1-(methoxymethyl)cyclopropyl)-8-(2-(2,2,2-trifluoroethoxy)phenyl)imidazo[1,2-a]pyridine-2-carboxamide | 476.1 |

TABLE 1-continued

| Compoud Number | Structure | Compound Name | MS: m/z (M + 1) |
|---|---|---|---|
| 7 | 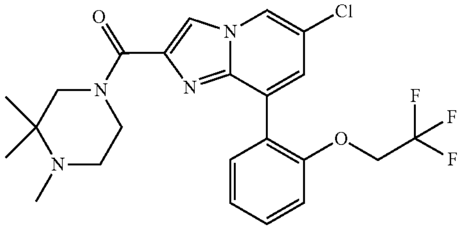 [SMILES: CN1CCN(C(=O)c2cn3cc(Cl)cc(-c4ccccc4OCC(F)(F)F)c3n2)CC1(C)C] | (6-chloro-8-(2-(2,2,2-trifluoroethoxy)phenyl)imidazo[1,2-a]pyridin-2-yl)(3,3,4-trimethylpiperazin-1-yl)methanone | 503.3 |
| 8 | 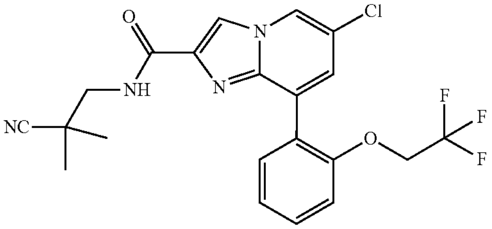 [SMILES: CC(C)(C#N)CNC(=O)c1cn2cc(Cl)cc(-c3ccccc3OCC(F)(F)F)c2n1] | 6-chloro-N-(2-cyano-2-methylpropyl)-8-(2-(2,2,2-trifluoroethoxy)phenyl)imidazo[1,2-a]pyridine-2-carboxamide | 451.2 |
| 9 | 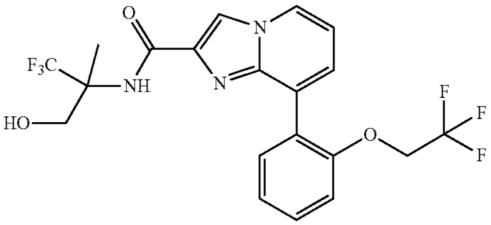 [SMILES: CC(CO)(NC(=O)c1cn2cccc(-c3ccccc3OCC(F)(F)F)c2n1)C(F)(F)F] | (R or S)-N-(1,1,1-trifluoro-3-hydroxy-2-methylpropan-2-yl)-8-(2-(2,2,2-trifluoroethoxy)phenyl)imidazo[1,2-a]pyridine-2-carboxamide | 462.4 |
| 10 | 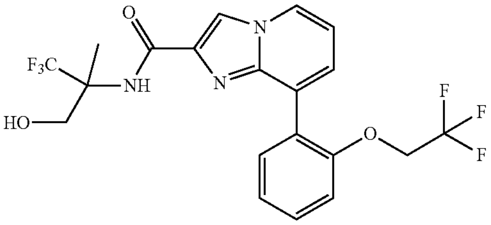 [SMILES: CC(CO)(NC(=O)c1cn2cccc(-c3ccccc3OCC(F)(F)F)c2n1)C(F)(F)F] | (R or S)-N-(1,1,1-trifluoro-3-hydroxy-2-methylpropan-2-yl)-8-(2-(2,2,2-trifluoroethoxy)phenyl)imidazo[1,2-a]pyridine-2-carboxamide | 462.4 |
| 11 | 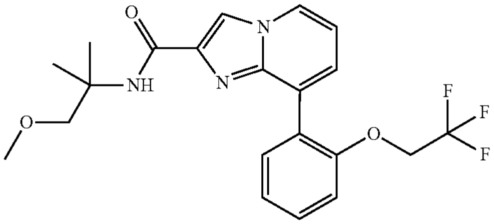 [SMILES: COCC(C)(C)NC(=O)c1cn2cccc(-c3ccccc3OCC(F)(F)F)c2n1] | N-(1-methoxy-2-methylpropan-2-yl)-8-(2-(2,2,2-trifluoroethoxy)phenyl)imidazo[1,2-a]pyridine-2-carboxamide | 422.4 |
| 12 | 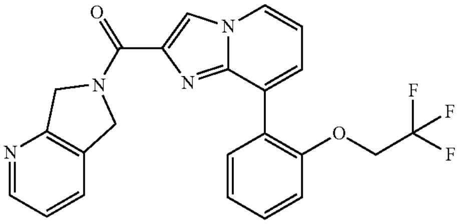 [SMILES: O=C(c1cn2cccc(-c3ccccc3OCC(F)(F)F)c2n1)N1Cc2cccnc2C1] | (5,7-dihydro-6H-pyrrolo[3,4-b]pyridin-6-yl)(8-(2-(2,2,2-trifluoroethoxy)phenyl)imidazo[1,2-a]pyridin-2-yl)methanone | 439.2 |

TABLE 1-continued

| Compoud Number | Structure | Compound Name | MS: m/z (M + 1) |
|---|---|---|---|
| 13 | 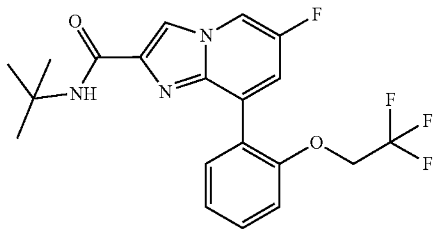 [SMILES: CC(C)(C)NC(=O)c1cn2cc(F)cc(-c3ccccc3OCC(F)(F)F)c2n1] | N-(tert-butyl)-6-fluoro-8-(2-(2,2,2-trifluoroethoxy)phenyl)imidazo[1,2-a]pyridine-2-carboxamide | 410.0 |
| 14 | 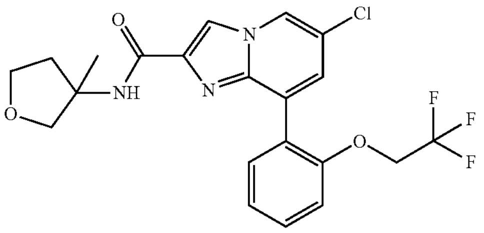 [SMILES: CC1(NC(=O)c2cn3cc(Cl)cc(-c4ccccc4OCC(F)(F)F)c3n2)CCOC1] | (R and S)-6-chloro-N-(3-methyltetrahydrofuran-3-yl)-8-(2-(2,2,2-trifluoroethoxy)phenyl)imidazo[1,2-a]pyridine-2-carboxamide | 454.0 |
| 15 | 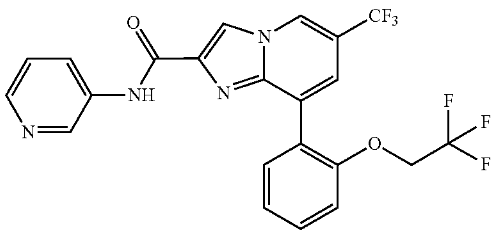 [SMILES: O=C(Nc1cccnc1)c1cn2cc(C(F)(F)F)cc(-c3ccccc3OCC(F)(F)F)c2n1] | N-(pyridin-3-yl)-8-(2-(2,2,2-trifluoroethoxy)phenyl)-6-(trifluoromethyl)imidazo[1,2-a]pyridine-2-carboxamide | 481.1 |
| 16 | 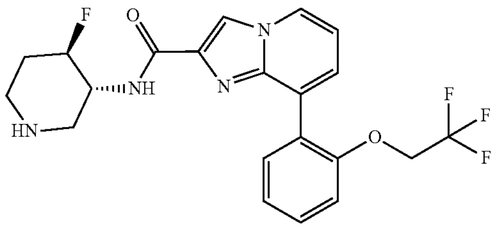 [SMILES: O=C(N[C@@H]1CNCC[C@H]1F)c1cn2cccc(-c3ccccc3OCC(F)(F)F)c2n1] | N-(trans-4-fluoropiperidin-3-yl)-8-(2-(2,2,2-trifluoroethoxy)phenyl)imidazo[1,2-a]pyridine-2-carboxamide | 437.5 |
| 17 | 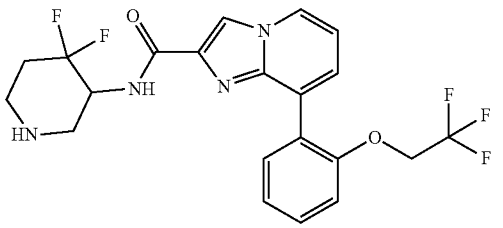 [SMILES: O=C(NC1CNCCC1(F)F)c1cn2cccc(-c3ccccc3OCC(F)(F)F)c2n1] | (R and S)-N-(4,4-difluoropiperidin-3-yl)-8-(2-(2,2,2-trifluoroethoxy)phenyl)imidazo[1,2-a]pyridine-2-carboxamide | 455.3 |
| 18 | 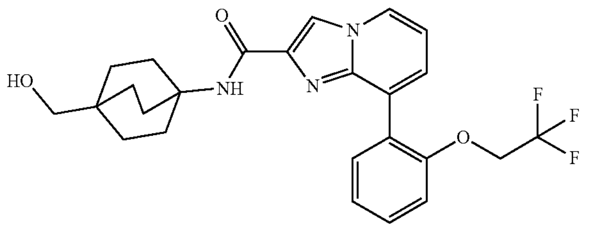 [SMILES: O=C(NC12CCC(CO)(CC1)CC2)c1cn2cccc(-c3ccccc3OCC(F)(F)F)c2n1] | N-(4-(hydroxymethyl)bicyclo[2.2.2]octan-1-yl)-8-(2-(2,2,2-trifluoroethoxy)phenyl)imidazo[1,2-a]pyridine-2-carboxamide | 474.5 |

TABLE 1-continued

| Compoud Number | Structure | Compound Name | MS: m/z (M + 1) |
|---|---|---|---|
| 19 | 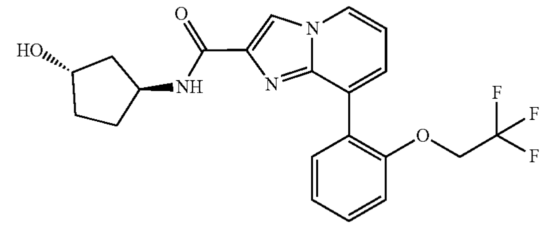 [SMILES: O=C(N[C@H]1CC[C@H](O)C1)c1cn2cccc(-c3ccccc3OCC(F)(F)F)c2n1] | N-(trans-3-hydroxycyclopentyl)-8-(2-(2,2,2-trifluoroethoxy)phenyl)imidazo[1,2-a]pyridine-2-carboxamide | 420.4 |
| 20 | 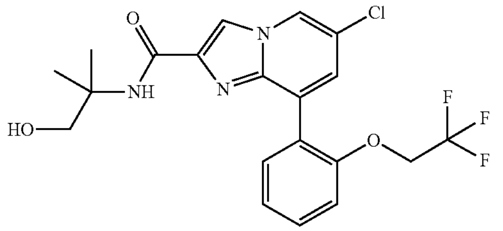 [SMILES: CC(C)(CO)NC(=O)c1cn2cc(Cl)cc(-c3ccccc3OCC(F)(F)F)c2n1] | 6-chloro-N-(1-hydroxy-2-methylpropan-2-yl)-8-(2-(2,2,2-trifluoroethoxy)phenyl)imidazo[1,2-a]pyridine-2-carboxamide | 442.4 |
| 21 | 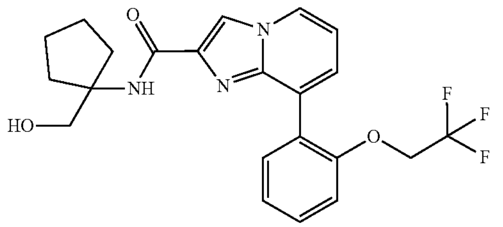 [SMILES: O=C(NC1(CO)CCCC1)c1cn2cccc(-c3ccccc3OCC(F)(F)F)c2n1] | N-(1-(hydroxymethyl)cyclopentyl)-8-(2-(2,2,2-trifluoroethoxy)phenyl)imidazo[1,2-a]pyridine-2-carboxamide | 434.1 |
| 22 | 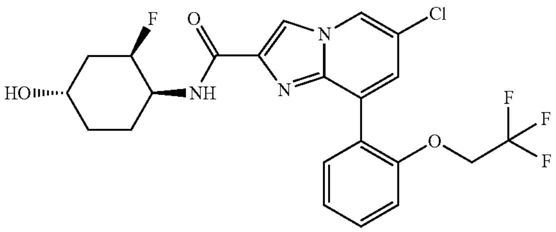 [SMILES: O=C(N[C@H]1CC[C@H](O)C[C@H]1F)c1cn2cc(Cl)cc(-c3ccccc3OCC(F)(F)F)c2n1] | 6-chloro-N-((1S,2R,4S and 1R, 2S,4R)-2-fluoro-4-hydroxycyclohexyl)-8-(2-(2,2,2-trifluoroethoxy)phenyl)imidazo[1,2-a]pyridine-2-carboxamide | 486.1 |
| 23 | 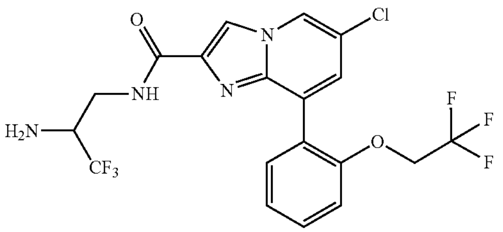 [SMILES: NC(CNC(=O)c1cn2cc(Cl)cc(-c3ccccc3OCC(F)(F)F)c2n1)C(F)(F)F] | N-(2-amino-3,3,3-trifluoropropyl)-6-chloro-8-(2-(2,2,2-trifluoroethoxy)phenyl)imidazo[1,2-a]pyridine-2-carboxamide | 481.4 |
| 24 | 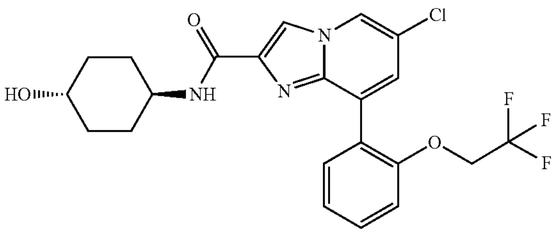 | 6-chloro-N-(trans-4-hydroxycyclohexyl)-8-(2-(2,2,2-trifluoroethoxy)phenyl)imidazo[1,2-a]pyridine-2-carboxamide | 468.4 |

TABLE 1-continued

| Compoud Number | Structure | Compound Name | MS: m/z (M + 1) |
|---|---|---|---|
| 25 | 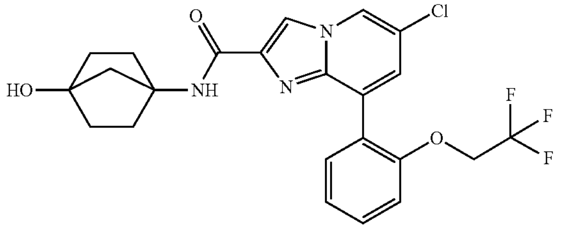 [SMILES: O=C(NC12CCC(O)(CC1)C2)c1cn2cc(Cl)cc(-c3ccccc3OCC(F)(F)F)c2n1] | 6-chloro-N-(4-hydroxybicyclo[2.2.1]heptan-1-yl)-8-(2-(2,2,2-trifluoroethoxy)phenyl)imidazo[1,2-a]pyridine-2-carboxamide | 480.4 |
| 26 | 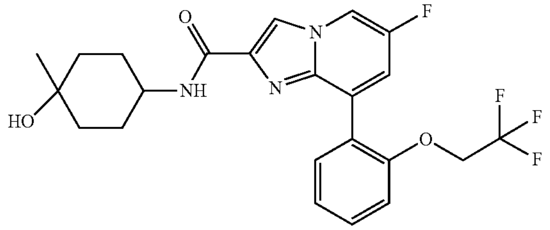 [SMILES: CC1(O)CCC(NC(=O)c2cn3cc(F)cc(-c4ccccc4OCC(F)(F)F)c3n2)CC1] | cis or trans-6-fluoro-N-(4-hydroxy-4-methylcyclohexyl)-8-(2-(2,2,2-trifluoroethoxy)phenyl)imidazo[1,2-a]pyridine-2-carboxamide | 466.2 |
| 27 | 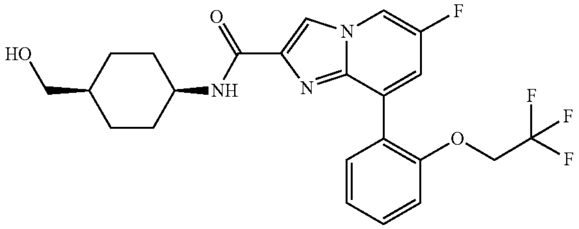 [SMILES: O=C(N[C@H]1CC[C@@H](CO)CC1)c1cn2cc(F)cc(-c3ccccc3OCC(F)(F)F)c2n1] | 6-fluoro-N-(cis-4-(hydroxymethyl)cyclohexyl)-8-(2-(2,2,2-trifluoroethoxy)phenyl)imidazo[1,2-a]pyridine-2-carboxamide | 466.2 |
| 28 | 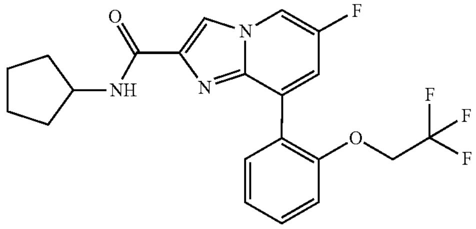 [SMILES: O=C(NC1CCCC1)c1cn2cc(F)cc(-c3ccccc3OCC(F)(F)F)c2n1] | N-cyclopentyl-6-fluoro-8-(2-(2,2,2-trifluoroethoxy)phenyl)imidazo[1,2-a]pyridine-2-carboxamide | 422.2 |
| 29 | 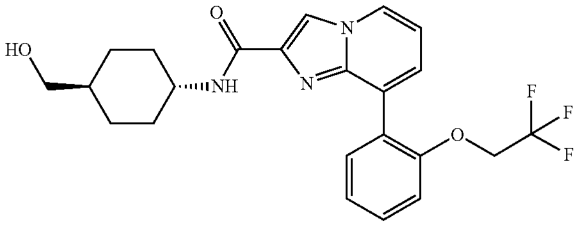 [SMILES: O=C(N[C@H]1CC[C@H](CO)CC1)c1cn2cccc(-c3ccccc3OCC(F)(F)F)c2n1] | N-(trans-4-(hydroxymethyl)cyclohexyl)-8-(2-(2,2,2-trifluoroethoxy)phenyl)imidazo[1,2-a]pyridine-2-carboxamide | 448.2 |
| 30 | 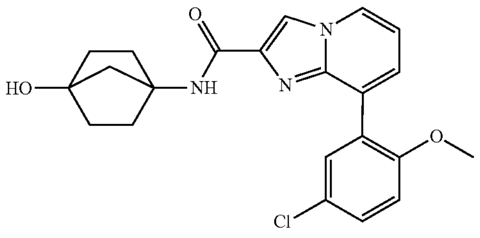 [SMILES: COc1ccc(Cl)cc1-c1cccn2cc(C(=O)NC34CCC(O)(CC3)C4)nc12] | 8-(5-chloro-2-methoxyphenyl)-N-(4-hydroxybicyclo[2.2.1]heptan-1-yl)imidazo[1,2-a]pyridine-2-carboxamide | 412.2 |

TABLE 1-continued

| Compoud Number | Structure | Compound Name | MS: m/z (M + 1) |
| --- | --- | --- | --- |
| 31 | 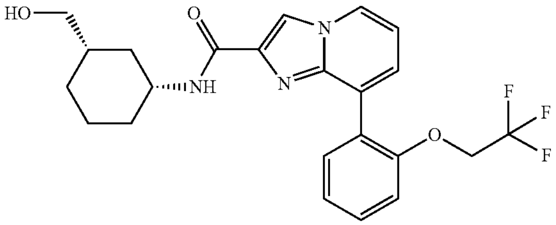 [SMILES: O=C(N[C@@H]1CCC[C@H](CO)C1)c1cn2cccc(-c3ccccc3OCC(F)(F)F)c2n1] | N-(cis-3-(hydroxymethyl)cyclohexyl)-8-(2-(2,2,2-trifluoroethoxy)phenyl)imidazo[1,2-a]pyridine-2-carboxamide | 448.2 |
| 32 | 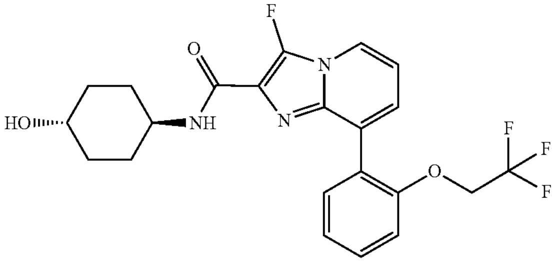 [SMILES: O=C(N[C@H]1CC[C@H](O)CC1)c1nc2c(-c3ccccc3OCC(F)(F)F)cccn2c1F] | 3-fluoro-N-(trans-4-hydroxycyclohexyl)-8-(2-(2,2,2-trifluoroethoxy)phenyl)imidazo[1,2-a]pyridine-2-carboxamide | 452.4 |
| 33 | 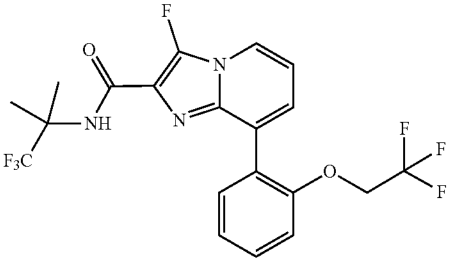 [SMILES: CC(C)(NC(=O)c1nc2c(-c3ccccc3OCC(F)(F)F)cccn2c1F)C(F)(F)F] | 3-fluoro-N-(1,1,1-trifluoro-2-methylpropan-2-yl)-8-(2-(2,2,2-trifluoroethoxy)phenyl)imidazo[1,2-a]pyridine-2-carboxamide | 464.3 |
| 34 | 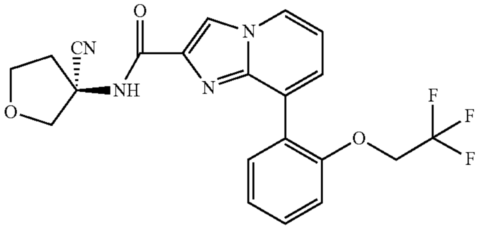 [SMILES: N#C[C@@]1(NC(=O)c2cn3cccc(-c4ccccc4OCC(F)(F)F)c3n2)CCOC1] | (S)-N-(3-cyanotetrahydrofuran-3-yl)-8-(2-(2,2,2-trifluoroethoxy)phenyl)imidazo[1,2-a]pyridine-2-carboxamide | 431.2 |
| 35 | 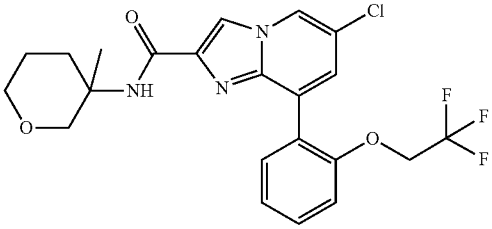 [SMILES: CC1(NC(=O)c2cn3cc(Cl)cc(-c4ccccc4OCC(F)(F)F)c3n2)CCCOC1] | (R and S)-6-chloro-N-(3-methyltetrahydro-2H-pyran-3-yl)-8-(2-(2,2,2-trifluoroethoxy)phenyl)imidazo[1,2-a]pyridine-2-carboxamide | 468.2 |
| 36 | 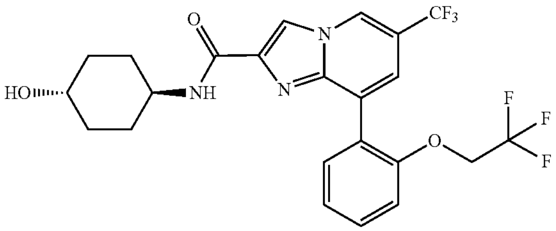 [SMILES: O=C(N[C@H]1CC[C@H](O)CC1)c1cn2cc(C(F)(F)F)cc(-c3ccccc3OCC(F)(F)F)c2n1] | N-(trans-4-hydroxycyclohexyl)-8-(2-(2,2,2-trifluoroethoxy)phenyl)-6-(trifluoromethyl)imidazo[1,2-a]pyridine-2-carboxamide | 502.2 |

TABLE 1-continued

| Compoud Number | Structure | Compound Name | MS: m/z (M + 1) |
| --- | --- | --- | --- |
| 37 | 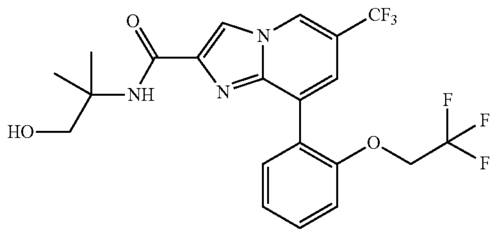 | N-(1-hydroxy-2-methylpropan-2-yl)-8-(2-(2,2,2-trifluoroethoxy)phenyl)-6-(trifluoromethyl)imidazo[1,2-a]pyridine-2-carboxamide | 476.2 |
| 38 | 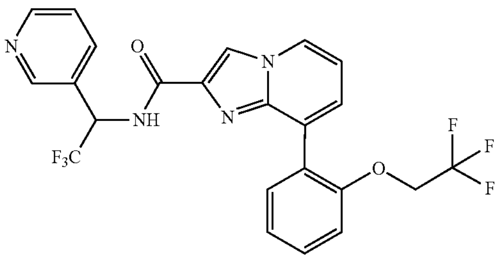 [SMILES: O=C(NC(c1cccnc1)C(F)(F)F)c1cn2cccc(-c3ccccc3OCC(F)(F)F)c2n1] | (R and S)-N-(2,2,2-trifluoro-1-(pyridin-3-yl)ethyl)-8-(2-(2,2,2-trifluoroethoxy)phenyl)imidazo[1,2-a]pyridine-2-carboxamide | 495.1 |
| 39 | 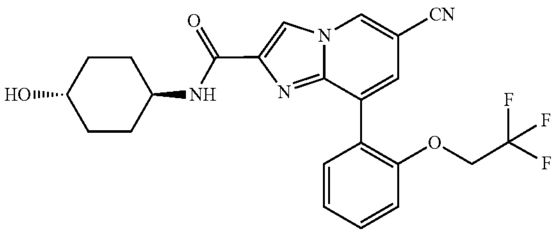 [SMILES: N#Cc1cc(-c2ccccc2OCC(F)(F)F)c2nc(C(=O)N[C@H]3CC[C@H](O)CC3)cn2c1] | 6-cyano-N-(trans-4-hydroxycyclohexyl)-8-(2-(2,2,2-trifluoroethoxy)phenyl)imidazo[1,2-a]pyridine-2-carboxamide | 459.2 |
| 40 | 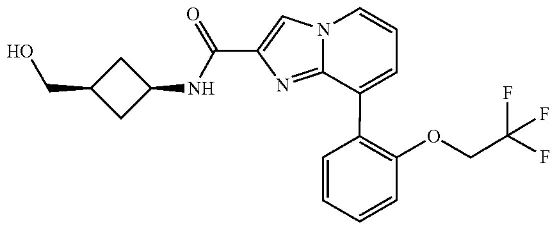 [SMILES: O=C(N[C@H]1C[C@@H](CO)C1)c1cn2cccc(-c3ccccc3OCC(F)(F)F)c2n1] | N-cis-3-(hydroxymethyl)cyclobutyl)-8-(2-(2,2,2-trifluoroethoxy)phenyl)imidazo[1,2-a]pyridine-2-carboxamide | 420.2 |
| 41 | 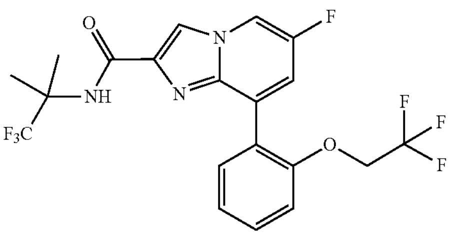 [SMILES: CC(C)(NC(=O)c1cn2cc(F)cc(-c3ccccc3OCC(F)(F)F)c2n1)C(F)(F)F] | 6-fluoro-N-(1,1,1-trifluoro-2-methylpropan-2-yl)-8-(2-(2,2,2-trifluoroethoxy)phenyl)imidazo[1,2-a]pyridine-2-carboxamide | 464.1 |
| 42 | 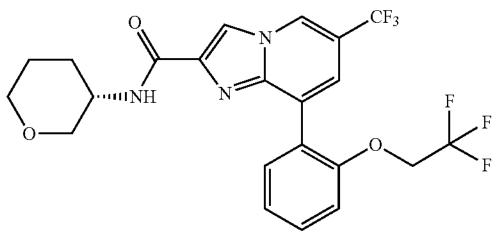 [SMILES: O=C(N[C@H]1CCCOC1)c1cn2cc(C(F)(F)F)cc(-c3ccccc3OCC(F)(F)F)c2n1] | (S)-N-(tetrahydro-2H-pyran-3-yl)-8-(2-(2,2,2-trifluoroethoxy)phenyl)-6-(trifluoromethyl)imidazo[1,2-a]pyridine-2-carboxamide | 488.2 |

TABLE 1-continued

| Compoud Number | Structure | Compound Name | MS: m/z (M + 1) |
|---|---|---|---|
| 43 | 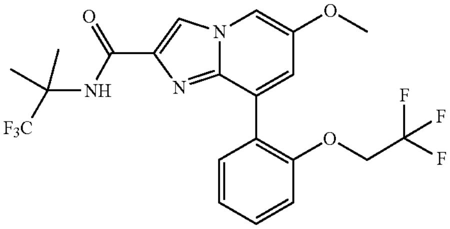 [SMILES: COc1cc(-c2ccccc2OCC(F)(F)F)c2nc(C(=O)NC(C)(C)C(F)(F)F)cn2c1] | 6-methoxy-N-(1,1,1-trifluoro-2-methylpropan-2-yl)-8-(2-(2,2,2-trifluoroethoxy)phenyl)imidazo[1,2-a]pyridine-2-carboxamide | 476.2 |
| 44 | 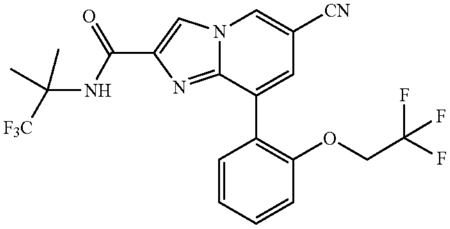 [SMILES: CC(C)(NC(=O)c1cn2cc(C#N)cc(-c3ccccc3OCC(F)(F)F)c2n1)C(F)(F)F] | 6-cyano-N-(1,1,1-trifluoro-2-methylpropan-2-yl)-8-(2-(2,2,2-trifluoroethoxy)phenyl)imidazo[1,2-a]pyridine-2-carboxamide | 471.2 |
| 45 | 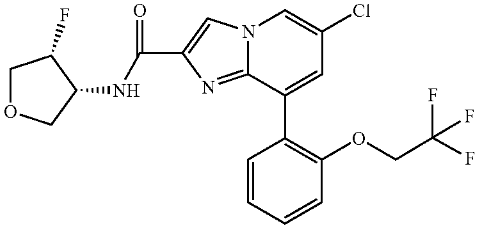 [SMILES: O=C(N[C@@H]1COC[C@@H]1F)c1cn2cc(Cl)cc(-c3ccccc3OCC(F)(F)F)c2n1] | 6-chloro-N-((3R,4R)-4-fluorotetrahydrofuran-3-yl)-8-(2-(2,2,2-trifluoroethoxy)phenyl)imidazo[1,2-a]pyridine-2-carboxamide | 458.1 |
| 46 | 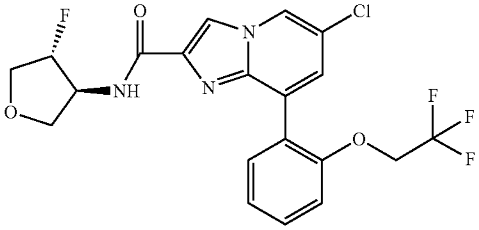 [SMILES: O=C(N[C@H]1COC[C@@H]1F)c1cn2cc(Cl)cc(-c3ccccc3OCC(F)(F)F)c2n1] | 6-chloro-N-((3S,4R)-4-fluorotetrahydrofuran-3-yl)-8-(2-(2,2,2-trifluoroethoxy)phenyl)imidazo[1,2-a]pyridine-2-carboxamide | 458.1 |
| 47 | 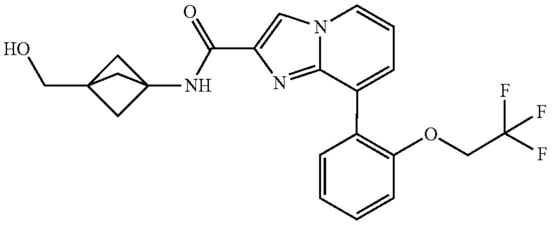 [SMILES: O=C(NC12CC(CO)(C1)C2)c1cn2cccc(-c3ccccc3OCC(F)(F)F)c2n1] | N-(3-(hydroxymethyl)bicyclo[1.1.1]pentan-1-yl)-8-(2-(2,2,2-trifluoroethoxy)phenyl)imidazo[1,2-a]pyridine-2-carboxamide | 432.1 |
| 48 | 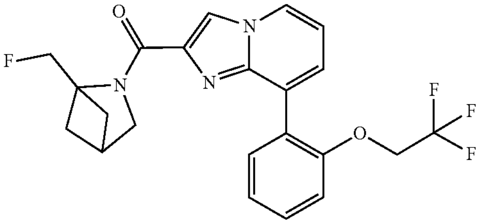 [SMILES: O=C(c1cn2cccc(-c3ccccc3OCC(F)(F)F)c2n1)N1CC2CC1(CF)C2] | (1-(fluoromethyl)-2-azabicyclo[2.1.1]hexan-2-yl)(8-(2-(2,2,2-trifluoroethoxy)phenyl)imidazo[1,2-a]pyridin-2-yl)methanone | 434.4 |

TABLE 1-continued

| Compoud Number | Structure | Compound Name | MS: m/z (M + 1) |
|---|---|---|---|
| 49 | 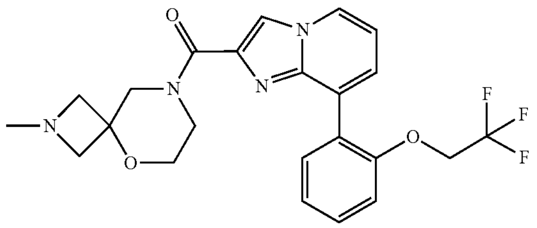 [SMILES: CN1CC2(C1)CN(C(=O)c1cn3cccc(-c4ccccc4OCC(F)(F)F)c3n1)CCO2] | (2-methyl-5-oxa-2,8-diazaspiro[3.5]nonan-8-yl)(8-(2-(2,2,2-trifluoroethoxy)phenyl)imidazo[1,2-a]pyridin-2-yl)methanone | 461.4 |
| 50 | 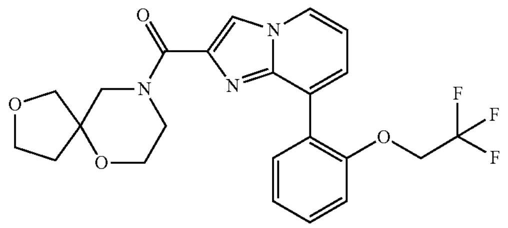 [SMILES: O=C(c1cn2cccc(-c3ccccc3OCC(F)(F)F)c2n1)N1CCOC2(CCOC2)C1] | (R and S)-(2,6-dioxa-9-azaspiro[4.5]decan-9-yl)(8-(2-(2,2,2-trifluoroethoxy)phenyl)imidazo[1,2-a]pyridin-2-yl)methanone | 462.4 |
| 51 | 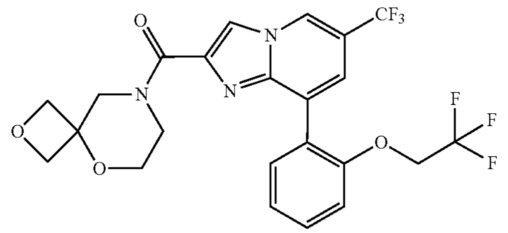 [SMILES: O=C(c1cn2cc(C(F)(F)F)cc(-c3ccccc3OCC(F)(F)F)c2n1)N1CCOC2(COC2)C1] | (2,5-dioxa-8-azaspiro[3.5]nonan-8-yl)(8-(2-(2,2,2-trifluoroethoxy)phenyl)-6-(trifluoromethyl)imidazo[1,2-a]pyridin-2-yl)methanone | 516.5 |
| 52 | 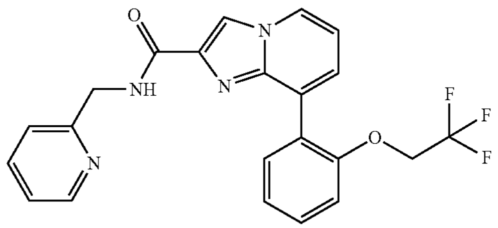 [SMILES: O=C(NCc1ccccn1)c1cn2cccc(-c3ccccc3OCC(F)(F)F)c2n1] | N-(pyridin-2-ylmethyl)-8-(2-(2,2,2-trifluoroethoxy)phenyl)imidazo[1,2-a]pyridine-2-carboxamide | 427.2 |
| 53 | 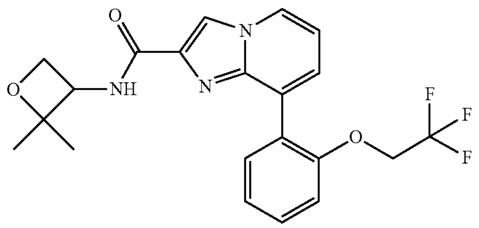 [SMILES: CC1(C)OCC1NC(=O)c1cn2cccc(-c3ccccc3OCC(F)(F)F)c2n1] | N-(2,2-dimethyloxetan-3-yl)-8-(2-(2,2,2-trifluoroethoxy)phenyl)imidazo[1,2-a]pyridine-2-carboxamide | 420.3 |
| 54 | 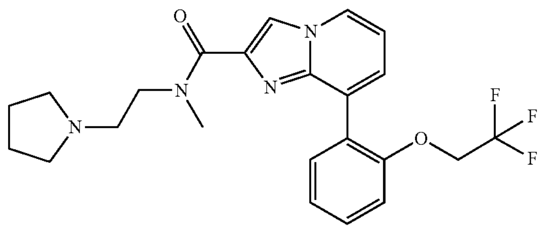 [SMILES: CN(CCN1CCCC1)C(=O)c1cn2cccc(-c3ccccc3OCC(F)(F)F)c2n1] | N-methyl-N-(2-(pyrrolidin-1-yl)ethyl)-8-(2-(2,2,2-trifluoroethoxy)phenyl)imidazo[1,2-a]pyridine-2-carboxamide | 447.3 |

TABLE 1-continued

| Compoud Number | Structure | Compound Name | MS: m/z (M + 1) |
|---|---|---|---|
| 55 | 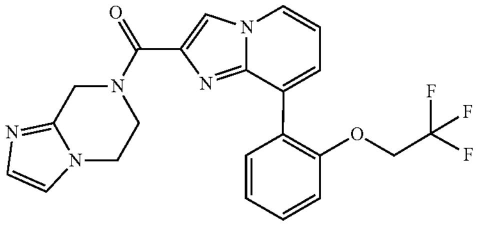 [SMILES: O=C(c1cn2cccc(-c3ccccc3OCC(F)(F)F)c2n1)N1CCn2ccnc2C1] | (5,6-dihydroimidazo[1,2-a]pyrazin-7(8H)-yl)(8-(2-(2,2,2-trifluoroethoxy)phenyl)imidazo[1,2-a]pyridin-2-yl)methanone | 442.3 |
| 56 | 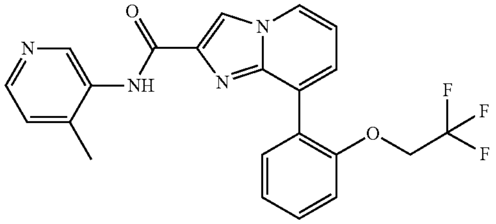 [SMILES: Cc1ccncc1NC(=O)c1cn2cccc(-c3ccccc3OCC(F)(F)F)c2n1] | N-(4-methylpyridin-3-yl)-8-(2-(2,2,2-trifluoroethoxy)phenyl)imidazo[1,2-a]pyridine-2-carboxamide | 427.2 |
| 57 | 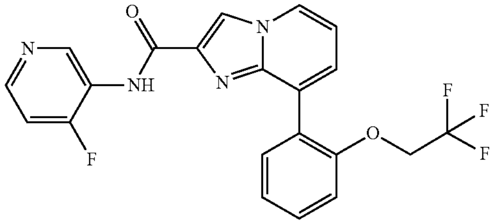 [SMILES: O=C(Nc1cnccc1F)c1cn2cccc(-c3ccccc3OCC(F)(F)F)c2n1] | N-(4-fluoropyridin-3-yl)-8-(2-(2,2,2-trifluoroethoxy)phenyl)imidazo[1,2-a]pyridine-2-carboxamide | 431.1 |
| 58 | 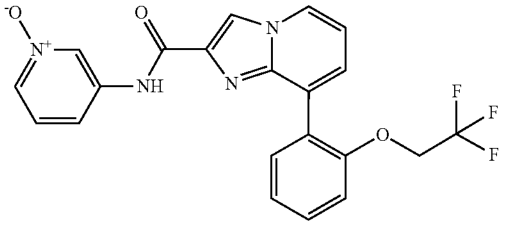 | 3-(8-(2-(2,2,2-trifluoroethoxy)phenyl)imidazo[1,2-a]pyridine-2-carboxamido)pyridine-1-oxide | 429.2 |
| 59 | 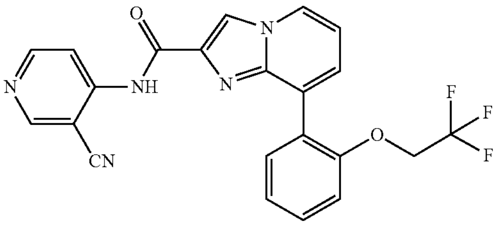 [SMILES: N#Cc1cnccc1NC(=O)c1cn2cccc(-c3ccccc3OCC(F)(F)F)c2n1] | N-(3-cyanopyridin-4-yl)-8-(2-(2,2,2-trifluoroethoxy)phenyl)imidazo[1,2-a]pyridine-2-carboxamide | 438.2 |
| 60 | 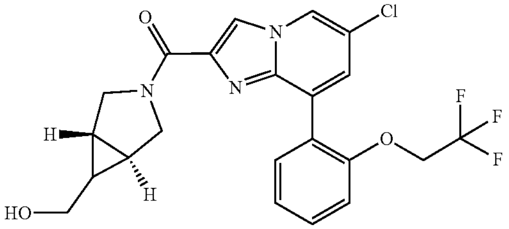 [SMILES: O=C(c1cn2cc(Cl)cc(-c3ccccc3OCC(F)(F)F)c2n1)N1C[C@H]2C(CO)[C@@H]2C1] | (6-chloro-8-(2-(2,2,2-trifluoroethoxy)phenyl)imidazo[1,2-a]pyridin-2-yl)((1R,5R)-6-(hydroxymethyl)-3-azabicyclo[3.1.0]hexan-3-yl)methanone | 466.2 |

TABLE 1-continued

| Compoud Number | Structure | Compound Name | MS: m/z (M + 1) |
|---|---|---|---|
| 61 | 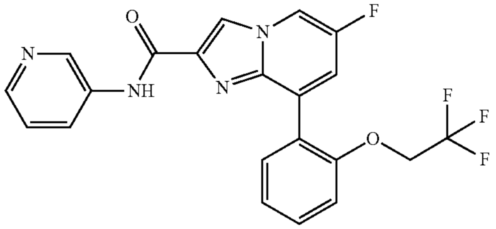 [SMILES: O=C(Nc1cccnc1)c1cn2cc(F)cc(-c3ccccc3OCC(F)(F)F)c2n1] | 6-fluoro-N-(pyridin-3-yl)-8-(2-(2,2,2-trifluoroethoxy)phenyl)imidazo[1,2-a]pyridine-2-carboxamide | 431.2 |

Example 2

(18)

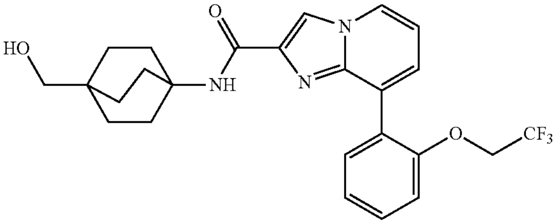

N-(4-(hydroxymethyl)bicyclo[2.2.2]octan-1-yl)-8-(2-(2,2,2-trifluoroethoxy)phenyl)imidazo[1,2-a]pyridine-2-carboxamide (18)

To a solution of methyl 4-(8-(2-(2,2,2-trifluoroethoxy)phenyl)imidazo[1,2-a]pyridine-2-carboxamido)bicyclo[2.2.2]octane-1-carboxylate (21 mg, 0.042 mmol) in THF (10 mL) at 0° C. was added a solution of LAH in THF (2 M, 42 μL, 0.084 mmol). The reaction mixture was warmed to ambient temperature and stirred an additional 10 min. The mixture was quenched with aqueous 1M HCl solution (10 mL) and partitioned between EtOAc (25 mL). The combined organic layers were concentrated, and the residue was purified using silica gel chromatography (4 g, 0-50% EtOAc: isohexane, 15 min) to give compound 18. MS: m/z=474.5 (M+1). $^1$H NMR (600 MHz, Methanol-$d_4$) δ 8.46 (d, J=6.8 Hz, 1H), 8.27 (s, 1H), 7.52-7.45 (m, 2H), 7.28 (d, J=6.9 Hz, 1H), 7.20 (t, J=7.9 Hz, 2H), 7.02 (t, J=6.9 Hz, 1H), 4.51 (q, J=8.5 Hz, 2H), 3.17 (s, 2H), 2.04-1.96 (m, 6H), 1.58-1.48 (m, 6H).

Example 3

(23)

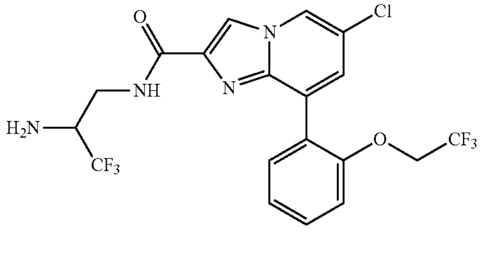

N-(2-amino-3,3,3-trifluoropropyl)-6-chloro-8-(2-(2,2,2-trifluoroethoxy)phenyl)imidazo[1,2-a]pyridine-2-carboxamide (23)

To a solution of tert-butyl (3-(6-chloro-8-(2-(2,2,2-trifluoroethoxy)phenyl)imidazo[1,2-a]pyridine-2-carboxamido)-1,1,1-trifluoropropan-2-yl)carbamate (70 mg, 0.12 mmol) in $CH_2Cl_2$ (2 mL) was added TFA (300 μL, 3.9 mmol). The reaction mixture was stirred at ambient temperature for 30 min. The mixture was then concentrated, and the residue was purified by HPLC (C18, 19×150 mm, 5-95 MeCN:water with 0.1% TFA, 25 min) to give compound 23. MS: m/z=481.4 (M+1). $^1$H NMR (600 MHz, Methanol-$d_4$) δ 8.72 (d, J=1.9 Hz, 1H), 8.42 (s, 1H), 7.60 (dd, J=7.5, 1.7 Hz, 1H), 7.51 (ddd, J=8.4, 7.5, 1.7 Hz, 1H), 7.43 (d, J=1.9 Hz, 1H), 7.27-7.16 (m, 2H), 4.56 (q, J=8.4 Hz, 2H), 4.32 (td, J=7.3, 4.7 Hz, 1H), 3.93-3.78 (m, 2H).

Example 4

(58)

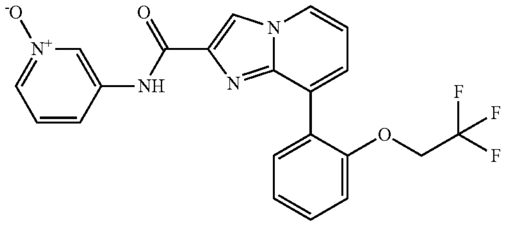

N-(1-oxidopyridin-1-ium-3-yl)-8-[2-(2,2,2-trifluoroethoxy)phenyl]imidazo[1,2-a]pyridine-2-carboxamide (58)

To a stirred solution of N-(pyridin-3-yl)-8-(2-(2,2,2-trifluoroethoxy)phenyl)imidazo[1,2-a]pyridine-2-carboxamide (83 mg, 0.20 mmol) in DCE (2 mL) was added m-CPBA (36 mg, 0.21 mmol). The reaction mixture was stirred at ambient temperature for 1 h. The mixture was quenched by saturated aqueous $Na_2S_2O_3$ solution (1 mL) and extracted with DCM (3×20 mL). The combined organic layers concentrated, and the residue was purified by prep-TLC (7% MeOH:$CH_2Cl_2$) to compound 58. MS: m/z=429.2 (M+1). $^1$H-NMR: (400 MHz, Methanol-$d_4$): δ 9.14 (s, 1H), 8.53-8.51 (m, 2H), 8.10-8.08 (m, 1H), 7.81-7.79 (m, 1H), 7.57-7.48 (m, 3H), 7.36-7.34 (m, 1H), 7.27-7.22 (m, 2H), 7.10-7.06 (m, 1H), 4.58-4.52 (m, 2H).

Example 5

(62)

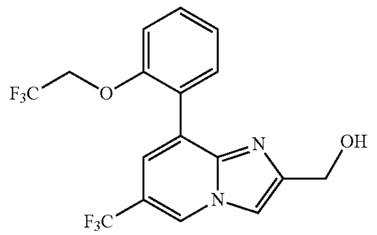

(8-(2-(2,2,2-trifluoroethoxy)phenyl)-6-(trifluoromethyl)imidazo[1,2-a]pyridin-2-yl)methanol (62)

To a solution of 8-(2-(2,2,2-trifluoroethoxy)phenyl)-6-(trifluoromethyl)imidazo[1,2-a]pyridine-2-carboxylic acid (20 mg, 0.049 mmol) in THF (300 μL) at 0° C. was added DIBAL (1.0 mL, 1.0 mmol) as a 1 M solution in THF. The reaction mixture was warmed to ambient and stirred for 2 h. The mixture was quenched with aqueous saturated $NH_4Cl$ solution (125 mL) and extracted with EtOAc (100 mL×3). The combined organic layers were concentrated, and the residue was purified by silica gel chromatography (4 g, 0-10% 10% MeOH/EtOAc to hexanes) to give compound 62. MS: m/z=391.2 (M+1). $^1H$ NMR (500 MHz, Chloroform-d) δ 8.48 (s, 1H), 7.77 (d, J=7.5 Hz, 1H), 7.70 (s, 1H), 7.47 (d, J=9.1 Hz, 2H), 7.23 (t, J=7.5 Hz, 1H), 7.05 (d, J=8.3 Hz, 1H), 4.84 (s, 2H), 4.39 (q, J=8.1 Hz, 2H), 2.55 (s, 1H).

Example 6

(63)

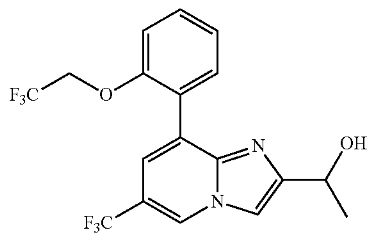

(R or S) 1-(8-(2-(2,2,2-trifluoroethoxy)phenyl)-6-(trifluoromethyl)imidazo[1,2-a]pyridin-2-yl)ethan-1-ol (63)

Step A: N-methoxy-N-methyl-8-(2-(2,2,2-trifluoroethoxy)phenyl)-6-(trifluoromethyl)imidazo[1,2-a]pidine-2-carboxamide (6-a)

To a solution of 8-(2-(2,2,2-trifluoroethoxy)phenyl)-6-(trifluoromethyl)imidazo[1,2-a]pyridine-2-carboxylic acid 234 mg, 0.579 mmol) in DMF (300 μL) was added N,O-dimethylhydroxylamine hydrochloride (70.6 mg, 0.724 mmol), PyBOP (377 mg, 0.724 mmol) and $Et_3N$ (triethylamine)(242 μL, 1.74 mmol). The reaction mixture was stirred for 1 h at ambient temperature. The mixture was purified by HPLC (30 cm×150 cm C18, 30 min 0-95% acetonitrile-water gradient, 0.05% TFA added) to give compound 6-a. MS: m/z=448.8 (M+1).

Step B: 1-(8-(2-(2,2,2-trifluoroethoxy)phenyl)-6-(trifluoromethyl)imidazo[1,2-a]pidin-2-yl)ethan-1-one (6-b)

To a solution of N-methoxy-N-methyl-8-(2-(2,2,2-trifluoroethoxy)phenyl)-6-(trifluoromethyl)imidazo[1,2-a]pidine-2-carboxamide (6-a, 210 mg, 0.470 mmol) in THF (2.35 mL) at 0° C. was added a solution of methylmagnesium bromide in diethyl ether (3 M, 1.570 mL, 4.69 mmol). The reaction mixture was slowly warmed to ambient temperature and stirred an additional 30 min. The mixture was partitioned between aqueous concentrated $NH_4Cl$ solution (5 mL) and EtOAc (5 mL×3). The combined organic layers were concentrated to give compound 6-b. MS: m/z=403.3 (M+1).

Step C: (R or S) 1-(8-(2-(2,2,2-trifluoroethoxy)phenyl)-6-(trifluoromethyl)imidazo[1,2-a]pidin-2-yl)ethan-1-ol (63)

To a solution of 1-(8-(2-(2,2,2-trifluoroethoxy)phenyl)-6-(trifluoromethyl)imidazo[1,2-a]pidin-2-yl)ethan-1-one (6-b, 170 mg, 0.420 mmol) in THF (4.2 mL) at 0° C. was added a solution of DIBAL in THF (1 M, 2.11 mL, 2.11 mmol). The reaction mixture was slowly warmed to ambient temperature and stirred for an additional 2 h. The mixture was quenched with concentrated aqueous Rochelle's salt solution (1 mL) and then extracted with EtOAc (1 mL×3). The combined organic layers were concentrated and the residue was purified by HPLC (30 cm×150 cm C18, 30 min 0-95% acetonitrile-water gradient, 0.05% TFA added). The enantiomeric mixture was separated by chiral chromatography using SFC (2 cm×15 cm IC, 100 bar, 10% iPrOH—$CO_2$) to give compound 63. MS: m/z=405.3 (M+1). $^1H$ NMR (500 MHz, $CDCl_3$) δ 8.49 (s, 1H), 7.71-7.63 (m, 2H), 7.50 (s, 1H), 7.45 (t, J=7.8 Hz, 1H), 7.20 (t, J=7.2 Hz, 1H), 7.02 (d, J=8.3 Hz, 1H), 5.06 (bs, 1H), 4.40 (m, 2H), 4.00 (hept, J=6.1 Hz, 1H), 1.19 (d, J=6.1 Hz, 3H).

Compounds 64 and 65 found in Table 2 were prepared in analogous fashion to that described in Example 6 above.

TABLE 2

| Compoud Number | Structure | Compound Name | MS: m/z (M + 1) |
|---|---|---|---|
| 64 | 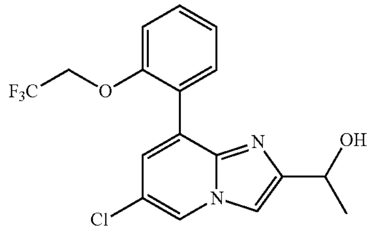 [SMILES: CC(O)c1cn2cc(Cl)cc(-c3ccccc3OCC(F)(F)F)c2n1] | 1-[6-chloro-8-[2-(2,2,2-trifluoroethoxy)phenyl]imidazo[1,2-a]pyridin-2-yl]ethanol | 371.3 |
| 65 | 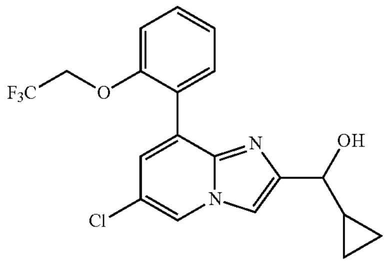 [SMILES: OC(c1cn2cc(Cl)cc(-c3ccccc3OCC(F)(F)F)c2n1)C1CC1] | [6-chloro-8-[2-(2,2,2-trifluoroethoxy)phenyl]imidazo[1,2-a]pyridin-2-yl]-cyclopropyl-methanol | 397.1 |

Example 7

(66)

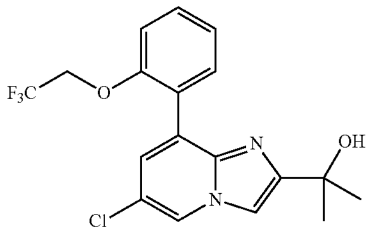

2-(6-chloro-8-(2-(2,2,2-trifluoroethoxy)phenyl)imidazo[1,2-a]pyridin-2-yl)propan-2-ol (66)

To a solution of ethyl 6-chloro-8-(2-(2,2,2-trifluoroethoxy)phenyl)imidazo[1,2-a]pyridine-2-carboxylate (260 mg, 0.90 mmol) and (2-(2,2,2-trifluoroethoxy)phenyl)boronic acid (178 mg, 0.808 mmol) in THF (3.6 mL) was added XPhos G3 precatalyst (76 mg, 0.090 mmol) and 1 N potassium phosphate solution (2.69 mL, 2.69 mmol). The reaction mixture was sealed and heated at 45° C. for 6 h. The organic layer was separated, then concentrated. The residue was purified by HPLC (30 cm×150 cm C18, 30 min 0-95% acetonitrile-water gradient, 0.05% TFA added) to give the title compound. MS: m/z=385.1 (M+1). $^1$H NMR (500 MHz, Methonal-$d_4$) δ 9.02 (d, J=1.5 Hz, 1H), 8.15 (s, 1H), 7.93 (d, J=1.8 Hz, 1H), 7.72-7.64 (m, 1H), 7.57 (dd, J=7.5, 1.4 Hz, 1H), 7.35-7.28 (m, 2H), 4.63 (q, J=8.4 Hz, 2H), 1.65 (s, 6H).

Example 8

(67)

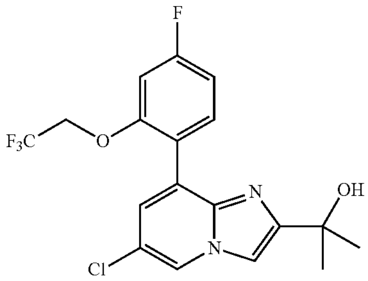

2-(6-chloro-8-(4-fluoro-2-(2,2,2-trifluoroethoxy)phenyl)imidazo[1,2-a]pyridin-2-yl) propan-2-ol (67)

To a solution of ethyl 6-chloro-8-(4-fluoro-2-(2,2,2-trifluoroethoxy)phenyl)imidazo[1,2-a]pyridine-2-carboxylate (I3, 90 mg, 0.22 mmol) in THF (2.2 mL) at 0° C. was added a solution of methylmagnesium bromide in diethyl ether (3 M, 216 μL, 0.648 mmol). The reaction mixture was stirred at 0° C. for 1 h, quenched with aqueous saturated $NH_4Cl$ solution (2 mL), and then extracted with EtOAc (2 mL×3). The combined organic layers were concentrated, and the residue was purified by HPLC (30 cm×150 cm C18, 30 min 0-95% acetonitrile-water gradient, 0.05% TFA added) to give compound 67. MS: m/z=403.3 (M+1). $^1$H NMR (500 MHz, Chloroform-d) δ 8.37 (d, J=1.6 Hz, 1H), 7.59 (d, J=1.9 Hz, 2H), 7.29 (dd, J=8.4, 6.2 Hz, 1H), 6.90 (td, J=8.2, 2.2 Hz, 1H), 6.75 (dd, J=10.1, 2.1 Hz, 1H), 4.50 (q, J=7.9 Hz, 2H), 1.68 (s, 6H).

Example 9

(68)

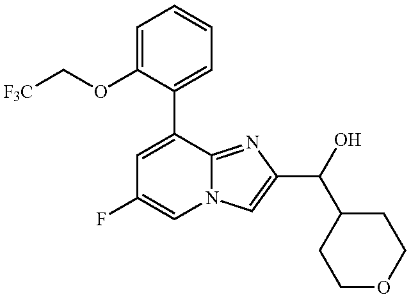

(6-fluoro-8-(2-(2,2,2-trifluoroethoxy)phenyl)imidazo[1,2-a]pyridin-2-yl)(tetrahydro-2H-pyran-4-yl)methanol (68)

Step A: 6-fluoro-2-((tetrahydro-4H-pyran-4-ylidene)methyl)-8-(2-(2,2,2-trifluoroethoxy)phenyl)imidazo[1,2-a]pyridine (9-a)

To a solution of 2-bromo-6-fluoro-8-(2-(2,2,2-trifluoroethoxy)phenyl)imidazo[1,2-a]pyridine (I2, 62 mg, 0.16 mmol) and 4,4,5,5-tetramethyl-2-((tetrahydro-4H-pyran-4-ylidene)methyl)-1,3,2-dioxaborolane (71 mg, 0.32 mmol) in THF (0.6 mL) was added XPhos G3 precatalyst (13 mg, 0.016 mmol) and aqueous 1 N potassium phosphate solution (480 μL, 0.48 mmol). The reaction mixture was sealed under nitrogen and heated at 80° C. for 6 h. The mixture was cooled, and the organic layer was separated and concentrated. The residue was purified by HPLC (19 cm×150 cm C18, 30 min 0-95% acetonitrile-water gradient, 0.05% TFA added) to give compound 9-a. MS: m/z=407.3 (M+1).

Step B: (6-fluoro-8-(2-(2,2,2-trifluoroethoxy)phenyl)imidazo[1,2-a]pyridin-2-yl)(tetrahydro-2H-pyran-4-yl)methanol (68)

To a solution of 6-fluoro-2-((tetrahydro-4H-pyran-4-ylidene)methyl)-8-(2-(2,2,2-trifluoroethoxy)phenyl)imidazo[1,2-a]pidine (30 mg, 0.074 mmol) in THF at 0° C. was added a solution of $BH_3$ in THF (1 M, 221 μL, 0.221 mmol). The reaction was warmed to ambient temperature and stirred for 2 h, and then cooled to 0° C. Aqueous 40% $H_2O_2$ solution (65 μL, 0.74 mmol) and aqueous NaOH solution (2 N, 295 μL, 0.591 mmol) were added, and the mixture was warmed to ambient temperature and stirred for 1 h. The mixture was neutralized with aqueous saturated $NH_4Cl$ solution (1 mL), extracted with EtOAc (2 mL×3) and concentrated. The residue was purified by HPLC (19 cm×150 cm C18, 30 min 0-95% acetonitrile-water gradient, 0.05% TFA added) to give compound 68. MS: m/z=425.3 (M+1). $^1H$ NMR (500 MHz, Chloroform-d) δ 8.32 (t, J=2.0 Hz, 1H), 7.76 (s, 1H), 7.63 (dd, J=8.2, 2.0 Hz, 1H), 7.61-7.53 (m, 1H), 7.33 (m, 1H), 7.22 (t, J=7.4 Hz, 1H), 7.01 (d, J=8.4 Hz, 1H), 4.67 (d, J=8.5 Hz, 1H), 4.57-4.38 (m, 2H), 4.05 (dd, J=11.6, 3.4 Hz, 1H), 3.96 (dd, J=11.5, 3.4 Hz, 1H), 3.41-3.29 (m, 2H), 2.19-2.08 (m, 1H), 1.91 (d, J=13.2 Hz, 1H), 1.45 (dqd, J=42.0, 12.4, 4.5 Hz, 2H), 1.24 (d, J=15.2 Hz, 1H).

Example 10

(69)

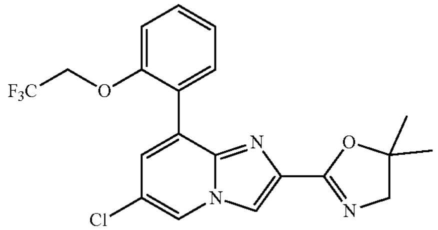

2-(6-chloro-8-(2-(2,2,2-trifluoroethoxy)phenyl)imidazo[1,2-a]pyridin-2-yl)-5,5-dimethyl-4,5-dihydrooxazole (69)

To a suspension of 6-chloro-8-(2-(2,2,2-trifluoroethoxy)phenyl)imidazo[1,2-a]pyridine-2-carboxylic acid (43 mg, 0.12 mmol) in $CH_2Cl_2$ (0.6 mL) was added 1-chloro-N,N,2-trimethylpropenylamine (46 μL, 0.35 mol). After 30 min, 1-amino-2-methylpropan-2-ol (13 μL, 0.13 mmol) and pyridine (28 μL, 0.35 mmol) were added. The reaction mixture was stirred for 1 h at ambient temperature, concentrated and diluted with pyridine (0.5 mL). Triphenyl phosphite (91 μL, 0.35 mmol) was added, and the resulting mixture was sealed and heated at 125° C. for 5 h. The mixture was concentrated and purified by HPLC (19 cm×150 cm C18, 30 min 0-95% acetonitrile-water gradient, 0.05% TFA added) to give compound (69). MS: m/z=424.1 (M+1). $^1H$ NMR (500 MHz, Methanol-$d_4$) δ 8.74 (d, J=1.6 Hz, 1H), 8.38 (s, 1H), 7.55 (d, J=7.5 Hz, 1H), 7.50 (t, J=7.9 Hz, 1H), 7.44 (d, J=1.6 Hz, 1H), 7.24-7.15 (m, 2H), 4.56 (q, J=8.4 Hz, 2H), 3.92 (s, 2H), 1.75 (s, 6H).

Compound 70 as shown in Table 3, was prepared in an analogous fashion to that described in Example 10 for compound 69.

TABLE 3

| Compoud. Number | Structure | Compound Name | MS: m/z (M + 1) |
|---|---|---|---|
| 70 | 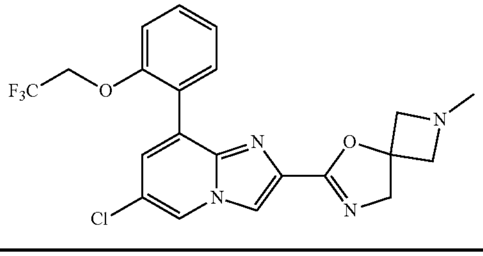 | 6-[6-chloro-8-[2-(2,2,2-trifluoroethoxy)phenyl]imidazo[1,2-a]pyridin-2-yl]-2-methyl-5-oxa-2,7-diazaspiro[3.4]oct-6-ene | 451.4 |

Example 11

(71)

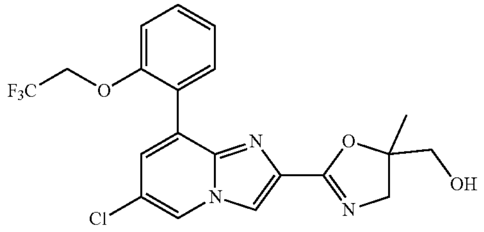

(2-(6-chloro-8-(2-(2,2,2-trifluoroethoxy)phenyl)imidazo[1,2-a]pyridin-2-yl)-5-methyl-4,5-dihydrooxazol-5-yl)methanol (71)

Step A: methyl 3-(6-chloro-8-(2-(2,2,2-trifluoroethoxy)phenyl)imidazo[1,2-a]pyridine-2-carboxamido)-2-hydroxy-2-methylpropanoate (11-a)

To a suspension of 6-chloro-8-(2-(2,2,2-trifluoroethoxy) phenyl)imidazo[1,2-a]pyridine-2-carboxylic acid (100 mg, 0.270 mmol) in DMF (1.35 mL) was added methyl 3-amino-2-hydroxy-2-methylpropanoate hydrochloride (57 mg, 0.34 mmol), $Et_3N$ (113 μL, 0.809 mmol), and HATU (205 mg, 0.540 mmol). The reaction mixture was stirred for 30 min at ambient temperature, then purified by HPLC (30 cm×150 cm C18, 30 min 0-95% acetonitrile-water gradient, 0.05% TFA added) to give compound 11-a. MS: m/z=486.4 (M+1).

Step B: methyl 2-(6-chloro-8-(2-(2,2,2-trifluoroethoxy)phenyl)imidazo[1,2-a]pyridin-2-yl)-5-methyl-4,5-dihydrooxazole-5-carboxylate (11-b)

To a solution of methyl 3-(6-chloro-8-(2-(2,2,2-trifluoroethoxy)phenyl)imidazo[1,2-a]pyridine-2-carboxamido)-2-hydroxy-2-methylpropanoate (11-a, 115 mg, 0.237 mmol) in $CH_2Cl_2$ (1.2 mL) was added DBU (178 μL, 1.18 mmol) and nonafluorobutanesulfonyl fluoride (213 μL, 1.18 mmol). The reaction mixture was stirred at ambient temperature for 12 h, then concentrated. The residue was purified by silica gel chromatography (0-35% EtOAc:hexanes) to give compound 11-b. MS: m/z=468.3 (M+1).

Step C: (2-(6-chloro-8-(2-(2,2,2-trifluoroethoxy) phenyl)imidazo[1,2-a]pyridin-2-yl)-5-methyl-4,5-dihydrooxazol-5-yl)methanol (71)

To a solution of methyl 2-(6-chloro-8-(2-(2,2,2-trifluoroethoxy)phenyl)imidazo[1,2-a]pyridin-2-yl)-5-methyl-4,5-dihydrooxazole-5-carboxylate (11-b, 85 mg, 0.18 mmol) in THF (1.8 mL) at 0° C., was added a solution of LAH in THF (2 M, 114 μL, 0.227 mmol). The reaction mixture was allowed to slowly warm to ambient temperature, and then stirred for 2 h. The mixture was then quenched with saturated aqueous potassium sodium tartrate solution (5 mL), and extracted with EtOAc (5 mL×3). The combined organic layers were concentrated, and the residue was purified by HPLC (19 cm×150 cm C18, 30 min 0-95% acetonitrile-water gradient, 0.1% TFA added to give compound 71. MS: m/z=440.3 (M+1). $^1$H NMR (500 MHz, Chloroform-d) δ 8.17 (s, 1H), 8.06 (s, 1H), 7.66 (d, J=7.3 Hz, 1H), 7.42 (t, J=7.7 Hz, 1H), 7.31 (s, 1H), 7.18 (t, J=7.1 Hz, 1H), 7.04 (d, J=8.2 Hz, 1H), 4.44 (q, J=8.0 Hz, 2H), 3.96 (d, J=14.6 Hz, 1H), 3.69 (d, J=14.5 Hz, 1H), 3.65-3.49 (m, 2H), 1.43 (s, 3H).

Compounds 72 and 73 found in Table 4 were prepared in analogous fashion to that described in Example 11 for compound 71.

TABLE 4

| Compoud Number | Structure | Compound | MS: m/z (M + 1) |
|---|---|---|---|
| 72 | 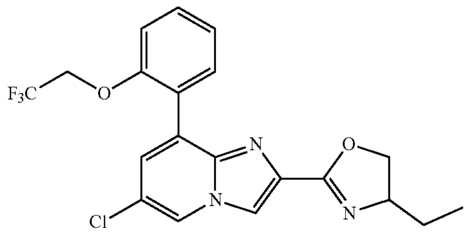 [SMILES: CCC1COC(c2cn3cc(Cl)cc(-c4ccccc4OCC(F)(F)F)c3n2)=N1] | [2-[6-chloro-8-[2-(2,2,2-trifluoroethoxy)phenyl]imidazo [1,2-a]pyridin-2-yl]-4,5-dihydrooxazol-4-yl]methanol | 426.3 |
| 73 | 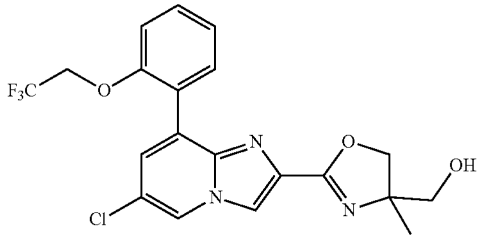 [SMILES: CC1(CO)COC(c2cn3cc(Cl)cc(-c4ccccc4OCC(F)(F)F)c3n2)=N1] | [2-[6-chloro-8-[2-(2,2,2-trifluoroethoxy)phenyl]imidazo [1,2-a]pyridin-2-yl]-4-methyl-5H-oxazol-4-yl]methanol | 440.4 |

Example 12

(74)

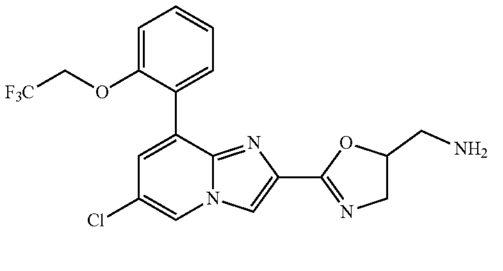

(2-(6-chloro-8-(2-(2,2,2-trifluoroethoxy)phenyl)imidazo[1,2-a]pyridin-2-yl)-4,5-dihydrooxazol-5-yl) methanamine (74)

Step A: tert-butyl (2-(6-chloro-8-(2-(2,2,2-trifluoroethoxy)phenyl)imidazo[1,2-a]pyridine-2-carboxamido)-1-hydroxyethyl)carbamate (12-a)

To a suspension of 6-chloro-8-(2-(2,2,2-trifluoroethoxy) phenyl)imidazo[1,2-a]pyridine-2-carboxylic acid (1.0 g, 2.70 mmol) and tert-butyl(3-amino-2-hydroxypropyl)carbamate (565 mg, 2.97 mmol) in DMF (13.5 mL) was added PyBOP (1.69 g, 3.24 mmol) and $Et_3N$ (1.13 mL, 8.09 mmol). The reaction mixture was stirred for 30 min, then purified by HPLC (30 cm×150 cm C18, 30 min 0-95% acetonitrile-water gradient, 0.05% TFA added) to give compound 12-a. MS: m/z=545.5 (M+1).

Step B: tert-butyl ((2-(6-chloro-8-(2-(2,2,2-trifluoroethoxy)phenyl)imidazo[1,2-a]pyridin-2-yl)-4,5-dihydrooxazol-5-yl)methyl)carbamate (12-b)

To a solution of tert-butyl (2-(6-chloro-8-(2-(2,2,2-trifluoroethoxy)phenyl)imidazo[1,2-a]pyridine-2-carboxamido)-1-hydroxyethyl)carbamate (12-a, 1.0 g, 1.84 mmol) in $CH_2Cl_2$ (9.2 mL) was added DBU (1.39 mL, 9.21 mmol) and nonafluorobutanesulfonyl fluoride (1.65 mL, 9.21 mmol). The reaction mixture was stirred at ambient temperature for 12 h, then concentrated. The residue was purified by silica gel chromatography (0-3% MeOH:DCM) to give compound 12-b. MS: m/z=525.5 (M+1).

Step C: (2-(6-chloro-8-(2-(2,2,2-trifluoroethoxy) phenyl)imidazo[1,2-a]pidin-2-yl)-4,5-dihydrooxazol-5-yl)methanamine (74)

To a solution of tert-butyl ((2-(6-chloro-8-(2-(2,2,2-trifluoroethoxy)phenyl)imidazo[1,2-a]pyridin-2-yl)-4,5-dihydrooxazol-5-yl)methyl)carbamate (12-b, 50 mg, 0.095 mmol) in $CH_2Cl_2$ (1 mL) at 0° C., TMSI was added (26 μL, 0.19 mmol). The reaction mixture was stirred for 1 min and then purified by silica gel chromatography (0-5% MeOH: DCM, 4 g silica gel) to give compound 74. MS: m/z=425.4 (M+1). $^1H$ NMR (500 MHz, Methanol-$d_4$) δ 8.74 (s, 1H), 8.67 (s, 1H), 7.59 (d, J=7.4 Hz, 1H), 7.54 (t, J=7.8 Hz, 1H), 7.48 (s, 1H), 7.29-7.19 (m, 2H), 5.54 (s, 1H), 4.59 (q, J=8.5 Hz, 2H), 3.41 (d, J=13.8 Hz, 2H), 3.38-3.33 (m, 2H).

Example 13

(75)

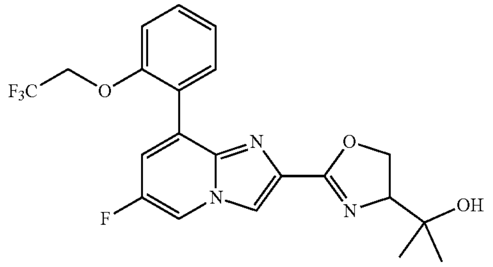

2-(2-(6-chloro-8-(2-(2,2,2-trifluoroethoxy)phenyl) imidazo[1,2-a]pyridin-2-yl)-4,5-dihydrooxazol-4-yl) propan-2-ol (75)

Step A: methyl (6-chloro-8-(2-(2,2,2-trifluoroethoxy)phenyl)imidazo[1,2-a]pyridine-2-carbonyl)serinate (13-a)

To a solution of 6-chloro-8-(2-(2,2,2-trifluoroethoxy)phenyl)imidazo[1,2-a]pyridine-2-carboxylic acid (1.00 g, 2.70 mmol) in DMF (13.5 mL) was added methyl serinate hydrochloride (500 mg, 3.2 mmol), PyBOP (1.760 g, 3.37 mmol) and $Et_3N$ (1.13 mL, 8.09 mmol). The reaction mixture was stirred for 1 h at ambient temperature, then purified by HPLC (30 cm×150 cm C18, 30 min 0-95% acetonitrile-water gradient, 0.05% TFA added) to give compound 13-a. MS: m/z=472.4 (M+1).

Step B: methyl 2-(6-chloro-8-(2-(2,2,2-trifluoroethoxy)phenyl)imidazo[1,2-a]pyridin-2-yl)-4,5-dihydrooxazole-4-carboxylate (13-b)

To a solution of methyl (6-chloro-8-(2-(2,2,2-trifluoroethoxy)phenyl)imidazo[1,2-a]pyridine-2-carbonyl)serinate (13-a, 500 mg, 1.06 mmol) in $CH_2Cl_2$ (5.3 mL) was added DBU (800 μL, 5.30 mmol) and nonafluorobutanesulfonyl fluoride (950 μL, 5.30 mmol). The reaction mixture was stirred at ambient temperature for 12 h, then concentrated. The residue was purified by silica gel chromatography (0-5% MeOH:DCM) to give compound (13-b). MS: m/z=454.4 (M+1).

Step C: 2-(2-(6-chloro-8-(2-(2,2,2-trifluoroethoxy) phenyl)imidazo[1,2-a]pyridin-2-yl)-4,5-dihydrooxazol-4-yl)propan-2-ol (75)

To a solution of methyl 2-(6-chloro-8-(2-(2,2,2-trifluoroethoxy)phenyl)imidazo[1,2-a]pyridin-2-yl)-4,5-dihydrooxazole-4-carboxylate (13-b, 50 mg, 0.11 mmol) in THF (1.1 mL) was added a solution of methylmagnesium bromide in diethyl ether (3 M, 110 μL, 0.33 mmol). The reaction mixture was stirred for 30 min at 0° C. The mixture was then quenched with concentrated aqueous $NaHCO_3$ solution (2 mL), and extracted with EtOAC (2 mL×3). The combined organic layers were concentrated, and the residue was purified by silica gel chromatography (0-5% MeOH:DCM, 4 g silica gel) to give compound 75. MS: m/z=454.4 (M+1). $^1H$ NMR (500 MHz, Chloroform-d) δ 8.19 (s, 1H), 8.12 (s, 1H), 7.68 (d, J=7.4 Hz, 1H), 7.40 (t, J=7.7 Hz, 1H), 7.31 (s, 1H), 7.17 (t, J=7.4 Hz, 1H), 7.03 (d, J=8.2 Hz, 1H), 4.53-4.40 (m, 3H), 4.34 (t, J=8.4 Hz, 1H), 4.25 (t, J=9.2 Hz, 1H), 2.07 (s, 1H), 1.33 (s, 3H), 1.17 (s, 3H).

Compounds 76, 77, and 78, as shown in Table 5 were prepared in analogous fashion to that described for Example 13, compound 75.

TABLE 5

| Compoud. Number | Structure | Compound Name | MS: m/z (M + 1) |
|---|---|---|---|
| 76 | 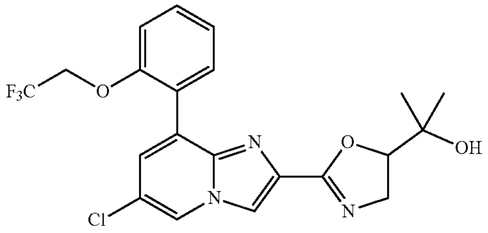 [SMILES: CC(C)(O)C1CN=C(c2cn3cc(Cl)cc(-c4ccccc4OCC(F)(F)F)c3n2)O1] | 2-[2-[6-chloro-8-[2-(2,2,2-trifluoroethoxy)phenyl]imidazo [1,2-a]pyridin-2-yl]-4,5-dihydrooxazol-5-yl]propan-2-ol | 454.4 |
| 77 | 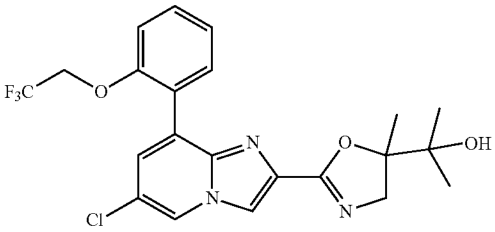 [SMILES: CC(C)(O)C1(C)CN=C(c2cn3cc(Cl)cc(-c4ccccc4OCC(F)(F)F)c3n2)O1] | 2-[2-[6-chloro-8-[2-(2,2,2-trifluoroethoxy)phenyl]imidazo [1,2-a]pyridin-2-yl]-5-methyl-4H-oxazol-5-yl]propan-2-ol | 468.4 |
| 78 | 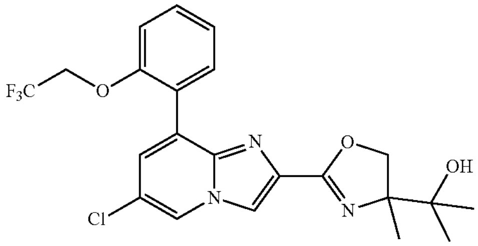 [SMILES: CC(C)(O)C1(C)COC(c2cn3cc(Cl)cc(-c4ccccc4OCC(F)(F)F)c3n2)=N1] | 2-[2-[6-chloro-8-[2-(2,2,2-trifluoroethoxy)phenyl]imidazo [1,2-a]pyridin-2-yl]-4-methyl-5H-oxazol-4-yl]propan-2-ol | 468.4 |

Example 14

(79)

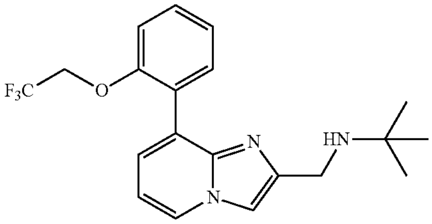

2-methyl-N-((8-(2-(2,2,2-trifluoroethoxy)phenyl) imidazo[1,2-a]pyridin-2-yl)methyl)propan-2-amine (79)

Step A: N-((8-bromoimidazo[1,2-a]pyridin-2-yl) methyl)-2-methylpropan-2-amine (14-a)

To a solution of 8-bromoimidazo[1,2-a]pyridine-2-carbaldehyde (75 mg, 0.33 mmol) and 2-methylpropan-2-amine (16 mg, 0.22 mmol) in DCE (3 mL) was added AcOH (13 μL, 0.22 mmol). The mixture stirred at ambient temperature for 10 min before $NaBH_3CN$ (42 mg, 0.67 mmol) was added. The resulting mixture was stirred for 2 h, quenched with saturated aqueous $NaHCO_3$ solution (20 mL), and then extracted with EtOAc (5 mL×3). The combined organic layers were concentrated to give compound 14-a. MS: m/z=282.2 (M+1).

Step B: 2-methyl-N-((8-(2-(2,2,2-trifluoroethoxy) phenyl)imidazo[1,2-a]pyridin-2-yl)methyl)propan-2-amine (79)

To a solution of (2-(2,2,2-trifluoroethoxy)phenyl)boronic acid (63 mg, 0.29 mmol), XPhos-G3-Pd precatalyst (19 mg, 0.022 mmol, Sigma-Aldrich Corp., St. Louis, MO, USA), and N-((8-bromoimidazo[1,2-a]pyridin-2-yl)methyl)-2-methylpropan-2-amine (14-a, 63 mg, 0.22 mmol) in THF (2 mL) was added aqueous potassium phosphate solution (1 N, 670 μL, 0.67 mmol). The reaction mixture was sealed under nitrogen and heated at 80° C. for 16 h. The organic layer was separated and concentrated, and the residue was purified by HPLC (C18, 30×150 mm, 5-95% MeCN:water with 0.1% TFA, 25 min) to give compound 79. MS: m/z=378.4 (M+1). $^1H$ NMR (500 MHz, Methanol-$d_4$) δ 8.74-8.65 (m, 1H), 8.28 (s, 1H), 7.69 (d, J=7.2 Hz, 1H), 7.62-7.50 (m, 2H), 7.37 (t, J=7.0 Hz, 1H), 7.27 (d, J=7.9 Hz, 2H), 4.60 (q, J=8.4 Hz, 2H), 4.43 (s, 2H), 1.46 (s, 9).

Example 15

(80)

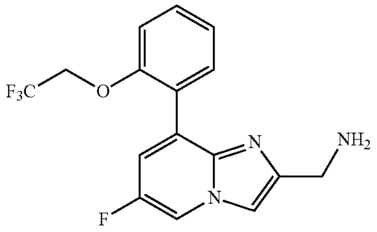

(8-(2-(2,2,2-trifluoroethoxy)phenyl)imidazo[1,2-a]pyridin-2-yl)methanamine (80)

Step A: tert-butyl ((8-bromoimidazo[1,2-a]pyridin-2-yl)methyl)carbamate (15-a)

To a solution of (8-bromoimidazo[1,2-a]pyridin-2-yl)methanamine (100 mg, 0.44 mmol) in DCM (1 mL) was added $Et_3N$ (80 μL, 0.58 mmol) and $BOC_2O$ (110 μL, 0.49 mmol). The reaction mixture was stirred at ambient temperature for 12 h. The mixture was quenched with saturated aqueous $NaHCO_3$ solution (2 mL) and extracted with EtOAc (5 mL×3). The combined organic layers were concentrated to give compound 15-a. MS: m/z=326.3 (M+1).

Step B: tert-butyl ((8-(2-(2,2,2-trifluoroethoxy)phenyl)imidazo[1,2-a]pyridin-2-yl)methyl)carbamate (15-b)

To a solution of (2-(2,2,2-trifluoroethoxy)phenyl)boronic acid (110 mg, 0.51 mmol), tert-butyl ((8-bromoimidazo[1,2-a]pyridin-2-yl)methyl)carbamate (15-a, 140 mg, 0.42 mmol), and XPhos G3 precatalyst (36 mg, 0.042 mmol) in THF (2 mL) was added aqueous potassium phosphate solution (1 N, 1.3 mL, 1.3 mmol). The reaction mixture was sealed under nitrogen and heated at 80° C. for 16 h. The organic layer was separated and concentrated, and the residue was purified by HPLC (C18, 30×150 mm, 5-95% MeCN:water with 0.1% TFA, 25 min) to give compound 15-b. MS: m/z=422.4 (M+1).

Step C: (8-(2-(2,2,2-trifluoroethoxy)phenyl)imidazo[1,2-a]pyridin-2-yl)methanamine (80)

To a solution of tert-butyl ((8-(2-(2,2,2-trifluoroethoxy)phenyl)imidazo[1,2-a]pyridin-2-yl)methyl)carbamate (15-b, 17 mg, 0.041 mmol) in $CH_2Cl_2$ (3 mL) was added TFA (3 μL, 0.04 mmol). The reaction mixture was stirred for 30 min, then concentrated. The residue was purified by HPLC (C18, 30×150 mm, 5-95% MeCN:water with 0.1% TFA, 25 min) to give compound (80). MS: m/z=322.3 (M+1). $^1H$ NMR (500 MHz, Methanol-$d_4$) δ 8.77 (d, J=6.6 Hz, 1H), 8.31 (s, 1H), 7.83 (d, J=7.2 Hz, 1H), 7.65-7.59 (m, 1H), 7.56 (dd, J=7.8, 1.5 Hz, 1H), 7.49 (t, J=7.0 Hz, 1H), 7.29 (t, J=7.4 Hz, 2H), 4.63 (q, J=8.4 Hz, 2H), 4.40 (s, 2H).

Example 16

(81)

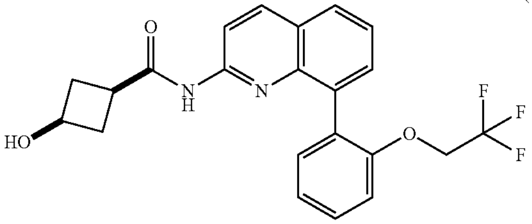

cis-3-hydroxy-N-(8-(2-(2,2,2-trifluoroethoxy)phenyl)quinolin-2-yl)cyclobutane-1-carboxamide (81)

Step A: cis-N-(8-bromoquinolin-2-yl)-3-hydroxycyclobutane-1-carboxamide (16-a)

A mixture of 8-bromoquinolin-2-amine (50 mg, 0.22 mmol), cis-3-hydroxycyclobutane-1-carboxylic acid (31 mg, 0.27 mmol), EDC (64 mg, 0.34 mmol), HOAt (37 mg, 0.27 mmol), and TEA (0.12 mL, 0.90 mmol) in DMF (5 mL) was heated at 50° C. for 30 min. The mixture was concentrated, then the residue was partitioned between brine and dichloromethane. The organic layer was purified by column chromatography on silica gel (DCM, grading to 10% MeOH/DCM) to provide compound 16-a. MS: m/z=321.2 (M+1).

Step B: cis-3-hydroxy-N-(8-(2-(2,2,2-trifluoroethoxy)phenyl)quinolin-2-yl)cyclobutane-1-carboxamide (81)

A mixture of cis-N-(8-bromoquinolin-2-yl)-3-hydroxycyclobutane-1-carboxamide (16-a, 10 mg, 0.032 mmol), (2-(2,2,2-trifluoroethoxy)phenyl)boronic acid (74 mg, 0.34 mmol), aqueous potassium phosphate solution (1 N, 0.10 mL, 0.10 mmol), and XPhos G3 precatalyst (3 mg, 0.003 mmol) in THF (1 mL) was heated under nitrogen at 80° C. for 16 h. The mixture was cooled, filtered, and concentrated. The residue purified by column chromatography on silica gel (DCM, grading to 10% MeOH/DCM) to give compound 81. MS: m/z=417.4 (M+1). $^1H$ NMR (600 MHz, Methanol-$d_4$) δ 8.26 (d, J=8.8 Hz, 1H), 7.84 (dd, J=8.1, 1.4 Hz, 1H), 7.55 (dd, J=7.1, 1.5 Hz, 1H), 7.51-7.46 (m, 1H), 7.44-7.38 (m, 1H), 7.32 (dd, J=7.3, 1.6 Hz, 1H), 7.15 (t, J=8.0 Hz, 2H), 4.38 (q, J=8.6 Hz, 2H), 4.09 (q, J=7.1 Hz, 1H), 2.71 (s, 1H), 2.44 (s, 2H), 2.14 (d, J=7.5 Hz, 1H).

Compounds 82 and 83 shown in Table 6 were prepared from the appropriate corresponding 2-amino-8-bromoquinolines by reversing the order of Steps A and B described for compound 81 of Example 16.

TABLE 6

| Compoud. Number | Structure | Compound Name | MS: m/z (M + 1) |
| --- | --- | --- | --- |
| 82 | 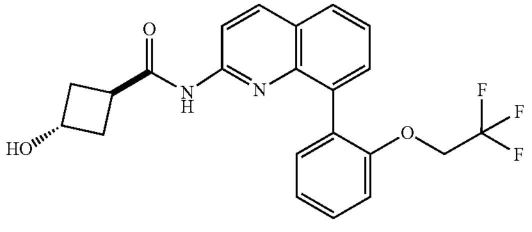 [SMILES: O=C(Nc1ccc2cccc(-c3ccccc3OCC(F)(F)F)c2n1)[C@H]1C[C@H](O)C1] | trans-3-hydroxy-N-(8-(2-(2,2,2-trifluoroethoxy)phenyl)quinolin-2-yl)cyclobutane-1-carboxamide | 417.3 |
| 83 | 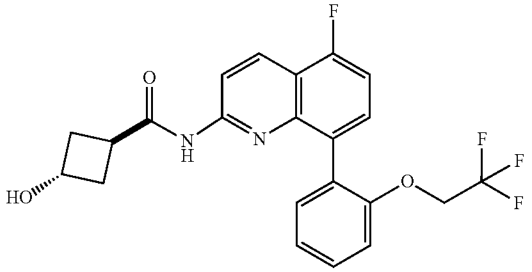 [SMILES: O=C(Nc1ccc2c(F)ccc(-c3ccccc3OCC(F)(F)F)c2n1)[C@H]1C[C@H](O)C1] | trans-N-(5-fluoro-8-(2-(2,2,2-trifluoroethoxy)phenyl)quinolin-2-yl)-3-hydroxycyclobutane-1-carboxamide | 435.1 |

Example 17

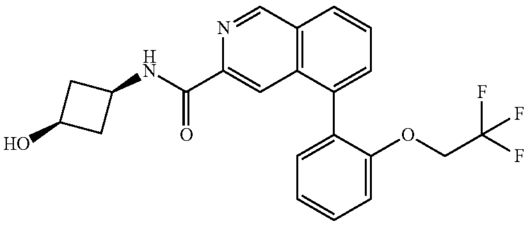 [SMILES: O=C(N[C@H]1C[C@@H](O)C1)c1cc2c(-c3ccccc3OCC(F)(F)F)cccc2cn1]

N-cis-3-hydroxycyclobutyl)-5-(2-(2,2,2-trifluoroethoxy)phenyl)isoquinoline-3-carboxamide (84)

Step A: ethyl 5-bromoisoquinoline-3-carboxylate (17-a)

A mixture of 5-bromoisoquinoline-3-carboxylic acid (500 mg, 1.984 mmol), aqueous concentrated sulfuric acid (18.8 M, 0.106 mL, 1.98 mmol) and EtOH (7 mL) was heated at reflux for 16 h. The mixture was cooled and concentrated, and the residue was carefully partitioned between ethyl acetate and aqueous saturated sodium bicarbonate solution. The organic layer was washed with water, brine, and then dried over sodium sulfate and further concentrated to afford compound 17-a. MS: m/z=282.2 (M+1).

Step B: ethyl 5-(2-(2,2,2-trifluoroethoxy)phenyl) isoquinoline-3-carboxylate (17-b)

A mixture of ethyl 5-bromoisoquinoline-3-carboxylate (17-a, 465 mg, 1.66 mmol), (2-(2,2,2-trifluoroethoxy)phenyl)boronic acid (548 mg, 2.49 mmol), aqueous potassium phosphate solution (1 N, 4.98 mL, 4.98 mmol), and XPhos Pd G3 (141 mg, 0.166 mmol) in THF (8 mL) was heated under nitrogen at 80° C. for 16 h. The mixture was cooled, filtered, and concentrated. The residue purified by column chromatography on silica gel (hexanes, grading to 50% EtOAc) to give compound 17-b. MS: m/z=376.4 (M+1).

Step C: 5-(2-(2,2,2-trifluoroethoxy)phenyl)isoquinoline-3-carboxylic acid (17-c)

A solution of ethyl 5-(2-(2,2,2-trifluoroethoxy)phenyl) isoquinoline-3-carboxylate (17-b, 520 mg, 1.38 mmol) and aqueous 1 N NaOH solution (4.16 mL, 4.16 mmol) in a 1:1 mixture of THF and MeOH (6 mL) was stirred at 23° C. for 2 h. The mixture was concentrated, and the residue acidified with aqueous 1M HCl solution (4.16 mL, 4.16 mmol), then partitioned between EtOAc (3×). The combined organic layers were washed with brine, dried over sodium sulfate, and concentrated to give compound 17-c. MS: m/z=348.3 (M+1).

Step D: N-cis-3-hydroxycyclobutyl)-5-(2-(2,2,2-trifluoroethoxy)phenyl)isoquinoline-3-carboxamide (84)

A mixture of (1s,3s)-3-aminocyclobutan-1-ol hydrochloride (27 mg, 0.22 mmol), 5-(2-(2,2,2-trifluoroethoxy)phenyl)isoquinoline-3-carboxylic acid (70 mg, 0.20 mmol), EDC (58 mg, 0.30 mmol), HOAt (33 mg, 0.24 mmol), and TEA (0.084 mL, 0.60 mmol) in DMF (5 mL) was stirred at 23° C. for 16 h. The mixture was concentrated, and residue purified by column chromatography on silica gel (hexanes, grading to 50% EtOAc) to provide compound 84. MS: m/z=417.4 (M+1). $^1$H NMR (600 MHz, Methanol-$d_4$) δ 9.30 (s, 1H), 8.16 (d, J=6.9 Hz, 2H), 7.81 (t, J=7.7 Hz, 1H), 7.72 (d, J=7.0 Hz, 1H), 7.52 (t, J=7.9 Hz, 1H), 7.34 (d, J=7.5 Hz, 1H), 7.22 (d, J=7.6 Hz, 2H), 4.45-4.40 (m, 2H), 4.04 (ddq, J=29.0, 14.6, 7.2 Hz, 2H), 3.29 (s, 9H), 2.78-2.71 (m, 2H), 2.09-1.84 (m, 3H).

UDP-Glo™ Glucosylceramide Synthase Biochemical Assay

A UDP-Glo™ glucosylceramide synthase biochemical assay was utilized to evaluate the effect of test compounds on the activity of endogenous levels of GCS enzyme contained within Golgi preparations isolated from human A375 malignant melanoma skin cells. The UDP-Glo™ glucosylceramide synthase assay uses UDP-Glucose as a nucleotide-glycosyl donor and ceramide as substrate acceptor molecules. In the reaction, glucosylceramide synthase (GCS) transfers glucose from UDP-Glucose to ceramide. Glucosylceramide and UDP are released as products.

Using Promega's UDP-Glo™ Glycosyltransferase assay kit (Promega Corporation, Madison, WI, USA (Promega)), GCS activity was indirectly measured by detecting the amount of UDP produced. An aliquot of GCS enzyme (1.5 μg crude golgi preparation, total protein) and titrated test compound were aliquoted to each well and incubated for 30 minutes at room temperature. Substrate mixture was prepared by mixing C6 ceramide (Avanti Polar Lipids, Alabaster, AL USA (Avanti)) (micelles prepared at 0.6 mM in 0.6 mM DOPC) and UDP-glucose (20 μM; Promega), at concentrations equivalent to 2×Km, in assay buffer (25 mM HEPES (pH 7.5), 50 mM KCl, 5 mM MgCl2). An equivalent volume of substrate mixture was then added to each well. Following a 20 h incubation at room temperature to allow for GCS turnover of substrate, an equal volume of UDP detection reagent (Promega) was added to each well and incubated for an additional 75 minutes at room temperature to simultaneously convert the accumulated UDP product into ATP and generate light in a luciferase reaction. The generated light was detected using a luminometer. Random luminescence values (RLUs) were normalized to mean "min" and "max" effects, as determined on each plate. "Min" was defined as the mean of the values of the wells treated with vehicle (DMSO) and which represent 0% inhibition; "max" was defined as the mean of the values of the wells treated with a reference inhibitor and which represent the 100% effect. Values for % Emax and EC50 were determined by best-fitting the normalized data to a curve in Activity Base along a four-parameter logistic non-linear regression (4PL) model (based on the Levenberg-Marquardt algorithm and defined by the equation below):

$$y = n + \frac{m - n}{1 + \left(\frac{i}{x}\right)^p}$$

where: n is 4PMin (bottom of the curve); m is 4PMax (top of the curve); i is IP (inflection point of curve); and p is slope. See Levenberg, K., "A Method for the Solution of Certain Problems in Least Squares", *Quart. Appl. Math.* 2, (1944), pp 164-168 and Marquardt, D., "An Algorithm for Least Squares Estimation on Nonlinear Parameters", *SIAM J. Appl. Math.* 11, (1963) pp 431-441.

$EC_{50}$ values from the aforementioned assay for the compounds of this invention range between 0.02 nM to 5000 nM. $EC_{50}$ values for particular embodiments of this invention are provided in Table 3 below.

TABLE 3

| Compound Number | GCS $EC_{50}$ (nM) |
|---|---|
| 1 | 9.8 |
| 2 | 6.1 |
| 3 | 3.1 |
| 4 | 26 |
| 5 | 0.91 |
| 6 | 2.4 |
| 7 | 1.2 |
| 8 | 4.5 |
| 9 | 2.3 |
| 10 | 7.2 |
| 11 | 38 |
| 12 | 36 |
| 13 | 5.8 |
| 14 | 0.97 |
| 15 | 0.029 |
| 16 | 0.83 |
| 17 | 1.2 |
| 18 | 2.3 |
| 19 | 23 |
| 20 | 0.86 |
| 21 | 11 |
| 22 | 0.72 |
| 23 | 10 |
| 24 | 0.36 |
| 25 | 2.5 |
| 26 | 0.79 |
| 27 | 1.3 |
| 28 | 7.4 |
| 29 | 2.1 |
| 30 | 5.6 |
| 31 | 0.23 |
| 32 | 47 |
| 33 | 14 |
| 34 | 5.9 |
| 35 | 3.3 |
| 36 | 2.1 |
| 37 | 4.5 |
| 38 | 5.5 |
| 39 | 14 |
| 40 | 6.7 |
| 41 | 1.7 |
| 42 | 2.5 |
| 43 | 2.1 |
| 44 | 8.3 |
| 45 | 4.3 |
| 46 | 4.0 |
| 47 | 9.2 |
| 48 | 4.5 |
| 49 | 18 |
| 50 | 21 |
| 51 | 0.51 |
| 52 | 13 |
| 53 | 30 |
| 54 | 3.0 |
| 55 | 2.9 |
| 56 | 0.15 |
| 57 | 0.45 |
| 58 | 28 |
| 59 | 6.0 |
| 60 | 30 |
| 61 | 0.083 |
| 62 | 17 |
| 63 | 5.7 |
| 64 | 13 |
| 65 | 1.3 |
| 66 | 15 |
| 67 | 67 |
| 68 | 10 |
| 69 | 15 |
| 70 | 0.061 |
| 71 | 16 |
| 72 | 7.9 |
| 73 | 32 |
| 74 | 12 |
| 75 | 30 |
| 76 | 13 |
| 77 | 3.7 |
| 78 | 32 |
| 79 | 140 |
| 80 | 330 |
| 81 | 11 |

TABLE 3-continued

| Compound Number | GCS $EC_{50}$ (nM) |
|---|---|
| 82 | 3.0 |
| 83 | 6.9 |
| 84 | 16 |

What is claimed is:

1. A compound of the formula I:

I

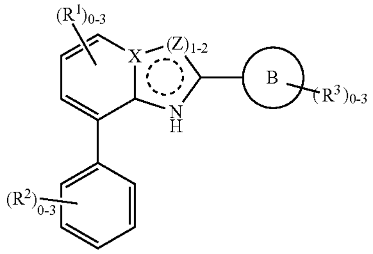

or a pharmaceutically acceptable salt thereof, wherein

X is C or N, provided that when there is one Z moiety present, then X is N;

Z is —$CR^4$—, each $R^1$ is independently C1-C4 alkyl, C1-C4 fluoroalkyl, —C0-C4alkylOH, cyano, C1-C4alkoxy, or halo;

each $R^4$ is independently hydrogen, C1-C4 alkyl, C1-C4 fluoroalkyl, —C0-C4alkylOH, cyano, C1-C4alkoxy, or halo;

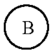

is selected from (tetrahydropuranyl)aminocarbonyl, (tetrahydro-2H-puranyl)aminocarbonyl, (1,1, 1-trifluoro-2-methylprop-2yl) aminocarbonyl, (tetrahydrofuranyl)aminocarbonyl, cyclopropylaminocarbonyl, piperazinylcarbonyl, isobutylaminocarbonyl, (3,3,3-trifluoroprop-2yl)aminocarbonyl, tertbutylaminocarbonyl, (6,7-dihydropyrrolo [3,4-b]pyridyl)carbonyl ((6,7-dihydro-5H-pyrrolo [3,4-b]pyridyl)carbonyl), 1-hydroxyethyl, 2-hydroxyprop-2yl, hydroxymethyl, dihydrooxazolyl, 4,5-dihydrooxazolyl, pyridinylaminocarbonyl, 2-pyridylaminocarbonyl, 3-pyridylaminocarbonyl, (4-pyridyl) aminocarbonyl, piperidinylaminocarbonyl, (bicyclo [2.2.2]octanyl)aminocarbonyl, cyclopentylaminocarbonyl, cyclohexylaminocarbonyl, (trifluoromethylaminomethyl)aminocarbonyl, (trifluoromethylaminoethyl) aminocarbonyl, (bicyclo[2.2.1]heptyl)aminocarbonyl, tetrahydropyranylaminocarbonyl, N-(tetrahydro-2H-pyran-3-yl)aminocarbonyl, (pyridylmethyl)aminocarbonyl, cyclobutylaminocarbonyl, (bicyclo[1.1.1]pentyl)aminocarbonyl, (azabicyclo[2.1.1]hexyl)carbonyl, (2-azabicyclo [2.1.1]hexyl)carbonyl, (oxadiazaspiro [3.5]nonyl)carbonyl, (5-oxa-2,8-diazaspiro [3.5]nonyl) carbonyl, (dioxaazaspiro [4.5]decyl)carbonyl, (2,9-dioxa-6-azaspiro [4.5]decyl)carbonyl, (dioxaazaspiro [3.5]nonyl)carbonyl, (2,5-dioxa-8-azaspiro [3.5]nonyl) carbonyl, dihydrooxazolyl, 4,5-dihydrooxazolyl, (pyridylmethyl)aminocarbonyl, (2-pyridylmethyl) aminocarbonyl, (oxetanyl)aminocarbonyl, (3-oxetanyl) aminocarbonyl, oxadiazaspiro [3.4]octenyl, 5-oxa-2,7-diazaspiro [3.4]oct-6-enyl, (pyrrolidinylethyl) aminocarbonyl, (5,6,7,8-tetrahydroimidazo[1,2-a] pyrazinyl)carbonyl, aminomethyl, (azabicyclo[3.1.0] hexyl)carbonyl, (3-azabicyclo [3.1.0]hexyl)carbonyl, cyclopropylmethyl, (tert-butyl)aminomethyl, (tetrahydropyranyl) methyl, (tetrahydro-2H-pyranyl) methyl, and cyclobutylcarbonylamino;

each $R^2$ is independently selected from halo, (C1-C4 fluoroalkyl) oxy, hydroxy, C1-C4 alkyl, and —(C0-C4 alkyl) O (C1-C4 alkyl); and each $R^3$ is independently selected from C1-C4 alkyl, halo, oxo, cyano, amino, C1-C4 fluoroalkyl, hydroxy, —(C0-C4alkyl)O(C1-C4 alkyl), and —(C1-C4 alkyl)OH.

2. The compound of claim 1 or a pharmaceutically acceptable salt thereof, wherein each $R^1$ is independently methyl, ethyl, propyl, difluoromethyl, trifluoromethyl, 2,2,2-trifluoroethyl, hydroxy, hydroxymethyl, cyano, methoxy, ethoxy, chloro, or fluoro.

3. The compound of claim 1 or a pharmaceutically acceptable salt thereof, wherein each $R^1$ is independently chloro, trifluoromethyl, methoxy, fluoro, or cyano.

4. The compound of claim 3 or a pharmaceutically acceptable salt thereof, wherein each $R^2$ independently is chloro, fluoro, trifluoromethoxy, trifluoroethoxy, 2,2,2-trifluoroethoxy, hydroxy, methyl, ethyl, isopropyl, methoxy, ethoxy, ethoxymethyl, or methoxymethyl.

5. The compound of claim 1 or a pharmaceutically acceptable salt thereof, wherein each $R^3$ independently is selected from methyl, ethyl, propyl, isopropyl, butyl, fluoro, chloro, oxo, cyano, amino, trifluoromethyl, 2,2,2-trifluoroethyl, hydroxy, methoxy, ethoxy, propoxy, hydroxymethyl, hydroxyethyl, hydroxypropyl, and 2-hydroxy(prop-2yl).

6. The compound of claim 5 or a pharmaceutically acceptable salt thereof, wherein each $R^3$ independently is selected from fluoro, methyl, hydroxymethyl, fluoromethyl, aminomethyl, 2-hydroxy(prop-2yl), hydroxy, cyano, methoxyethyl, methoxymethyl, trifluoromethyl and methoxy.

7. The compound of claim 6 or a pharmaceutically acceptable salt thereof, wherein each $R^4$ independently is selected from hydrogen, methyl, ethyl, propyl, isopropyl, butyl, trifluoromethyl, trifluoroethyl, trifluoropropyl, fluoromethyl, difluoromethyl, difluoroethyl, hydroxy, hydroxymethyl, hydroxyethyl, hydroxyisopropyl, hydroxypropyl, cyano, methoxy, ethoxy, propoxy, isopropoxy, butoxy, chloro, fluoro, and bromo.

8. The compound of claim 7 or a pharmaceutically acceptable salt thereof, wherein each $R^4$ independently is hydrogen or fluoro.

9. The compound of claim 8 or a pharmaceutically acceptable salt thereof, wherein X is C.

10. The compound of claim 8 or a pharmaceutically acceptable salt thereof, wherein X is N.

11. The compound of claim 1, or a pharmaceutically acceptable salt thereof, selected from:

N-(1-hydroxy-2-methylpropan-2-yl)-8-(2-(2,2,2-trifluoroethoxy)phenyl)imidazo[1,2-a]pyridine-2-carboxamide;

(R)—N-(tetrahydro-2H-pyran-3-yl)-8-(2-(2,2,2-trifluoroethoxy)phenyl)imidazo[1,2-a]pyridine-2-carboxamide;

(S)—N-(tetrahydro-2H-pyran-3-yl)-8-(2-(2,2,2-trifluoroethoxy)phenyl)imidazo[1,2-a]pyridine-2-carboxamide;

N-(1,1,1-trifluoro-2-methylpropan-2-yl)-8-(2-(2,2,2-trifluoroethoxy)phenyl)imidazo[1,2-a]pyridine-2-carboxamide;

(R)-8-(2-(2,2,2-trifluoroethoxy)phenyl)-N-(1,1,1-trifluoropropan-2-yl)imidazo[1,2-a]pyridine-2-carboxamide;
(S)-6-chloro-N-(tetrahydrofuran-3-yl)-8-(2-(2,2,2-trifluoroethoxy)phenyl)imidazo[1,2-a]pyridine-2-carboxamide;
6-chloro-N-(1-(methoxymethyl)cyclopropyl)-8-(2-(2,2,2-trifluoroethoxy)phenyl)imidazo[1,2-a]pyridine-2-carboxamide;
(6-chloro-8-(2-(2,2,2-trifluoroethoxy)phenyl)imidazo[1,2-a]pyridin-2-yl) (3,3,4-trimethylpiperazin-1-yl) methanone;
6-chloro-N-(2-cyano-2-methylpropyl)-8-(2-(2,2,2-trifluoroethoxy)phenyl)imidazo[1,2-a]pyridine-2-carboxamide;
(S)—N-(1,1,1-trifluoro-3-hydroxy-2-methylpropan-2-yl)-8-(2-(2,2,2-trifluoroethoxy)phenyl)imidazo[1,2-a]pyridine-2-carboxamide;
(R)—N-(1,1,1-trifluoro-3-hydroxy-2-methylpropan-2-yl)-8-(2-(2,2,2-trifluoroethoxy)phenyl)imidazo[1,2-a]pyridine-2-carboxamide;
(R)—N-(1,1,1-trifluoro-3-hydroxy-2-methylpropan-2-yl)-8-(2-(2,2,2-trifluoroethoxy)phenyl)imidazo[1,2-a]pyridine-2-carboxamide;
(S)—N-(1,1,1-trifluoro-3-hydroxy-2-methylpropan-2-yl)-8-(2-(2,2,2-trifluoroethoxy)phenyl)imidazo[1,2-a]pyridine-2-carboxamide;
N-(1-methoxy-2-methylpropan-2-yl)-8-(2-(2,2,2-trifluoroethoxy)phenyl)imidazo[1,2-a]pyridine-2-carboxamide;
(5,7-dihydro-6H-pyrrolo [3,4-b]pyridin-6-yl) (8-(2-(2,2,2-trifluoroethoxy)phenyl)imidazo[1,2-a]pyridin-2-yl) methanone;
N-(tert-butyl)-6-fluoro-8-(2-(2,2,2-trifluoroethoxy)phenyl)imidazo[1,2-a]pyridine-2-carboxamide;
(R)-6-chloro-N-(3-methyltetrahydrofuran-3-yl)-8-(2-(2,2,2-trifluoroethoxy)phenyl)imidazo[1,2-a]pyridine-2-carboxamide;
(S)-6-chloro-N-(3-methyltetrahydrofuran-3-yl)-8-(2-(2,2,2-trifluoroethoxy)phenyl)imidazo[1,2-a]pyridine-2-carboxamide;
N-(pyridin-3-yl)-8-(2-(2,2,2-trifluoroethoxy)phenyl)-6-(trifluoromethyl)imidazo[1,2-a]pyridine-2-carboxamide;
N-(trans-4-fluoropiperidin-3-yl)-8-(2-(2,2,2-trifluoroethoxy)phenyl)imidazo[1,2-a]pyridine-2-carboxamide;
(R)—N-(4,4-difluoropiperidin-3-yl)-8-(2-(2,2,2-trifluoroethoxy)phenyl)imidazo[1,2-a]pyridine-2-carboxamide;
(S)—N-(4,4-difluoropiperidin-3-yl)-8-(2-(2,2,2-trifluoroethoxy)phenyl)imidazo[1,2-a]pyridine-2-carboxamide;
N-(4-(hydroxymethyl) bicyclo[2.2.2]octan-1-yl)-8-(2-(2,2,2-trifluoroethoxy)phenyl)imidazo[1,2-a]pyridine-2-carboxamide;
N-(trans-3-hydroxycyclopentyl)-8-(2-(2,2,2-trifluoroethoxy)phenyl)imidazo[1,2-a]pyridine-2-carboxamide;
6-chloro-N-(1-hydroxy-2-methylpropan-2-yl)-8-(2-(2,2,2-trifluoroethoxy)phenyl)imidazo[1,2-a]pyridine-2-carboxamide;
N-(1-(hydroxymethyl) cyclopentyl)-8-(2-(2,2,2-trifluoroethoxy)phenyl)imidazo[1,2-a]pyridine-2-carboxamide;
6-chloro-N-((1S,2R,4S)-2-fluoro-4-hydroxycyclohexyl)-8-(2-(2,2,2-trifluoroethoxy)phenyl)imidazo[1,2-a]pyridine-2-carboxamide;
6-chloro-N-((1R,2S,4R)-2-fluoro-4-hydroxycyclohexyl)-8-(2-(2,2,2-trifluoroethoxy)phenyl)imidazo[1,2-a]pyridine-2-carboxamide;
N-(2-amino-3,3,3-trifluoropropyl)-6-chloro-8-(2-(2,2,2-trifluoroethoxy)phenyl)imidazo[1,2-a]pyridine-2-carboxamide;
6-chloro-N-(trans-4-hydroxycyclohexyl)-8-(2-(2,2,2-trifluoroethoxy)phenyl)imidazo[1,2-a]pyridine-2-carboxamide;
6-chloro-N-(4-hydroxybicyclo [2.2.1]heptan-1-yl)-8-(2-(2,2,2-trifluoroethoxy)phenyl)imidazo[1,2-a]pyridine-2-carboxamide;
cis-6-fluoro-N-(4-hydroxy-4-methylcyclohexyl)-8-(2-(2,2,2-trifluoroethoxy)phenyl)imidazo[1,2-a]pyridine-2-carboxamide;
trans-6-fluoro-N-(4-hydroxy-4-methylcyclohexyl)-8-(2-(2,2,2-trifluoroethoxy)phenyl)imidazo[1,2-a]pyridine-2-carboxamide;
6-fluoro-N-(cis-4-(hydroxymethyl)cyclohexyl)-8-(2-(2,2,2-trifluoroethoxy)phenyl)imidazo[1,2-a]pyridine-2-carboxamide;
N-cyclopentyl-6-fluoro-8-(2-(2,2,2-trifluoroethoxy)phenyl)imidazo[1,2-a]pyridine-2-carboxamide;
N-(trans-4-(hydroxymethyl)cyclohexyl)-8-(2-(2,2,2-trifluoroethoxy)phenyl)imidazo[1,2-a]pyridine-2-carboxamide;
8-(5-chloro-2-methoxyphenyl)-N-(4-hydroxybicyclo [2.2.1]heptan-1-yl)imidazo[1,2-a]pyridine-2-carboxamide;
N-(cis-3-(hydroxymethyl)cyclohexyl)-8-(2-(2,2,2-trifluoroethoxy)phenyl)imidazo[1,2-a]pyridine-2-carboxamide;
3-fluoro-N-(trans-4-hydroxycyclohexyl)-8-(2-(2,2,2-trifluoroethoxy)phenyl)imidazo[1,2-a]pyridine-2-carboxamide;
3-fluoro-N-(1,1,1-trifluoro-2-methylpropan-2-yl)-8-(2-(2,2,2-trifluoroethoxy)phenyl)imidazo[1,2-a]pyridine-2-carboxamide;
(S)—N-(3-cyanotetrahydrofuran-3-yl)-8-(2-(2,2,2-trifluoroethoxy)phenyl)imidazo[1,2-a]pyridine-2-carboxamide;
(R)-6-chloro-N-(3-methyltetrahydro-2H-pyran-3-yl)-8-(2-(2,2,2-trifluoroethoxy)phenyl)imidazo[1,2-a]pyridine-2-carboxamide;
(S)-6-chloro-N-(3-methyltetrahydro-2H-pyran-3-yl)-8-(2-(2,2,2-trifluoroethoxy)phenyl)imidazo[1,2-a]pyridine-2-carboxamide;
N-(trans-4-hydroxycyclohexyl)-8-(2-(2,2,2-trifluoroethoxy)phenyl)-6-(trifluoromethyl)imidazo[1,2-a]pyridine-2-carboxamide;
N-(1-hydroxy-2-methylpropan-2-yl)-8-(2-(2,2,2-trifluoroethoxy)phenyl)-6-(trifluoromethyl)imidazo[1,2-a]pyridine-2-carboxamide;
(R)—N-(2,2,2-trifluoro-1-(pyridin-3-yl) ethyl)-8-(2-(2,2,2-trifluoroethoxy)phenyl)imidazo[1,2-a]pyridine-2-carboxamide;
(S)—N-(2,2,2-trifluoro-1-(pyridin-3-yl) ethyl)-8-(2-(2,2,2-trifluoroethoxy)phenyl)imidazo[1,2-a]pyridine-2-carboxamide;
6-cyano-N-(trans-4-hydroxycyclohexyl)-8-(2-(2,2,2-trifluoroethoxy)phenyl)imidazo[1,2-a]pyridine-2-carboxamide;
N-cis-3-(hydroxymethyl) cyclobutyl)-8-(2-(2,2,2-trifluoroethoxy)phenyl)imidazo[1,2-a]pyridine-2-carboxamide;
6-fluoro-N-(1,1,1-trifluoro-2-methylpropan-2-yl)-8-(2-(2,2,2-trifluoroethoxy)phenyl)imidazo[1,2-a]pyridine-2-carboxamide;

(S)—N-(tetrahydro-2H-pyran-3-yl)-8-(2-(2,2,2-trifluoroethoxy)phenyl)-6-(trifluoromethyl)imidazo[1,2-a]pyridine-2-carboxamide;

6-methoxy-N-(1,1,1-trifluoro-2-methylpropan-2-yl)-8-(2-(2,2,2-trifluoroethoxy)phenyl)imidazo[1,2-a]pyridine-2-carboxamide;

6-cyano-N-(1,1,1-trifluoro-2-methylpropan-2-yl)-8-(2-(2,2,2-trifluoroethoxy)phenyl)imidazo[1,2-a]pyridine-2-carboxamide;

6-chloro-N-((3R,4R)-4-fluorotetrahydrofuran-3-yl)-8-(2-(2,2,2-trifluoroethoxy)phenyl)imidazo[1,2-a]pyridine-2-carboxamide;

6-chloro-N-((3S,4R)-4-fluorotetrahydrofuran-3-yl)-8-(2-(2,2,2-trifluoroethoxy)phenyl)imidazo[1,2-a]pyridine-2-carboxamide;

N-(3-(hydroxymethyl) bicyclo[1.1.1]pentan-1-yl)-8-(2-(2,2,2-trifluoroethoxy)phenyl)imidazo[1,2-a]pyridine-2-carboxamide;

(1-(fluoromethyl)-2-azabicyclo [2.1.1]hexan-2-yl) (8-(2-(2,2,2-trifluoroethoxy)phenyl)imidazo[1,2-a]pyridin-2-yl) methanone;

(2-methyl-5-oxa-2,8-diazaspiro [3.5]nonan-8-yl) (8-(2-(2,2,2-trifluoroethoxy)phenyl)imidazo[1,2-a]pyridin-2-yl) methanone;

(R)-(2,6-dioxa-9-azaspiro [4.5]decan-9-yl) (8-(2-(2,2,2-trifluoroethoxy)phenyl)imidazo[1,2-a]pyridin-2-yl) methanone;

(S)-(2,6-dioxa-9-azaspiro [4.5]decan-9-yl) (8-(2-(2,2,2-trifluoroethoxy)phenyl)imidazo[1,2-a]pyridin-2-yl) methanone;

(2,5-dioxa-8-azaspiro [3.5]nonan-8-yl) (8-(2-(2,2,2-trifluoroethoxy)phenyl)-6-(trifluoromethyl)imidazo[1,2-a]pyridin-2-yl) methanone;

N-(pyridin-2-ylmethyl)-8-(2-(2,2,2-trifluoroethoxy)phenyl)imidazo[1,2-a]pyridine-2-carboxamide;

N-(2,2-dimethyloxetan-3-yl)-8-(2-(2,2,2-trifluoroethoxy)phenyl)imidazo[1,2-a]pyridine-2-carboxamide;

N-methyl-N-(2-(pyrrolidin-1-yl) ethyl)-8-(2-(2,2,2-trifluoroethoxy)phenyl)imidazo[1,2-a]pyridine-2-carboxamide;

(5,6-dihydroimidazo[1,2-a] pyrazin-7 (8H)-yl) (8-(2-(2,2,2-trifluoroethoxy)phenyl)imidazo[1,2-a]pyridin-2-yl) methanone;

N-(4-methylpyridin-3-yl)-8-(2-(2,2,2-trifluoroethoxy) phenyl)imidazo[1,2-a]pyridine-2-carboxamide;

N-(4-fluoropyridin-3-yl)-8-(2-(2,2,2-trifluoroethoxy)phenyl)imidazo[1,2-a]pyridine-2-carboxamide;

3-(8-(2-(2,2,2-trifluoroethoxy)phenyl)imidazo[1,2-a] pyridine-2-carboxamido) pyridine 1-oxide;

N-(3-cyanopyridin-4-yl)-8-(2-(2,2,2-trifluoroethoxy)phenyl)imidazo[1,2-a]pyridine-2-carboxamide;

(6-chloro-8-(2-(2,2,2-trifluoroethoxy)phenyl)imidazo[1,2-a]pyridin-2-yl)((1R,5R)-6-(hydroxymethyl)-3-azabicyclo [3.1.0]hexan-3-yl) methanone;

6-fluoro-N-(pyridin-3-yl)-8-(2-(2,2,2-trifluoroethoxy) phenyl)imidazo[1,2-a]pyridine-2-carboxamide;

(8-(2-(2,2,2-trifluoroethoxy)phenyl)-6-(trifluoromethyl) imidazo[1,2-a]pyridin-2-yl) methanol;

(R) 1-(8-(2-(2,2,2-trifluoroethoxy)phenyl)-6-(trifluoromethyl)imidazo[1,2-a]pyridin-2-yl) ethan-1-ol;

(S) 1-(8-(2-(2,2,2-trifluoroethoxy)phenyl)-6-(trifluoromethyl)imidazo[1,2-a]pyridin-2-yl) ethan-1-ol;

1-[6-chloro-8-[2-(2,2,2-trifluoroethoxy)phenyl]imidazo [1,2-a]pyridin-2-yl] ethanol;

[6-chloro-8-[2-(2,2,2-trifluoroethoxy)phenyl]imidazo[1,2-a]pyridin-2-yl]-cyclopropyl-methanol;

2-(6-chloro-8-(2-(2,2,2-trifluoroethoxy)phenyl)imidazo [1,2-a]pyridin-2-yl) propan-2-ol;

2-(6-chloro-8-(4-fluoro-2-(2,2,2-trifluoroethoxy)phenyl) imidazo[1,2-a]pyridin-2-yl) propan-2-ol;

(6-fluoro-8-(2-(2,2,2-trifluoroethoxy)phenyl)imidazo[1,2-a]pyridin-2-yl) (tetrahydro-2H-pyran-4-yl) methanol;

2-(6-chloro-8-(2-(2,2,2-trifluoroethoxy)phenyl)imidazo [1,2-a]pyridin-2-yl)-5,5-dimethyl-4,5-dihydrooxazole;

6-[6-chloro-8-[2-(2,2,2-trifluoroethoxy)phenyl]imidazo [1,2-a]pyridin-2-yl]-2-methyl-5-oxa-2,7-diazaspiro [3.4]oct-6-ene;

(2-(6-chloro-8-(2-(2,2,2-trifluoroethoxy)phenyl)imidazo [1,2-a]pyridin-2-yl)-5-methyl-4,5-dihydrooxazol-5-yl) methanol;

[2-[6-chloro-8-[2-(2,2,2-trifluoroethoxy)phenyl]imidazo [1,2-a]pyridin-2-yl]-4,5-dihydrooxazol-4-yl] methanol;

[2-[6-chloro-8-[2-(2,2,2-trifluoroethoxy)phenyl]imidazo [1,2-a]pyridin-2-yl]-4-methyl-5H-oxazol-4-yl] methanol;

(2-(6-chloro-8-(2-(2,2,2-trifluoroethoxy)phenyl)imidazo [1,2-a]pyridin-2-yl)-4,5-dihydrooxazol-5-yl) methanamine;

2-(2-(6-chloro-8-(2-(2,2,2-trifluoroethoxy)phenyl)imidazo[1,2-a]pyridin-2-yl)-4,5-dihydrooxazol-4-yl) propan-2-ol;

2-[2-[6-chloro-8-[2-(2,2,2-trifluoroethoxy)phenyl]imidazo[1,2-a]pyridin-2-yl]-4,5-dihydrooxazol-5-yl] propan-2-ol;

2-[2-[6-chloro-8-[2-(2,2,2-trifluoroethoxy)phenyl]imidazo[1,2-a]pyridin-2-yl]-5-methyl-4H-oxazol-5-yl] propan-2-ol;

2-[2-[6-chloro-8-[2-(2,2,2-trifluoroethoxy)phenyl]imidazo[1,2-a]pyridin-2-yl]-4-methyl-5H-oxazol-4-yl] propan-2-ol;

2-methyl-N-((8-(2-(2,2,2-trifluoroethoxy)phenyl)imidazo [1,2-a]pyridin-2-yl) methyl) propan-2-amine;

(8-(2-(2,2,2-trifluoroethoxy)phenyl)imidazo[1,2-a]pyridin-2-yl) methanamine;

cis-3-hydroxy-N-(8-(2-(2,2,2-trifluoroethoxy)phenyl) quinolin-2-yl) cyclobutane-1-carboxamide;

trans-3-hydroxy-N-(8-(2-(2,2,2-trifluoroethoxy)phenyl) quinolin-2-yl) cyclobutane-1-carboxamide;

trans-N-(5-fluoro-8-(2-(2,2,2-trifluoroethoxy)phenyl) quinolin-2-yl)-3-hydroxycyclobutane-1-carboxamide; and N-cis-3-hydroxycyclobutyl)-5-(2-(2,2,2-trifluoroethoxy) phenyl) isoquinoline-3-carboxamide.

12. A pharmaceutical composition comprising an effective amount of a compound of claim 1, or a pharmaceutically acceptable salt thereof, and a pharmaceutically acceptable carrier.

13. The pharmaceutical composition of claim 12, or a pharmaceutically acceptable salt thereof, further comprising one or more additional therapeutic agents.

14. A method for treatment of lysosomal storage diseases, kidney disease, neurodegenerative disease, diabetes related diseases, or cancers where GSL synthesis is abnormal or overexpression of GCS disrupts ceramide-induced apoptosis, which comprises administering to a subject in need of such treatment a therapeutically effective amount of a compound according to claim 1, or a pharmaceutically acceptable salt thereof.

15. A method for treatment of Parkinson's Disease comprising administering to a subject in need of such treatment a therapeutically effective amount of a compound according to claim 1.

16. A method for treatment of a disease selected from dementia with Lewy bodies, polycystic kidney disease, renal hypertrophy, diabetes mellitus, obesity, hyperglycemia, hyperinsulemia, leukemia, papillary renal cancer, and thyroid carcinomas, comprising administering to a subject in need of such treatment a therapeutically effective amount of a compound according to claim 1.

* * * * *